US009278134B2

(12) United States Patent
Rogers et al.

(10) Patent No.: US 9,278,134 B2
(45) Date of Patent: Mar. 8, 2016

(54) DUAL FUNCTIONING IONIC LIQUIDS AND SALTS THEREOF

(75) Inventors: Robin D. Rogers, Tuscaloosa, AL (US);
Daniel T. Daly, Tuscsaloosa, AL (US);
Douglas MacFarlane, Victoria (AU);
Janet L. Scott, Port Sunlight (GB);
Kenneth R. Seddon, Donaghadee (IE);
Gabriela Gurau, Tuscaloosa, AL (US);
Katharina Bica, Vienna (AT); Jelena Turanjanin, Victoria (AU); Pamela M. Dean, Victoria (AU)

(73) Assignees: The Board of Trustees of the University of Alabama, Tuscaloosa, AL (US); Monash University, Melbourne (AU); Queen's University Belfast, Belfast (GB)

( * ) Notice: Subject to any disclaimer, the term of this patent is extended or adjusted under 35 U.S.C. 154(b) by 156 days.

(21) Appl. No.: 13/142,559

(22) PCT Filed: Dec. 29, 2009

(86) PCT No.: PCT/US2009/069652
§ 371 (c)(1),
(2), (4) Date: Nov. 3, 2011

(87) PCT Pub. No.: WO2010/078300
PCT Pub. Date: Jul. 8, 2010

(65) Prior Publication Data
US 2012/0046244 A1 Feb. 23, 2012

Related U.S. Application Data

(60) Provisional application No. 61/141,168, filed on Dec. 29, 2008.

(51) Int. Cl.
*A61K 31/66* (2006.01)
*A61K 31/205* (2006.01)
*A61K 47/48* (2006.01)

(52) U.S. Cl.
CPC ................... *A61K 47/4803* (2013.01)

(58) Field of Classification Search
None
See application file for complete search history.

(56) References Cited

U.S. PATENT DOCUMENTS

| 1,943,176 | A | 1/1934 | Graenacher |
|---|---|---|---|
| 2,004,891 | A | 6/1935 | Goldberg et al. |
| 4,063,017 | A | 12/1977 | Tsao et al. |
| 4,097,666 | A | 6/1978 | Johnson et al. |
| 4,171,352 | A | 10/1979 | Wolgemuth et al. |
| 4,188,263 | A | 2/1980 | Hulsmann et al. |
| 4,421,547 | A | 12/1983 | Prisbylla |
| 4,520,105 | A | 5/1985 | Sinner et al. |
| 4,522,934 | A | 6/1985 | Shum et al. |
| 4,891,386 | A | * 1/1990 | Gasparotti .............. 514/555 |
| 4,970,156 | A | 11/1990 | Avrameas et al. |
| 5,221,758 | A | 6/1993 | Maynard |
| 5,246,716 | A | 9/1993 | Sedun et al. |
| 5,679,146 | A | 10/1997 | Kalt et al. |
| 5,683,832 | A | 11/1997 | Bonhôte et al. |
| 5,714,536 | A | 2/1998 | Ziolo et al. |
| 5,747,125 | A | 5/1998 | Markulin |
| 5,792,399 | A | 8/1998 | Meister et al. |
| 5,827,602 | A | 10/1998 | Koch et al. |
| 5,856,513 | A | 1/1999 | Ue et al. |
| 6,001,342 | A | 12/1999 | Forestier et al. |
| 6,376,712 | B2 | 4/2002 | Narizuka et al. |
| 6,451,220 | B1 | 9/2002 | Ziolo et al. |
| 6,613,310 | B1 | 9/2003 | Campbell et al. |
| 6,808,557 | B2 | 10/2004 | Holbrey et al. |
| 6,824,599 | B2 | 11/2004 | Swatloski et al. |
| 6,967,074 | B2 | 11/2005 | Duffy et al. |
| 2002/0010291 | A1 | 1/2002 | Murphy |
| 2003/0059604 | A1 | 3/2003 | Hattori et al. |
| 2003/0157351 | A1 | 8/2003 | Swatloski et al. |
| 2003/0165445 | A1 | 9/2003 | Malnou et al. |
| 2003/0233742 | A1 | 12/2003 | Jones et al. |
| 2004/0038031 | A1 | 2/2004 | Holbrey et al. |
| 2005/0123851 | A1 | 6/2005 | Shinbori et al. |
| 2005/0194561 | A1 | 9/2005 | Davis |
| 2005/0196671 | A1 | 9/2005 | Paonessa et al. |
| 2005/0285073 | A1 | 12/2005 | Singh et al. |
| 2006/0090271 | A1 | 5/2006 | Price et al. |
| 2006/0090777 | A1 | 5/2006 | Hecht et al. |
| 2006/0094617 | A1 | 5/2006 | Price et al. |
| 2006/0118755 | A1 | 6/2006 | Fujioka et al. |
| 2006/0128996 | A1 | 6/2006 | Vaultier et al. |

(Continued)

FOREIGN PATENT DOCUMENTS

| CA | 2479941 | 10/2003 |
|---|---|---|
| CH | 153446 | 6/1932 |

(Continued)

OTHER PUBLICATIONS

International Search Report and Written Opinion for Application No. PCT/US2011/047619 dated Apr. 9, 2012.
Wasserscheid et al., Ionic liquids—new "solutions" for transition metal catalysis, Angew Chem. Int. Ed. Engl., 39:3772-3789 (2000).
Weckstrom et al., Entrapment of Whole Cell Yeast β-Galactosidase in Precipated Cellulose Derivatives, Food Process Eng., vol. 2, Applied Science Publishers Ltd., pp. 148-151 (1979).
Welton, Room-temperature ionic liquids. Solvents for synthesis and catalysis, Chem. Rev., 99:2071-2083 (1999).

(Continued)

Primary Examiner — Tigabu Kassa
(74) Attorney, Agent, or Firm — Meunier Carlin & Curfman LLC

(57) ABSTRACT

Disclosed herein are ionic liquid compositions comprising active pharmaceutical, biological, and nutritional compounds, and methods of use. Further disclosed are compositions of matter including liquid ion pairs alone or in solution and their use; compositions of ionic liquids that are 'solvated,' for example, 'hydrated' and their uses.

14 Claims, 7 Drawing Sheets

(56) References Cited

U.S. PATENT DOCUMENTS

| | | |
|---|---|---|
| 2006/0166856 A1 | 7/2006 | Petrat et al. |
| 2006/0194197 A1 | 8/2006 | Spangler et al. |
| 2007/0006774 A1 | 1/2007 | Rogers et al. |
| 2007/0093462 A1* | 4/2007 | Rogers et al. ............... 514/184 |
| 2007/0215300 A1 | 9/2007 | Upfal et al. |
| 2008/0023162 A1 | 1/2008 | Myllymaki et al. |
| 2008/0190013 A1 | 8/2008 | Argyropoulos |

FOREIGN PATENT DOCUMENTS

| | | |
|---|---|---|
| CN | 1380110 | 11/2002 |
| CN | 150409 | 6/2004 |
| DE | 2703703 | 1/1977 |
| DE | 4308410 | 9/1994 |
| DE | 10337579 | 4/2004 |
| EP | 0780391 | 6/1997 |
| EP | 1222918 | 7/2002 |
| EP | 1807497 | 7/2007 |
| EP | 1854786 | 11/2007 |
| JP | 58183601 | 10/1983 |
| JP | 63056501 | 3/1988 |
| JP | 64017649 | 1/1989 |
| JP | 80089796 | 4/1996 |
| JP | 10265674 | 10/1998 |
| JP | 2002290011 | 10/2002 |
| JP | 2003171144 | 6/2003 |
| JP | 2003335887 | 11/2003 |
| JP | 2004285044 | 10/2004 |
| JP | 2005082512 | 3/2005 |
| JP | 2007039820 | 2/2007 |
| WO | 9113552 A1 | 9/1991 |
| WO | WO9420521 | 9/1994 |
| WO | WO9521871 | 8/1995 |
| WO | WO9606593 | 3/1996 |
| WO | WO0032658 | 6/2000 |
| WO | WO0181436 | 11/2001 |
| WO | WO02079269 | 10/2002 |
| WO | WO02100360 | 12/2002 |
| WO | WO02102586 | 12/2002 |
| WO | WO03029329 | 4/2003 |
| WO | WO03041692 | 5/2003 |
| WO | WO03074031 | 9/2003 |
| WO | WO2004027897 | 4/2004 |
| WO | WO2005017252 | 2/2005 |
| WO | 2005028446 | 3/2005 |
| WO | WO2006050308 | 5/2006 |
| WO | 2007005470 A2 | 1/2007 |
| WO | WO2007005388 | 1/2007 |
| WO | WO2007063327 | 6/2007 |
| WO | WO2009105236 | 8/2009 |
| WO | 2009/11936 | 10/2009 |
| WO | WO2010056790 | 5/2010 |

OTHER PUBLICATIONS

Wilkes et al., Air and Water Stable 1-Ethyl-3-methylimidazolium Based Ionic Liquids, J. Chem. Soc. Chem. Commun., 965-967 (1992).

Willauer et al., Investigation of aqueous biphasic systems for the separation of lignins from cellulose in paper pulping process, J. Chromatogr. B: Biomed. Sci. Applic., 743(1-2):127-135 (2000).

Wu et al., Homogeneous Acetylation of Cellulose in a New Ionic Liquid, Biomacromol., 5:266-268 (2004).

Extended European Search Report for Application No. 06774039.9 dated Jul. 8, 2011.

Office Action for AU Patent Application No. 2006302237 dated Aug. 23, 2011.

Office Action for U.S. Appl. No. 11/545,938 dated Sep. 19, 2011.

Response to Office Action for AU Patent Application No. 2006302237 dated Feb. 6, 2012.

Response to Office Action for CN Patent Application No. 200680046195 dated Mar. 23, 2011.

Okutucu et al., Covalent Attachment of Oligonucleotides to Cellulose Acetate Membranes, Artificial Cells, Blood Substitutes, and Biotechnology, 32(4):599-608 (2004).

Butcher et al., Efficacy of Acidic and Alkaline Solutions of Alkylammonium Compounds as Wood Perservatives, J. For. Sci., 8:403-409 (1978).

Butcher et al., The Paint Index—The Colour Classification and Use of a Collection of Paint Samples taken from Scenes of Crime, J. For. Sci., 17:27-32 (1977).

Cateto et al., Monitoring of lignin-based polyurethane synthesis by FTIR-ATR, Ind. Crops Prod., 27(2):168-174 (2008).

Chesney et al., Amino-Derivatised Beaded Cellulose Gels, Novel Accessible and Biodegradable Scavenger Resins for Solution Phase Cominatorial Synthesis, Green Chem., 2:57-62 (2000).

Davey, Ionic Liquids in Consumer Products, Perf Flav., 33:34-35 (2008).

Deus et al., Partiell acetylierte Cellulose—Synthese and Bestimmung der Substituentenverteilung mit Hilfe der 1H NMR-Spektroskopie, Makromol. Chem., 192(1):75-83 (1991).

Domagk, A new class of disinfectants, Deut Med Wochenschr., 61:829-832 (1935).

Dykes, Review Dendrimers: a review of their appeal and applications, J. Chem. Tech. and Biotech., 76:903-918 (2001).

Earle et al., Ionic liquids. Green Solvents for the future, Pure Appl. Chem., 72(7):1391-1398 (2000).

El Seoud et al., Applications of ionic liquids in carbohydrate chemistry: A window of opportunities, Biomacromol, 8(9):2629-2647 (2007).

Endres, Ionic Liquids: Solvents for the Eletrodeposition of Metals and Semiconductors, Chem. Phys. Chem., 3(2):144-154 (2002).

Esfand et al., Poly(amidoamine) (PMAAM) dendrimers: from biomimicry to drug delivery and biomedical applications, 6(8):427-436 (2001).

Extended European Search Report for Application No. 101778231.1 issued May 11, 2011.

Fannin et al., Properties of 1,3-Dialkylimidazolium Chloride-Aluminum Choride Ionic Liquids. 2. Phase Transitions, Densities, Electrical Conductivities, and Viscosities, J. Phys. Chem., 88:2614-2621 (1984).

Fischer et al., Structural Changes of Cellulose Dissolved in Molten Salt Hydrates, 219th ACS National Meeting, San Francisco, CA (2000) (abstract).

Fischer et al, The behaviour of cellulose in hydrated melts of the composition LiX-nH2O (X=I-, NO-3, CH3COO-, ClO-4), Cellulose, 6:213-219 (1999).

Fort et al., Can ionic liquids dissolve wood? Processing and analysis of lignocellulosic materials with I-n-butyl-3-methylimidazolium chloride, Green Chem., 9:63-69 (2007).

Forsyth et al., Utilisation of ionic liquid solvents for the synthesis of Lily-of-the-Valley fragrance {B-Lilial; 3-(4-t-butylphenyl)-2-methylpropanal}, J. Mol. Cat. A., 231:61-66 (2005).

Froehner et al., Properties of the Glycoprotein Laccase Imobilised by Two Methods, Acta Chem Scand B, 29:691-694 (1975).

Fukaya et al., Cellulose dissolution with polar ionic liquids under mild conditions: required factors for anions, Green Chem., 10:44-46 (2008).

Gallezot, Process options for converting renewable feedstocks to bioproducts, Green Chem., 9:295-302 (2007).

Gelbrich, Colloid Structures Based on Topochemically Modified Cellulose, Papier (Heidelberg), 52:755-758 (1998).

Gemeiner, Immobilized Enzymes, Organelles and Cells, In Enzyme Engineering, Gemeiner, Ed., Ellis Horwood Series in Biochemistry and Biotechnology, Ellis Horwood Limited: West Sussex, England, pp. 158-179 (1992).

Gordon et al., Fused Organic Salts. 8. Properties of Molten Straight-Chain Isomers of Tetra-n-Pentylammonium Salts, J. Amer. Chem. Soc., 100(24):7445-7454 (1978).

Haleblian et al., Characterization of habits and crystalline modification of solids and their pharmaceutical applications, J. Pharm. Sci., 64:1269-1288 (1975).

Harkin et al., Lignification in Trees: Indication of Exclusive Peroxidase Participation, Science, 180:296-98 (1973).

Hartman et al., Saure Seifen, Z Angew Chem., 4:127-130 (1928).

Heinze et al., Unconventional Methods in Cellulose Functionalization, Prog. Polym. Sci., 26:1689-1762 (2001).

(56) References Cited

OTHER PUBLICATIONS

Hirayama, Rapid Confirmation and Revision of the Primary Structure of Bovine Serum Albumin by ESIMS and Frit-FAB LC/MS, Biochem. Biophys. Comm., 173:639-646 (1990).
Holbrey et al., The Phase Behaviour of 1-Alkyl-3-Methlimidazolium Tetrafluoroborates; Ionic Liquids and Ionic Liquid Crystals, J. Chem. Soc. Dalton Trans.,2133-2139 (1999).
Huddleston et al., Characterization and Comparison of Hydrophilic and Hydrophobic Room Temperature Ionic Liquids Incorporating the Imidazolium Cation, Green Chem., 3:156-164 (2001).
Huddleston et al., Room Temperature Ionic Liquids as Novel Media for 'Clean' Liquid-Liquid Extraction, Chem. Commun., 1765-1766 (1998).
Hudson et al., The Solubility of Unmodified Cellulose: A Crtique of the Literature, J. Macromol. Sci. Rev. Macromol. Chem., 18(1):1-82 (1980).
Husemann et al., Homogeneous Acetylation of Cellulose, Buletinul Institutului Politehnic Din Lasi, 1(1-2):47-51 (1970) (abstract).
Husemann et al., N-Athyl-pyridinium-chlorid als Losungmittel und Reaktionsmedium fur Cellulose, Die Makromolekulare Chemie, 128:288-291 (1969).
Illanes et al., Immobilization of Lactase and Invertase on Crosslinked Chitin, In Bioreactor Immobilized Enzymes and Cells, Moo-Young, Ed., Elsevier Applied Science: London, 233-249 (1998).
Illanes, Stability of Biocatalysts, Elec. J. Biotechnol., 2(1):1-9 (1999).
International Search Report for PCT/US2009/69652 dated Mar. 5, 2010.
International Search Report and Written Opinion for PCT/US2009/64105, issued Jan. 13, 2010.
International Search Report and Written Opinion for PCT/US2009/01066, issued Jun. 22, 2009.
International Search Report and Written Opinion for PCT/US2006/24863 issued Jan. 3, 2007.
International Search Report and Written Opinion for PCT/US2006/020941 issued May 30, 2006.
International Search Report and Written Opinion for PCT/US2005/010235, issued Jan. 3, 2007.
Jacobs et al., On a New Group of Bactericidal Substances Obtained from Hexamethylenetetramine, Proc. Nat. Acad. Sci. USA, 1:226-228 (1915).
Jacobs et al., The Quaternary Salts of Hexamethylenetetramine. I. Substituted Benzyl Halides and the Hexamethylenetetraminium Salts Derived Therefrom, J. Biol. Chem., 20:659-683 (1915).
Jacobs et al., The Bactericial Properties of the Quaternary Salts of Hexamethylenetetramine. III. The Relation Between Constitution and Bactericidal Action in the Quaternary Salts Obtained from Halogenacentyl Compounds, J. Exptl. Med., 23:577-599 (1916).
Katritzky et al., Strategies Toward the Design of Energetic Ionic Liquids: Nitro- and Nitrile-Substituted N,N'—Dialkylimidazolium Salts, New J. Chem., 30:349-358 (2006).
Katritzky et al., In Search of Ionic Liquids Incorporating Azolate Anions, Chem. Eur. J., 12:4630-4641 (2006).
Kilpeläinen et al., Dissolution of wood in ionic liquids, J. Agric. Food Chem., 55:9142-9148 (2007).
Al-Adhami et al., Immobilization of Wood-Rotting Fungi Laccases on Modified Cellulose and Acrylic Carriers, J. Process Biochemistry, 37:1387-1394 (2002).
Angell et al., Homogeneous Nucleation and Glass Transition Temperatures in Solutions of Li Salts in D2O and H2O. Doubly Unstable Glass Regions, J. of Physical Chemistry, 85:1461-1464 (1981).
Ast et al., Efficient Assembly of Peptomers on Continous Surfaces, Tetrahedron Lett., 40:4317-4318 (1999).
Axegård, The Future Pulp Mill-A Biorefinery? Presentation at 1st International Biorefinery Workshop, Washington, D.C., Jul. 20-21, 2005.
Bardeletti, Enzyme Immobilization on Polyethyleneimine-coated Magnetite Particles, Methodsin Biotech. I. Immobilization of Enzymes and Cells, pp. 133-141 (1997).

Benton et al., Effect of Room-Temperature Ionic Liquids as Replacements for Volatile Organic Solvents in Free-Radical Polymerization, Ionic Liquids, 818:125-133 (2002).
Biedron et al., Ionic Liquids as reaction Media for Polymeriazation Processes: Atom Transfer Radical Polymerization (ATRP) of Acrylates in Ionic Liquids, Polymer Int'l., 52(10):1584-1588 (2003).
Blankemeyer-Menge et al., Simultaneous Multiple Synthesis of Protected Peptide Fragments on 'Allyl'—Functionalized Cellulose Disc Supports, Tetrahedron Lett., 29:5871-5874 (1988).
Bonhôte et al., Hydrophobic, Highly Conductive Ambient-Temperature Molten Salts, Inorg. Chem.,35:1168-1178 (1996).
Bora et al., A Simple Method for Functionalization of Cellulose Membrane for Covalent Immoblization of Biomolecules, J. Membr. Sci., 250:215-222 (2005).
Brittain et al., Effects of Mechanical Processing on Phase Composition, J. Pharm. Sci. 91(7):1573-1580 (2002).
Browning et al., The Antiseptic Properties of the Amino Derivatives of Styryl and Anil AQuinoline, Proc. Royal Soc. London, 100(703):293-325 (1926).
Browning et al., Relationships between Antiseptic Action and Chemical Constitution with Special Reference to Compounds of the Pyridine, Quinoline, Acridine and Phenazine Series, Proc. Royal Soc. London, 93B:329-366 (1922).
Klinguer et al., Lipophilic quaternary ammonium salt acts as a mucosal adjuvant when co-administered by the nasal route with vaccine antigens, Vaccine, 19(30):4236-4244 (2001).
Krajewska, Application of Chitin- and Chitosan-based Materials for Enzyme Immobilizations: A Review, Enz. Microb. Techno., 35:126-139 (2004).
Lau et al., Dissolution of Candida Antarctica Lipase B in Ionic Liquids: Effects on Structure and Activity, Green Chem., 6:483-487 (2004).
Lee et al., Ionic Liquid-Mediated Selective Extraction of Lignin from wood leading to enhanced enzymatic cellulose hydrolysis, Biotech. and Bioeng., 102(5):1368-1376 (2009).
Leipner et al., Structural Changes of Cellulose Dissolved in Molten Salt Hydrates, Macromol Chem Phys, 201(15):2041-2049 (2000).
Liebert et al., Tailored Cellulose Esters: Synthesis and Structure Determination, Biomacromolecules, 6:333-340 (2005).
Linko et al., Cellulose Bead Entrapped Microbial Cells Biotechnical Applications, Enzyme Microb. Technol., 1:26-30 (1979).
Liu, Room temperature ionic liquids and their application in F&F industry, Flav. Frag. Cosmo (Xiangliao Xiangjing Huazhuangpin), 29(6):30-36 (2004).
Liu et al., Development of non-viral vectors for systemic gene delivery, J. Contr. Rel., 78:259-266 (2002).
Ma et al., Reverse Atom Transfer Radical Polymerization of Methyl Methacrylate in Room-Temperature Ionic Liquids, J. Polymer Sci. Pt. A—Polymer Chem., 41:143-151 (2003).
MacFarlane, Physical aspects of vitrification in aqueous solutions, Cryobiology, 24:181-195 (1987).
MacFarlane, Session 4—Vitrification vs. freezing of aqueous solutions: Physical and Biological Factors, Cryobiology, 23:559-560 (1986).
MacFarlane, Devitrification in glass-forming aqueous solutions, Cryobiology, 23:230-244 (1986).
MacFarlane et al., Conductivity and dielectric relaxation in calcium nitrate tetrahydrate and sodium thiosulfate pentahydrate near T9, J. of Physical Chemistry, 89:5849-5855 (1985).
MacFarlane, Abstracts of papers presented at the Twenty-Second Annual Meeting of the Society for Cryobiology, Cryobiology, 22:601-640 (1985).
MacFarlane et al., Emulsion techniques for the study of glass formation. 2. Low melting point salt hydrates, J. of Physical Chemistry, 88:4779-4781 (1984).
MacFarlane et al., Homogeneous nucleation and growth of ice from solutions. TTT curves, the nucleation rate, and the stable glass criterion, J. of Chemical Physics, 79(8):3921-3927 (1983).
MacFarlane et al., Direct observation of time-temperature-transformation curves for crystallization of Ice from solutions by a homogeneous mechanism J. of Physical Chemistry, 87:1094-1095 (1983).

(56) References Cited

OTHER PUBLICATIONS

Maia et al., Cellulose Organic Solvents. 1. The Structure of Anhydrous N-Methylmorpholine N-Oxide and N-Methylmorphline N-Oxide Monohydrate, Acta Cryst., B37:1858-1862 (1981).
Mais et al., Modification of Cellulose Using Cellulose p-Toluene-Sulfonates as Intermediates, Zeszyty Naukowe Politechniki Slaskiej Chemm., 140:121-125 (1999).
Manangeeswaran et al., Degradation of indulin, a kraft pine lignin, by Serratia marcescens, J. Environ. Sci. Health, Part B: Pesticides, Food Contaminants, and Agricultural Wastes, 42(3):321-327 (2007).
Marson et al., A Novel, Efficient Procedure for Acylation of Cellulose Under Homogeneous Solution Conditions, J. Appl. Polymer Sci., 74:1355-1360 (1999).
Martin et al., Anisotropic magnetism in field-structured composites, Phys. Rev. E., 61(3):2818-2830 (2000).
Mazurkiewicz et al., Conducting Polymer Electrochemistry in Ionic Liquids, Synthetic Metals, 135:31-32 (2003).
Morissette et al., Elucidation of crystal form diversity of the HIV protease inhibitor ritonavir by high-throughput crystallization, Proc. Natl. Acad. Sci. USA, 100(5):2180-2184 (2003).
Nara et al., Lipase-Catalysed Polyester Synthesis in 1-Butyl-3-Methylimidazolium Hexafluorophosphate Ionic Liquid, Tetrahedron Lett, 44:1371-1373 (2003).
Ngo et al., Thermal Properties of Imidazolium Ionic Liquids, Thermochimica Acta, 357-358:97-102 (2000).
Oertel, Novel hard to wash-out water soluble wood protecting agents and their applications, Holztechnologie, 6(4):243 (1965).
Ohno et al., A New Type of Polymer Gel Electrolyte: Zwitterionic Liquid/Polar Polymer Mixture, Electrochimica Acta, 48:2079-2083 (2003).
Okamato et al., Synthesis, Spectra, and Reactions of N-Triphenylmethylpyridinium Salts. Reactions of Triphenylmethyl Chlordie with Pyridine Under High Pressure, J. Org. Chem., 35(11):3752-3756 (1970).
Padhye et al., Cellulose Degradation in Xanthate Process, J. App. Polymer Sci. 36:1475-1478 (1988).
Perrier et al., Reversible Addition—Fragmentation Chain Transfer Polymerization of Methacrylate, Acrylate and Styrene Monomers in 1-Alkyl-3-Methylimidazolium Hexfluorophosphate, European Polymer J., 39(3):417-422 (2003).
Pu et al., Ionic liquid as a green solvent for lignin, J. Wood Chem. Technol, 27:23-3 (2007).
Ren et al., Synthesis of 1-Allyl-3-Methylimidazolium-Based Room Temperature Ionic Liquid and Preliminary Study of its Dissolving Cellulose, Acta Polymerica Sinica, 3448-51 (2003) (abstract).
Reutzel-Edens et al., Anhydrates and hydrates of olanzapine: Crystallization, solid-state characterization, and structural relationships, Crystal Growth & Design, 3:897-907 (2003).
Rogers et al., Ionic Liquids—Solvents of the Future? Science, 302:792-793 (2003).
Sakai, Determination of Pore Size and Pore Size Distribution, J. Membr. Sci., 96:91-130 (1994).
Shriver et al., Inorganic Chemistry, W. H. Freeman & Co., New York, pp. 406-407 (1990).
Snedden et al., Cross-Linked Polymer-Ionic Liquid Composite Materials, Macromolecules, 36(12):4549-4556 (2003).
Stöllner et al., Activation of Cellulose Membranes with 1,1'-Carbonyldiimidazole or 1-Cyano-4-Dimethylaminopyridinium Tetrafluoroborate as a Basis for the Development of Immunosensors, Anal. Biochem., 304:157-165 (2002).
Suarez et al., Synthesis and Physical-Chemical Properties of Ionic Liquids Based on 1-n-Butyl-3-Methylimidazolium Cation, J. Chimsua. Phys., 95:1626-1639 (1998).
Sullivan, Solvents by Design, Innovations in Pharmaceutical Technology, 20:75-77 (2006).
Sun et al. Magnetite-Embedded Cellulose Fibers Prepared From Ionic Liquid, J. Mat. Chem., 18:283-290 (2008).
Supplemental Search Report for EP4757863, issued May 12, 2009.
Swatloski et al., Dissolution of Cellulose with Ionic Liquids, J. Am. Chem. Soc., 124:4974-4975 (2002).
Swatloski et al., Ionic Liquids for the Dissolution and Regeneration of Cellulose, in Molten Salts XIII: Proceedings of the International Symposium, Trulove, P.C., DeLong, H.C., Mantz, R.A., Stafford, G.R., Matsunaga, M., Eds., The Electrochemical Society: Pennington, NJ, 19:155-164 (2002).
Tiller et al., A Novel Efficient Enzyme-Immobilization Reaction on NH2 Polymers by Means of L-Ascorbic Acid, Biotechnol. Appl. Biochem., 30:155-162 (1999).
Turner et al., Production of Bioactive Cellulose Films Reconstituted from Ionic Liquids, Biomacromolecules, 5:1379-1384 (2004).
Turner, Immobilization of Biocatalysts Using Novel IL-Reconstituted Cellulosic Support Materials, presentation on Apr. 19, 2005.
Visser et al., Task Specific Ionic Liquids for the Extraction of Metal Ions from Aqueous Solutions, Chem. Commun., 135-136 (2001).
Office Action for IL Patent Application No. 1224583 dated Jan. 8, 2014.
Freemantle, Eyes on ionic liquids, Chem. Eng. News, 78(2):37-50 (2000).
Matsumoto et al., Room temperature ionic liquids based on small aliphalic ammonium cations and asymmetric amide anions, Chem. Comm. 1726-1727 (2002).
Office Action for JP Patent Application No. 10-2008-7010190 dated Nov. 28, 2013 (English Translation).
Office Action for KR Patent Application No. 10-2008-7010190 dated Nov. 28, 2013 (English Translation).
First Office Action, dated Jun. 20, 2014, received in connection with CN Application No. 2013101661859. (English translation).
Examination Report, dated Sep. 18, 2014, received in connection with EP Application No. 11817120.6. (English translation).
Examination Report, dated Aug. 13, 2014, received in connection with IN Application No. 3782/DELNP/2008. (English translation).
Office Action, dated Sep. 4, 2014, received in connection with JP Application No. 2008534766. (English translation).
Office Action, dated Sep. 22, 2014, received in connection with KR Application No. 1020137019299. (English translation).
Final Office Action, dated Aug. 26, 2014, received in connection with U.S. Appl. No. 13/816,598.
Office Action from Canada Patent Office for Application No. 2,867,194 dated Nov. 24, 2014.
MacLachlan, Glufosinate Ammonium, Department of Agriculture, Fisheries and Forestry, 937-1182, accessed on Jan. 29, 2015.

* cited by examiner

DUAL FUNCTIONING IONIC LIQUIDS AND SALTS THEREOF

CROSS REFERENCE TO RELATED APPLICATIONS

This application is a 371 U.S. National Phase of International Application PCT/US2009/069652, filed Dec. 29, 2009, which claims the benefit of priority to Provisional Application Ser. No. 61/141,168 filed on Dec. 29, 2008, the entire disclosure of which is incorporated herein by reference.

FIELD

Disclosed herein are ionic liquid compositions comprising active pharmaceutical, biological, and nutritional compounds, and methods of use. Further disclosed are compositions of matter including liquid ion pairs alone or in solution and their use; compositions of ionic liquids that are 'solvated,' for example, 'hydrated' and their uses.

BACKGROUND

Polymorphism is the ability of a substance to exist in two or more crystalline forms that have a different arrangement and/or conformation of molecules in a crystalline lattice (see e.g., Chawla and Bansal, *CRIPS* 2004, 5(1):9-12; Bernstein, "Polymorphism in Molecular Crystals," *IUCR Monographs on Crystallography* 14, Oxford Science Publications, 2002, pp. 1-28, 240-256). It has been estimated that a large number of pharmaceuticals exhibit polymorphism. For example, 70% of barbiturates, 60% of sulfonamides, and 23% of steroids are believed to exist in different polymorphic forms or "polymorphs" (Haleblian et al., *J Pharm Sci* 1975, 64:1269-1288).

In some cases, when crystals of a compound are forming (e.g., crystallizing from a solution), solvent molecules may become entrapped or bound within the crystal lattice. The presence of the entrapped solvent molecules may affect the three-dimensional crystal lattice that eventually crystallizes. The occurrence of a compound (target molecule) crystallizing in different three-dimensional lattices based upon the presence of solvent molecules has been termed "pseudo-polymorphism." Akin to polymorphs, such "pseudo-polymorphs," also known as "solvates" (or "hydrates" when the solvent is water), are crystalline solids containing either stoichiometric (i.e., whole number ratios of target molecules to solvent molecules) or non-stoichiometric (i.e., non-whole number ratios of target molecules to solvent molecules) amounts of a solvent incorporated within the crystal structure. In general, different crystalline forms of molecules (e.g., pharmaceutical compounds) can exist in the same or different hydrated or solvated states.

The existence of various polymorphs or pseudo-polymorphs can greatly affect a pharmaceutical's performance since each form can have different physical and chemical properties. For example, one particular polymorph pseudo-polymorph may be more bioavailable, more stable (e.g., longer shelf life), or more easily formulated or tableted than another polymorph. Similarly, one polymorph pseudo-polymorph may be more active or less toxic than another. Some specific examples of the dramatic difference that can exist between various pharmaceutical polymorphs are described in, e.g., Brittain et al., *J Pharm Sci* 2002, 91:1573-1580 and Morissette et al., *Proc Natl Acad Sci USA* 2003, 100:2180-2184.

The effects of polymorphism and pseudo-polymorphism on quality and performance of a drug is widely recognized. The exact solid state polymorph (or pseudo-polymorph) of a compound determines its physical properties such as dissolution rate, solubility, bioavailability, crystal habit, mechanical strength, etc. (Datta et al., *Nature Reviews—Drug Discovery*, 2004, 3:42-57). The delivery of an exact dosage in manufacture and the manufacturing process itself often depend on which of several possible polymorphs or pseudo-polymorphs are present.

The variation in properties among different polymorphs (or pseudo-polymorphs) usually means that one crystalline form is desired or preferred over other forms. Obtaining a particular form can be difficult, however. Typically, researchers have to experiment with a multitude of variables in crystallization conditions, such as aqueous solvent mixtures, amount of water, amount of target compound, relative humidity, temperature of incubation, incubation time, etc., in a process characterized by trial and error. Further, the search for salts of crystalline forms (usually sought after to control dissolution rate and solubility) can require extensive experimentation. Each salt of a drug or each different solvent used to crystallize the drug or a salt of the drug may lead to polymorphs or pseudo-polymorphs that have to be fully investigated and that have different properties (see e.g., Reutzel-Edens et al., "Anhydrates and hydrates of olanzapine: Crystallization, solid-state characterization, and structural relationships," *Crystal Growth & Design*, 2003, 3:897-907).

Another common problem that exists with many pharmaceuticals, agrochemicals, nutraceuticals etc. is low solubility. Low solubility can make formulating a particular compound difficult, and generally low solubility translates into low bioavailability. Much research is conducted on finding ways to improve a compound's solubility and availability. Typically methods include complex delivery devices and chemical modifications of the drug.

Polymorphism and pseudo-polymorphism is difficult to predict, i.e., there is a relationship between the crystalline state of a compound and its chemical properties (e.g., dissolution rate, solubility), biological properties (e.g., bioavailability, pharmacokinetics), mechanical and physical properties, and manufacturing processes. In some instances polymorphs and pseudo-polymorphs can interconvert. Moreover, there is a need for compositions that can manifest their base property, for example, their pharmacological properties, while having controllable and/or adjustable chemical, biological, and physical properties, that the formulator can "tune" to the desired properties while at the same time avoiding any undesirable polymorphism. In addition, there is a need for compounds having these properties which have modifiable dissolution and solubility properties. As such, there is further needed methods of preparing and using compositions having these controllable properties. Further, there is a need for methods of converting compounds that are difficult to solubilize into a form that allows for increased solubility. Disclosed herein are compositions and methods that provide for the above compounds, compositions, and methods.

SUMMARY

In accordance with the purposes of the disclosed materials, compounds, compositions, devices, and methods, as embodied and broadly described herein, the disclosed subject matter, in one aspect, relates to compounds and compositions and methods for preparing and using such compounds and compositions. In a further aspect, the disclosed subject matter relates to ionic liquid compositions that can be used for or in biological, pharmaceutical, nutritional, cosmetic, industrial, and commercial compositions. Methods for making the disclosed ionic liquid compositions are also disclosed. Also disclosed are methods of preparing ionic liquid compositions of active pharmaceutical, biological, nutritional, and energetic ingredients. Also the disclosed are methods of using the compositions described herein to overcome polymorphism, overcome solubility and delivery problems, to control release rates, add functionality, enhance efficacy, and improve ease of use and manufacture. Also disclosed is the use of multiple functional co-ionic liquids with excess of any free base or any free acid in equilibrium with cation or anion that are composed of active pharmaceutical, biological, nutritional, or energetic ingredients. The present disclosure is based upon the discovery that the physico-chemical properties of common pharmaceutical salts can be modified by addition of the corresponding protic acid or base to form new ionic liquid species of the type $[B^1HB^2]A$ or $B[A^1HA^2]$.

Also disclosed is a process for preparation via solvent-free methods, e.g. grinding or reaction in molten state. The process can include addition of a acid or base to a common pharmaceutical active salt or by direct solvent-free reaction of acid with base in a ratio other than 1:1 to form co-ionic liquids of the type $[B^1HB^2]A$ or $B[A^1HA^2]$.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

Further disclosed is the use of ionic liquids for immobilization, delivery, and controlled release of pharmaceutically active neutral compounds. This use is based upon the discovery that neutral active compounds, especially pharmaceuticals, can be covalently linked with ionic structural moiety and turned into an ionic liquid by appropriate choice of the counter ion. The ionic liquid acts not only as support for the active compounds, being able to store pharmaceuticals in inactive form but also allow a simple tuning of physical properties like solubility, bioavailability, lipophilicity or control over polymorphism as well as the control over release kinetics of the active compound.

Yet further discloses is a synthetic methodology to transfer neutral compounds into salts, wherein the active compound can be of either positive or negative charge, with the possibility to form dual functioning salts by introduction of a second, pharmaceutically or biologically active counterion.

Further described herein is a method for the immobilization of volatile fragrance and flavor compounds in the form of ionic liquids of neglible volatility for storage as well for controlled and prolonged release of the fragrance- or flavor compounds under defined conditions such as temperature, or pH value.

DETAILED DESCRIPTION

Figure 1:
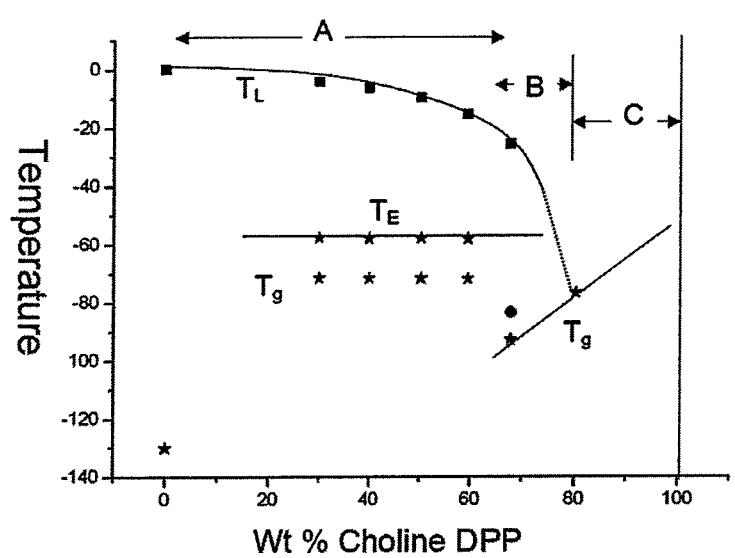
FIG. 1 depicts the binary phase diagram for choline DPP as example for ionic liquid diluates.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., microorganism growth or survival). It is understood that this is typically in relation to some standard or expected value, in other words it is relative, but that it is not always necessary for the standard or relative value to be referred to. For example, "reduces bacteria growth" means lowering the amount of bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, break-down, or eliminate a particular characteristic or event (e.g., microorganism growth or survival). The term "control" is used synonymously with the term "treat."

By "antimicrobial" is meant the ability to treat or control (e.g., reduce, prevent, inhibit, break-down, or eliminate) microorganism growth or survival at any concentration. Similarly, the terms "antibacterial," "antiviral," and "antifungal" respectively mean the ability to treat or control (e.g., reduce, prevent, inhibit, break-down, or eliminate) bacterial, viral, and fungal growth or survival at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both (e.g., zwitterions) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, etc.

The term "anion" is a type of ion and is included within the meaning of the term "ion". An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion". A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$D^1$," "$D^2$," "$D^3$," and "$D^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as $-OD^1$ where $D^1$ is alkyl as defined above.

The term "alkenyl" as used herein is a hydrocarbon group of from 2 to 24 carbon atoms with a structural formula containing at least one carbon-carbon double bond. Asymmetric structures such as $(D^1D^2)C=C(D^3D^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $ND^1D^2D^3$, where $D^1$, $D^2$, and $D^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$D^1$ or —C(O)O$D^1$, where $D^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $D^1OD^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $D^1C(O)D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiD^1D^2D^3$, where $D^1$, $D^2$, and $D^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —$S(O)D^1$, —$S(O)_2D^1$, —$OS(O)_2D^1$, or —$OS(O)_2OD^1$, where $D^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. Throughout this specification "S(O)" is a short hand notation for S=O.

The term "sulfonyl" is used herein to refer to the sulfo-oxo group represented by the formula —$S(O)_2D^1$, where $D^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "sulfone" as used herein is represented by the formula $D^1S(O)_2D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula $D^1S(O)D^2$, where $D^1$ and $D^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "bioactive property" is any local or systemic biological, physiological, or therapeutic effect in a biological system. For example, the bioactive property can be the control of infection or inflammation, enhancement or suppression of growth, action as an analgesic, anti-viral, pesticidal, herbicidal, or nutrientional action, etc. Many examples of bioactive properties are disclosed herein.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Materials and Compositions

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the active pharmaceutical ingredients, pesticides, herbicides, and other biological agents disclosed herein can be obtained from commercial sources.

In one aspect, disclosed herein are ionic liquid compositions. The term "ionic liquid" has many definitions in the art, but is used herein to refer to salts (i.e., compositions comprising cations and anions) that are liquid at a temperature of at or below about 150° C. That is, at one or more temperature ranges or points at or below about 150° C. the disclosed ionic liquid compositions are liquid; although, it is understood that they can be solids at other temperature ranges or points. Since the disclosed ionic liquid compositions are liquid, and thus not crystalline solids, at a given temperature, the disclosed compositions do not suffer from the problems of polymorphism associated with crystalline solids.

The use of the term "liquid" to describe the disclosed ionic liquid compositions is meant to describe a generally amorphous, non-crystalline, or semi-crystalline state. For example, while some structured association and packing of cations and anions can occur at the atomic level, the disclosed ionic liquid compositions have minor amounts of such ordered structures and are therefore not crystalline solids. The compositions disclosed herein can be fluid and free-flowing liquids or amorphous solids such as glasses or waxes at a temperature at or below about 150° C. In particular examples disclosed herein, the disclosed ionic liquid compositions are liquid at the body temperature of a subject.

Further, the disclosed ionic liquid compositions are materials composed of at least two different ions; each of which can independently and simultaneously introduce a specific characteristic to the composition not easily obtainable with traditional dissolution and formulation techniques. Thus, by providing different ions and ion combinations, one can change the characteristics or properties of the disclosed ionic liquid compositions in a way not seen by simply preparing various crystalline salt forms. Examples of characteristics that can be controlled in the disclosed compositions include, but are not limited to, melting, solubility control, and rate of dissolution. It is this multi-nature/functionality of the disclosed ionic liquid compositions which allows one to fine-tune or design in very specific desired material properties.

It is further understood that the disclosed ionic liquid compositions can include solvent molecules (e.g., water); however, these solvent molecules should not be present in excess in the sense that the disclosed ionic liquid compositions are dissolved in the solvent, forming a solution. That is, the disclosed ionic liquid compositions contain no or minimal amounts of solvent molecules that are free and not bound or associated with the ions present in the ionic liquid composition. Thus, the disclosed ionic liquid compositions can be liquid hydrates or solvates, but not solutions.

Ionic liquids have been of general interest because they are environmentally-friendly alternatives to organic solvents for various chemical processes, e.g., liquid/liquid extractions, catalysis, separations, and electrochemistry. Ionic liquids have also become popular alternative media for chemical synthesis because of their low volatility and low toxicity. See e.g., Wasserscheid and Keim, *Angew Chem Int Ed Engl,* 2000, 39:3772; and Wasserscheid, "Ionic Liquids in Synthesis," $1^{st}$ Ed., Wiley-VCH, 2002. Further, ionic liquids can reduce costs, disposal requirements, and hazards associated with volatile organic compounds. Other exemplary properties of ionic liquids are high ionic conductivity, non-volatility, non-flammability, high thermal stability, wide temperature for liquid phase, highly solvability, and non-coordinating. For a review of ionic liquids see, for example, Welton, *Chem. Rev.* 1999, 99:2071-2083; and Carlin et al., Advances in Nonaqueous Chemistry, Mamantov et al. Eds., VCH Publishing, New York, 1994.

The specific physical properties (e.g., melting point, viscosity, density, water solubility, etc.) of ionic liquids are determined by the choice of cation and anion, as is disclosed more fully herein. As an example, the melting point for an ionic liquid can be changed by making structural modifications to the ions or by combining different ions. Similarly, the particular chemical properties (e.g., bioactivity, toxicity, pharmacokinetics, etc.), can be selected by changing the constituent ions of the ionic liquid.

The ionic liquid compositions disclosed herein are comprised of at least one kind of anion and at least one kind of cation. The at least one kind of cation, the at least one kind of anion, or both can be a pharmaceutical active, a pesticidal active, a herbicidal active, a food additive, a nutraceutical, or the like, including any combination thereof, as is disclosed herein. It is contemplated that the disclosed ionic liquid compositions can comprise one kind of cation with more than one kind of anion (e.g., 2, 3, 4, 5, 6, 7, 8, 9, 10, or more different kinds of anions). Likewise, it is contemplated that the disclosed ionic liquid compositions can comprise one kind of anion with more than one kind of cation (e.g., 2, 3, 4, 5, 6, 7, 8, 9, 10, or more different kinds of cations). Further, the disclosed ionic liquids can comprise more than one kind of anion (e.g., 2, 3, 4, 5, 6, 7, 8, 9, 10, or more different kinds of anions) with more than one kind of cation (e.g., 2, 3, 4, 5, 6, 7, 8, 9, 10 or more different kinds of cations). Specific examples include, but are not limited to, one kind of cation with 1, 2, 3, 4, 5, 6, 7, 8, 9, 10, or more kinds of anions, 2 kinds of cations with 1, 2, 3, 4, 5, 6, 7, 8, 9, 10, or more kinds of anions, 3 kinds of cations with 1, 2, 3, 4, 5, 6, 7, 8, 9, 10, or more kinds of anions, 4 kinds of cations with 1, 2, 3, 4, 5, 6, 7, 8, 9, 10, or more kinds of anions, 5 kinds of cations with 1, 2, 3, 4, 5, 6, 7, 8, 9, 10, or more kinds of anions, 6 kinds of cations with 1, 2, 3, 4, 5, 6, 7, 8, 9, 10, or more kinds of anions, 7 kinds of cations with 1, 2, 3, 4, 5, 6, 7, 8, 9, 10, or more kinds of anions, 8 kinds of cations with 1, 2, 3, 4, 5, 6, 7, 8, 9, 10, or more kinds of anions, 9 kinds of cations with 1, 2, 3, 4, 5, 6, 7, 8, 9, 10, or more kinds of anions, 10 kinds of cations with 1, 2, 3, 4, 5, 6, 7, 8, 9, 10, or more kinds of anions, or more than 10 kinds of cations with 1, 2, 3, 4, 5, 6, 7, 8, 9, 10, or more kinds of anions.

Other specific examples include, but are not limited to, one kind of anion with 1, 2, 3, 4, 5, 6, 7, 8, 9, 10, or more kinds of cations, 2 kinds of anions with 1, 2, 3, 4, 5, 6, 7, 8, 9, 10, or more kinds of cations, 3 kinds of anions with 1, 2, 3, 4, 5, 6, 7, 8, 9, 10, or more kinds of cations, 4 kinds of anions with 1, 2, 3, 4, 5, 6, 7, 8, 9, 10, or more kinds of cations, 5 kinds of anions with 1, 2, 3, 4, 5, 6, 7, 8, 9, 10, or more kinds of cations, 6 kinds of anions with 1, 2, 3, 4, 5, 6, 7, 8, 9, 10, or more kinds of cations, 7 kinds of anions with 1, 2, 3, 4, 5, 6, 7, 8, 9, 10, or more kinds of cations, 8 kinds of anions with 1, 2, 3, 4, 5, 6, 7, 8, 9, 10, or more kinds of cations, 9 kinds of anions with 1, 2, 3, 4, 5, 6, 7, 8, 9, 10, or more kinds of cations, 10 kinds of anions with 1, 2, 3, 4, 5, 6, 7, 8, 9, 10, or more kinds of cations, or more than 10 kinds of anions with 1, 2, 3, 4, 5, 6, 7, 8, 9, 10, or more kinds of cations.

In addition to the cations and anions, the ionic liquid compositions disclosed herein can also contain nonionic species, such as solvents, preservatives, dyes, colorants, thickeners, surfactants, viscosity modifiers, mixtures and combinations thereof and the like. However, the amount of such nonionic species is typically low (e.g., less than about 10, 9, 8, 7, 6, 5, 4, 3, 2, or 1 wt. % based on the total weight of the composition). In some examples described herein, the disclosed ionic liquid compositions are neat; that is, the only materials present in the disclosed ionic liquids are the cations and anions that make up the ionic liquid compositions. It is understood, however, that with neat compositions, some additional materials or impurities can sometimes be present, albeit at low to trace amounts (e.g., less than about 10, 9, 8, 7, 6, 5, 4, 3, 2, or 1 wt. % based on the total weight of the composition).

The disclosed ionic liquid compositions are liquid at some temperature range or point at or below about 150° C. For example, the disclosed ionic liquids can be a liquid at or below about 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, −1, −2, −3, −4, −5, −6, −7, −8, −9, −10, −11, −12, −13, −14, −15, −16, −17, −18, −19, −20, −21, −22, −23, −24, −25, −26, −27, −28, −29, or −30° C., where any of the stated values can form an upper or lower endpoint when appropriate. In further examples, the disclosed ionic liquids can be liquid at any point from about −30° C. to about 150° C., from about −20° C. to about 140° C., −10° C. to about 130° C., from about 0° C. to about 120° C., from about 10° C. to about 110° C., from about 20° C. to about 100° C., from about 30° C. to about 90° C., from about 40° C. to about 80° C., from about 50° C. to about 70° C., from about −30° C. to about 50° C., from about −30° C. to about 90° C., from about −30° C. to about 110° C., from about −30° C. to about 130° C., from about −30° C. to about 150° C., from about 30° C. to about 90° C., from about 30° C. to about 110° C., from about 30° C. to about 130° C., from about 30° C. to about 150° C., from about 0° C. to about 100° C., from about 0° C. to about 70° C., from about 0° to about 50° C., and the like.

Further, in some examples the disclosed ionic liquid compositions can be liquid over a wide range of temperatures, not just a narrow range of, say, 1-2 degrees. For example, the disclosed ionic liquid compositions can be liquids over a range of at least about 4, 5, 6, 7, 8, 9, 10, or more degrees. In other example, the disclosed ionic liquid compositions can be liquid over at least about a 11, 12, 13, 14, 15, 16, 17, 18, 19, 20, or more degree temperature range. Such temperature ranges can begin and/or end at any of the temperature points disclosed in the preceding paragraph.

In many examples disclosed herein the disclosed ionic liquid compositions are liquid at the temperature at which they will be used or processed. For example, many of the disclosed ionic liquid compositions can be used for therapeutic or nutritional purposes in a subject. In this case, the disclosed ionic liquid compositions can be liquid at the subject's body temperature (e.g., about 37° C. for a human). Other examples include compositions that can be used as herbicides or pesticides, which are liquid at the temperature of their use (e.g., ambient temperature). In still other examples, the disclosed compositions can be liquid at the temperature at which they are formulated or processed.

It is understood, however, that the disclosed ionic liquid compositions can, though need not, be solubilized, and solutions of the disclosed ionic liquids are contemplated herein. Further, the disclosed ionic liquid compositions can be formulated in an extended or controlled release vehicle, for example, by encapsulating the ionic liquids in microspheres or microcapsules using methods known in the art. Still further, the disclosed ionic liquid compositions can themselves be solvents for other solutes. For example, the disclosed ionic liquids can be used to dissolve a particular nonionic or ionic pharmaceutical active. These and other formulations of the disclosed ionic liquids are disclosed elsewhere herein.

In some examples, the disclosed ionic liquids are not solutions where ions are dissolved in a solute. In other examples, the disclosed ionic liquid compositions do not contain ionic exchange resins. In still other examples, the disclosed ionic liquids are substantially free of water. By substantially free is meant that water is present at less than about 10, 9, 8, 7, 6, 5, 4, 3, 2, 1, 0.5, 0.25, or 0.1 wt. %, based on the total weight of the composition.

The disclosed ionic liquid compositions can be prepared by methods described herein. Generally, the particular cation(s) and anion(s) used to prepare the disclosed ionic liquids are selected as described herein. Then, with the particular cation(s) and anion(s) in hand, they can be combined, resulting in ionic liquid compositions as disclosed herein. Additionally, the method for the preparation of the disclosed ionic liquid compositions can include the reaction in which two neutral species: an anion precursor (e.g., in the form of an inorganic acid, carboxylic organic acid, non-carboxylic acid, or zwitterion species) and a cation precursor (e.g., inorganic base, organic base, zwitterion species) are combined resulting in ionic liquid compositions as disclosed herein.

Providing ions used to prepare the disclosed ionic liquids depends, in one aspect, on the desired properties of the resulting ionic liquid composition. As described herein, the disclosed ionic liquid compositions can have multiple desired properties, which, at least in part, come from the properties of the cation(s) and/or anion(s) used to prepare the ionic liquid. Thus, to prepare the disclosed ionic liquids, one or more kinds of cations with a desired property(ies) are provided. One or more kinds of anions with a desired property(ies) that is similar or different to that of the cation(s) can likewise be provided. Of course, providing a desired anion(s) and cation(s) can be done in any order, depending on the preference and aims of the practitioner. For example, a particular cation(s) can be provided and then a particular anion(s) can be provided. Alternatively, a particular anion(s) can be provided and then a particular cation(s) can be provided. Further, the cation(s) and anion(s) can be provided simultaneously.

As noted, providing a suitable ion can be based on selecting an ion that possesses a property that is desired (e.g., the ion has a property that is desired to be possessed by the resulting ionic liquid). Examples of properties that could be desired in a suitable cation and/or anion (and thus the ionic liquid made therefrom) include, but are not limited to, biological, therapeutic, prophylactic, nutritional, pesticidal, and/or herbicidal activity. Inertness, taste, viscosity modulation, solubility modulation, stability, and toxicity are other properties of a given ion that could be desired and considered. While more specific properties are disclosed elsewhere herein, the disclosed methods and compositions are not limited to any particular combination of properties, as such will depend on the preferences and goals of the practitioner.

Typically, the desired properties of the cation(s) and anion(s) will be different or complimentary to one another. In this way, the resulting ionic liquid can possess multiple desired properties: those properties imparted by the cation(s) and those imparted by the anion(s). In other words, some or all of the ions present in the disclosed ionic liquids can independently and simultaneously introduce a specific functionality or property to the disclosed ionic liquid compositions. It is this multiple functionality characteristic that can allow one to fine-tune or design very specific physical, chemical, and bioactive properties in the disclosed ionic liquid compositions. Additional functionality can be obtained by using the disclosed ionic liquid compositions as solvents to dissolve a solute(s) with another desired property, thus resulting in a solution where the ions of the ionic liquid as well as the solute contribute desired properties to the composition. General and specific examples of various combinations of ions and their associated properties are disclosed herein.

In some particular examples, one or more ions in the disclosed ionic liquid composition (e.g., the anions, cations, or both) can be a pharmaceutical active, e.g., an existing drug that is ionic or that can be made ionic. Many drugs exist naturally or at physiological conditions as an ion, or they can be converted to ions via simple chemical transformations (e.g., alkylation, protonation, deprotonation, etc.). As such, these drugs can be used to prepare an ionic liquid composition as disclosed herein. Such drugs can possess any therapeutic or prophylactic activity, many of which are described herein. Combining such drugs with other ions to prepare an ionic liquid, as is disclosed herein, can result in the modification and/or enhancement of the drug's properties. For example, a first drug ion with a given property can be combined with an oppositely charged second ion with another property to effect the controlled release, controlled delivery, biological impact, taste, physical properties (stability, solubility, toxicity, melting point, etc.), or to overcome polymorphism in the first drug ion. In this way, new drug compositions can be created by forming ionic liquids with functionality crafted into the combination of the ions, as disclosed herein.

As another example, the first drug ion may be combined with a second drug ion that has properties complimentary to the first. Examples of this can include, but are not limited to, an ion having anesthetic properties being combined with an ion having antibacterial properties, an ion having anesthetic properties being combined with an ion having coagulation properties, or an ion having coagulation properties being combined with an ion having antibacterial properties. Ionic liquids resulting from such combinations could find uses in wound repair, for example. Still other examples of desirable combination include ions having therapeutic or prophylactic efficacy being combined with ions having taste enhancement properties (i.e., taste modifiers). Ionic liquids resulting from this combination can be useful in enhancing the taste and palatability of medicines. Still further examples can include two differently charged ions each with similar uses but with different mechanisms of action. Specific examples of such combinations can include, but are not limited to, combinations of ions with antineoplastic properties or antiviral properties. Ionic liquids prepared from such ion combinations can be useful as drug "cocktails," where two or more bioactive agents are present in a single ionic liquid combination.

According to the methods and compositions disclosed herein, ion identification and combination, as disclosed herein, can involve any ion, not just ionic drugs, as long as the combination results in an ionic liquid. For example, ions that have pesticidal properties can be combined with oppositely charged ions having pesticidal, herbicidal, antimicrobial properties, and the like. In other examples, ions with antibacterial properties can be combined with oppositely charges ions that have preservative properties, taste modifiers, etc. In still other examples, an ion with one therapeutic or prophylactic property can be combined with another therapeutic or prophylactic ion. As should be appreciated, the various combinations of ions according to the disclosed methods are numerous, and depend only on the desired combination of properties and whether the resulting ion combination is an ionic liquid as defined herein.

Specific examples of properties that can be exhibited by the disclosed compositions include antibacterial, FDA approved dyes, anti-acne, antibiotic, UV blocker, wetting agents, preservative, emollient, anti-inflammatory, and vitamin.

Ionic Liquid Immobilized Fragrances

Fragrance and flavor formulations suffer from limited lifetime because their constituents evaporate, are degrading or lost during storage. Perfumes in consumer products tend to fade by evaporation, oxidation, chemical degradation or interaction with other ingredients. The flavor industry has addresses the issue of performance loss of flavors by developing specific delivery systems. At the present time, sustained release techniques for flavor and fragrance delivery present in literature are usually based on encapsulation either in hydrophilic matrices, via spray drying, granulation and spray-coating, encapsulation by coacervation and interfacial polymerization and the use of colloidal carriers for the application in aqueous products (Quellet et al. *Chimia* 2001, 55:421-428).

The use of ionic liquid in fragrance and flavor industry is mainly dealing with solvent applications for the synthesis of fragrance and flavor materials in ionic liquids or with the extraction of naturals (Sullivan, N. *Innovations in Pharmaceutical Technology* 2006, 20:75-77).

For example, Forsyth et al. investigated the utilization of ionic liquid solvents for the synthesis of lily-of-the-valley fragrance and fragrance intermediate Lilial (Forsyth et al., *J. Mol. Cat. A*. 2005, 231:61-66). The role of ionic liquids in consumer products and fragrances is comparingly less explored (Davey, *Perf. Flav.* 2008, 33:34-35; Liu, *Flav. Frag. Cosm.* (*Xiangliao Xiangjing Huazhuangpin*) 2004, 29:30-36). Creavis noted that the rate of evaporation of a perfume could be slowed using an ionic liquid as fixative (Petrat et al. US 2006/0166856; Creavis AG DE 10337579A1). Examples include a chypre accord, a musk base and a rose composition with increased fiber substantivity compared to the same composition without the ionic liquid. The modification of textile surfaces, optionally adding a benefit agent which includes a perfume followed by removal of the ionic liquid was described by Procter and Gamble. (US 20060090271, US 20060090777, EP 1807497). Benefit agent delivery systems comprising ionic liquids and their uses in detergent compositions have also been reported. (Price et al. US2006094617)

Delivery devices or storage media for fragrances and flavors based on ionic liquids that include a covalent attachment of the active compound and immobilization as a salt and there application for storage as well as for prolonged and controlled triggered release not mentioned in any form in prior literature.

Ions

The disclosed ionic liquids contain at least one kind of cation and at least one kind of anion. Examples of suitable cations and anions are disclosed herein. It should be understood that when a particular compound is disclosed as being a cation, for example, it can also, in other circumstances, be an anion and vice versa. Many compounds are known to exist as cations in some environments and anions in other environments. Further, many compounds are known to be convertible to cations and anions through various chemical transformations. Examples of such compounds are disclosed herein.

The materials, compounds, compositions, and components that can be used for, can be used in conjunction with, can be used in preparation for, or are products of the disclosed methods and compositions are disclosed herein. It is understood that when combinations, subsets, interactions, groups, etc. of these materials are disclosed that while specific reference to each various individual and collective combinations and permutation of these compounds may not be explicitly disclosed, each is specifically contemplated and described herein. For example, if an ionic liquid composition is disclosed and a number of modifications that can be made to a number of components of the ionic liquid composition are discussed, each and every combination and permutation that are possible are specifically contemplated unless specifically indicated to the contrary. Thus, if a class of cations A, B, and C are disclosed as well as a class of anions D, E, and F and an example of a ionic liquid A-D is disclosed, then even if each is not individually recited, each is individually and collectively contemplated. Thus, in this example, each of the ionic liquids A-E, A-F, B-D, B-E, B-F, C-D, C-E, and C-F are specifically contemplated and should be considered disclosed from disclosure of A, B, and C; D, E, and F; and the example ionic liquid A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Cations

Particular examples of cationic compounds that can be present in the disclosed ionic liquid compositions are compounds that contain nitrogen atoms. Nitrogen atoms can exist or can be converted to positively-charged quaternary ammonium species, for example, through alkylation or protonation of the nitrogen atom. Thus compounds that possess a quaternary nitrogen atom (known as quaternary ammonium compounds (QACs)) are typically cations. According to the methods and compositions disclosed herein, any compound that contains a quaternary nitrogen atom or a nitrogen atom that can be converted into a quaternary nitrogen atom can be a suitable cation for the disclosed ionic liquid compositions.

QACs can have numerous biological properties that one may desire to be present in the disclosed ionic liquid compositions. For example, many QACs are known to have antibacterial properties. The antibacterial properties of QACs were first observed toward the end of the 19$^{th}$ century among the carbonium dyestuffs, such as auramin, methyl violet, and malachite green. These types of compounds are effective chiefly against the Gram-positive organisms. Jacobs and Heidelberger first discovered QACs antibacterial effect in 1915 studying the antibacterial activity of substituted hexamethylene-tetrammonium salts (Jacobs and Heidelberger, *Proc Nat Acad Sci USA,* 1915, 1:226; Jacobs and Heidelberger, *J Biol Chem,* 1915, 20:659; Jacobs and Heidelberger, *J Exptl Med,* 1916, 23:569).

Browning et al. found great and somewhat less selective bactericidal powers among quaternary derivatives of pyridine, quinoline, and phenazine (Browning et al., *Proc Roy Soc London,* 1922, 93B:329; Browning et al., *Proc Roy Soc London,* 1926, 100B:293). Hartman and Kagi observed antibacterial activity in QACs of acylated alkylene diamines (Hartman and Kagi, *Z Angew Chem,* 1928, 4:127).

In 1935, Domagk synthesized long-chain QACs, including benzalkonium chloride, and characterized their antibacterial activities (Domagk, *Deut Med Wochenschr,* 1935, 61:829). He showed that these salts are effective against a wide variety of bacterial strains. This study of the use of QACs as germicides was greatly stimulated.

Many scientists have focused their attention on water soluble QACs because they exhibit a range of properties: they are surfactants, they destroy bacteria and fungi, they serve as a catalyst in phase-transfer catalysis, and they show antielectrostatic and anticorrosive properties. They exert antibacterial action against both Gram-positive and Gram-negative bacterial as well as against some pathogen species of fungi and protozoa. These multifunctional salts have also been used in wood preservation, their application promoted in the papers of Oertel and Butcher et al. (Oertel, *Holztechnologie,* 1965, 6:243; Butcher et al., *For Prod J,* 1977, 27:19; Butcher et al., *J For Sci,* 1978, 8:403).

QACs are also widely used as skin antiseptics, disinfectants, fabric softeners, antistatic agents, cleaning agents, and preservatives. Detergent properties and antimicrobial activities of QACs have made them useful for general environmental sanitations, for examples, in hospitals and food production facilities. In pharmacological preparations they are used such as mouth rinses, lozenges, sprays and gels.

In humans and animals QACs have been considered too toxic for systematic applications, but are accepted to be safe for topical applications. Furthermore, QACs have recently been used as penetration enhancers for transnasal and transbuccal drug delivery, as well as in nasal vaccination (Klinguer et al., *Vaccine,* 2001, 19:4236). This ability to penetrate and open cell membrane has been widely used in drug delivery via liposomes (mainly QACs with two long alkyl chains) and non-viral gene delivery (Liu and Huang, *J Contr Rel,* 2002, 78:259). Many examples of compounds having nitrogen atoms, which exist as quaternary ammonium species or can be converted into quaternary ammonium species, are disclosed herein.

In some examples, when the cation is a quaternary ammonium compound, the anion is not an inorganic anion, examples of which are disclosed herein. In other examples, where the cation is a quaternary ammonium compound, the anion is not a halide.

Aliphatic Heteroaryls

Some specific QACs suitable for use herein are aliphatic heteroaryls. An aliphatic heteroaryl cation is a compound that comprises an aliphatic moiety bonded to a heteroaryl moiety. In the aliphatic heteroaryl cation, the aliphatic moiety can be any alkyl, alkenyl, alkynyl, cycloalkyl, or cycloalkenyl group, as described herein. Generally, the aliphatic moiety can comprise at least 10, at least 12, at least 14, at least 16, at least 18, or at least 20 carbon atoms. In other examples, the aliphatic moiety can comprise a mixture of aliphatic groups having a range of carbon atoms. For example, the aliphatic moiety can comprise from 10 to 40, from 12 to 38, from 14 to 36, from 16 to 34, from 18 to 32, from 14 to 18, or from 20 to 30 carbon atoms. In some specific examples, the aliphatic moiety can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. Examples of specific aliphatic moieties that can be used include, but are not limited to, decyl, dodecyl (lauryl), tetradecyl (myristyl), hexadecyl (palmityl or cetyl), octadecyl (stearyl), eicosyl (arachidyl), and linolenyl groups, including branched derivatives thereof and any mixtures thereof. In the aliphatic heteroaryl cations, the aliphatic moiety is bonded to a heteroatom in the heteroaryl moiety.

In the aliphatic heteroaryl cation, the heteroaryl moiety can be any heteroaryl moiety as described herein. For example, the heteroaryl moiety can be an aryl group having one or more heteroatoms (e.g., nitrogen, oxygen, sulfur, phosphorous, or halonium). Examples of specific heteroaryl moieties that can be used in the aliphatic heteroaryl cations include, but are not limited to, pyrazole, pyridine, pyrazine, pyrimidine, pryidazine, indolizine, isoindole, indole, indazole, imidazole, oxazole, triazole, thiazole, purine, isoquinoline, quinoline, phthalazine, quinooxaline, phenazine, and the like, including substituted derivatives and mixtures thereof. In the aliphatic heteroaryl cations, a heteroatom in the heteroaryl moiety is bonded to the aliphatic moiety. When the heteroatom of the heteroaryl is nitrogen, this forms a quaternary ammonium cation, as described herein.

Further examples of aliphatic heteroaryl cations are those having the following structures:

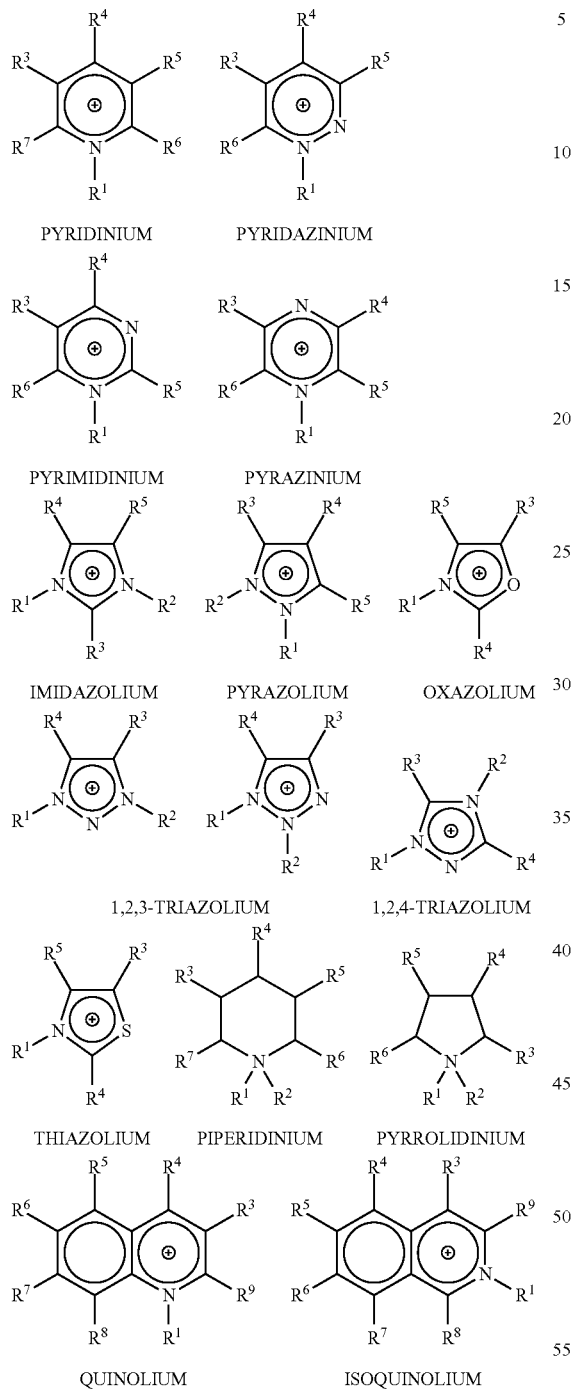

wherein $R^1$ and $R^2$ are, independently, a $C_1$-$C_6$ alkyl group or a $C_1$-$C_6$ alkoxyalkyl group, and $R^3$, $R^4$, $R^5$, $R^6$, $R^7$, $R^8$, and $R^9$($R^3$-$R^9$), when present, are independently H, a $C_1$-$C_6$ alkyl, a $C_1$-$C_6$ alkoxyalkyl group, a $C_1$-$C_6$ alkoxy group, or an energetic substituents such as nitro, amino, cyano, azido, alkyl nitro, alkyl amino, alkyl cyano, alkyl azido, alkoxy nitro, alkoxy amino, alkoxy cyano, and alkoxy azido. In other examples, both $R^1$ and $R^2$ groups are $C_1$-$C_4$ alkyl, with one being methyl, and $R^3$-$R^9$, when present, are H. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1$-$C_6$ alkoxy groups contain the above $C_1$-$C_6$ alkyl group bonded to an oxygen atom that is also bonded to the cation ring. An alkoxyalkyl group contains an ether group bonded to an alkyl group, and here contains a total of up to six carbon atoms. It is to be noted that there are two isomeric 1,2,3-triazoles. In some examples, all R groups not required for cation formation can be H.

The phrase "when present" is often used herein in regard to substituent R group because not all cations have all of the numbered R groups. All of the contemplated cations contain at least four R groups, which can be H, although $R^2$ need not be present in all cations.

In one example, all R groups that are not required for cation formation; i.e., those other than $R^1$ and $R^2$ for compounds other than the imidazolium, pyrazolium, and triazolium cations shown above, are H.

A cation that contains a single five-membered ring that is free of fusion to other ring structures is suitable for use herein. Exemplary cations are illustrated below wherein $R^1$, $R^2$, and $R^3$-$R^5$, when present, are as defined before.

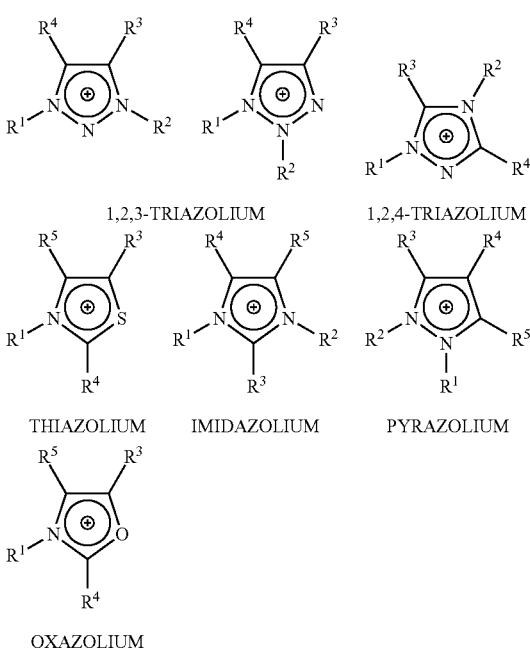

Of the cations that contain a single five-membered ring free of fusion to other ring structures, an imidazolium cation that corresponds in structure to Formula A is also suitable, wherein $R^1$, $R^2$, and $R^3$-$R^5$, are as defined before.

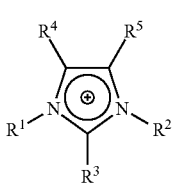

(A)

In a further example, an N,N-1,3-di-($C_1$-$C_6$ alkyl)-substituted-imidazolium ion can be used; i.e., an imidazolium cation wherein $R^3$-$R^5$ of Formula A are each H, and $R^1$ and $R^2$ are independently each a $C_1$-$C_6$ alkyl group or a $C_1$-$C_6$ alkoxyalkyl group. In yet another example, the cation illustrated by a compound that corresponds in structure to Formula B, below, wherein $R^3$-$R^5$ of Formula A are each hydrogen and $R^1$ is a $C_1$-$C_6$-alkyl group or a $C_1$-$C_6$ alkoxyalkyl group.

(B)

Aliphatic Benzylalkyl Ammonium

The disclosed ionic liquid compositions can also comprise an aliphatic benzylalkyl ammonium cation. An aliphatic benzylalkyl ammonium cation is a cation that comprises an aliphatic moiety bonded to the nitrogen atom of a benzylalkyl amine moiety. The aliphatic moiety can be as described herein. The benzylalkyl amine moiety can be a benzyl amine where the amine is bonded to an alkyl or cyclic alkyl group, as described herein. One or more types of aliphatic benzylalkyl ammonium cation can be used in the ionic liquid compositions disclosed herein. The aliphatic benzylalkyl ammonium cation suitable for use herein can be prepared by methods known in the art or can be obtained from commercial sources.

In one aspect, the aliphatic benzylalkyl ammonium cation can be represented by the following formula:

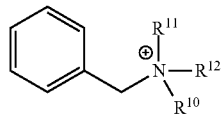

wherein $R^{10}$ is an aliphatic group, as described above, $R^{11}$ and $R^{12}$ are, independent of one another, alkyl groups or cyclic alkyl groups as described herein. In some examples, one or more of the "R" substituents can be a long chain alkyl group (e.g., the number of carbon atoms is 10 or greater). In other examples, one or more of the "R" substituents can be a short chain alkyl group (e.g., the number of carbon atoms is less than 10). In still other examples, one of the "R" substituents is a long chain alkyl group and the other two "R" substituents are short chain alkyl groups.

In one aspect, the aliphatic benzylalkyl ammonium cation can have any of the aliphatic moieties disclosed herein bonded to any benzylalkyl amine moieties disclosed herein. In some specific examples, $R^{10}$ in the formula of aliphatic benzylalkyl ammonium cation can be an aliphatic group of from 10 to 40 carbon atoms, e.g., a decyl, dodecyl (lauryl), tetradecyl (myristyl), hexadecyl (palmityl or cetyl), octadecyl (stearyl), or eicosyl (arachidyl) group, and $R^{11}$ and $R^{12}$ can each be, independent of one another, a methyl, ethyl, propyl, butyl, pentyl, or hexyl group.

In another aspect, the aliphatic benzylalkyl ammonium cation can include, but are not limited to, alkyl dimethyl benzyl ammonium cations. Specific examples of alkyl dimethyl benzyl ammonium cations include, but are not limited to, cetyl dimethyl benzyl ammonium, lauryl dimethyl benzyl ammonium, myristyl dimethyl benzyl ammonium, stearyl dimethyl benzyl ammonium, and arachidyl dimethyl benzyl ammonium.

In yet another aspect, the aliphatic benzylalkyl ammonium cation can include, but are not limited to, alkyl methylethyl benzyl ammonium cations. Specific examples of alkyl methylethyl benzyl ammonium cations include, but are not limited to, cetyl methylethyl benzyl ammonium, lauryl methylethyl benzyl ammonium, myristyl methylethyl benzyl ammonium, stearyl methylethyl benzyl ammonium, and arachidyl methylethyl benzyl ammonium.

Dialiphatic Dialkyl Ammonium

Still further examples of QACs that can be used in the disclosed ionic liquid compositions are dialiphatic dialkyl ammonium cations. A dialiphatic dialkyl ammonium cation is a compound that comprises two aliphatic moieties and two alkyl moieties bonded to a nitrogen atom. The aliphatic moieties can be the same or different and can be any aliphatic group as described above. The alkyl moieties can be the same or different can be any alkyl group as described above. In the disclosed dialiphatic dialkyl ammoniums cations, the two aliphatic moieties can have 10 or more carbon atoms and the two alkyl moieties can have less than 10 carbon atoms. In another alternative, the two aliphatic moieties can have less than 10 carbon atoms and the two alkyl moieties can have 10 or more carbon atoms. One or more types of dialiphatic dialkyl ammonium cations can be used in the ionic liquid compositions disclosed herein.

In some particular examples, the dialiphatic dialkyl ammonium cation can be di-dodecyl dimethyl ammonium, di-tetradecyl dimethyl ammonium, dihexadecyl dimethyl ammonium, and the like, including combinations thereof.

Tetraalkyl Ammonium

The disclosed ionic liquid compositions can also comprise a tetraalkyl ammonium cation. Suitable tetraalkyl ammonium cations comprise four alkyl moieties, as disclosed herein. In one example, a tetraalkyl ammonium cation can comprise one long chain alkyl moiety (e.g., 10 or more carbon atoms in length) and three short chain alkyl moieties (e.g., less than 10 carbon atoms in length).

Some specific examples of tetraalkyl ammonium cations that can be included in the disclosed ionic liquid compositions include, but are not limited to, cetyl trimethyl ammonium, lauryl trimethyl ammonium, myristyl trimethyl ammonium, stearyl trimethyl ammonium, arachidyl trimethyl ammonium, or mixtures thereof. Other examples include, but are not limited to, cetyl dimethylethyl ammonium, lauryl dimethylethyl ammonium, myristyl dimethylethyl ammonium, stearyl dimethylethyl ammonium, arachidyl dimethylethyl ammonium, or mixtures thereof.

Other Cations

Other cations that are suitable for use in the disclosed methods and compositions are compounds that contain metals. According to the methods and compositions disclosed herein, any compound that contains a metal atom can be a suitable cation. Organometallic compounds or metal complexes commonly have one or more metal atom in a positive oxidation state. Examples of metals that can be present in a suitable cation include, but are not limited to, lithium, sodium, potassium beryllium, magnesium, calcium, strontium, chromium, manganese, iron, cobalt, nickel, copper, and zinc. Silver nanoparticles can also be used. Examples of suitable organometallic cations include, but are not limited to, metallocenium, alkylgermanyl, alkyltin, or alkylsilyl (e.g., trimethylsilylium, triethylsilylium, tris(trimethylsilyl)silylium, tribenzylsilylium, triphenylsilylium, tricyclohexylsilylium, and dimethyloctadecylsilylium).

Another suitable group of quaternary ammonium cations are those that have been prepared by esterifying a compound containing a carboxylic acid moiety or transesterifying a compound with an ester moiety with a choline moiety. Such choline esters can be biofriendly, permanent ions that are amenable to being added to various compounds while still being easily cleavable under physiological conditions. The choline esters can be used to increase the solubility and bioavailability of many neutral compounds.

Further examples of cations include (2-hydroxyethyl)-dimethylundecyloxymethyl-ammonium, (2-acetoxyethyl)-heptyloxymethyldimethylammonium, and (2-acetoxyethyl)-dodecyloxymethyldimethylammonium, mepenzolate, sulfathiazole, thimerosal, and valproic acid.

In other examples, the cation can be an energetic cation as disclosed in Katritzky et al., "ILs Based on Energetic Imidazolium Cations: Nitro- and Nitrile-substituted N,N' Dialkylimidazolium Salts" New J Chem 30:349, 2006, which is incorporated by reference herein at least for its teachings of energetic ions.

Anions

Particular examples of anionic compounds that can be present in the disclosed ionic liquids are compounds that contain oxygen atoms. Oxygen atoms can exist or can be converted to negatively charged, anionic species, for example, through deprotonation of alcohols or acids, through saponification of esters, or through alkylation of ketones. Likewise, compounds that contain sulfur atoms can also exist or be converted to anionic species through similar reactions. Still further, compounds that contain nitrogen atoms, especially nitrogen atoms adjacent to electron withdrawing groups or resonance stabilizing structures, can be converted to anions through deprotonation. According to the methods and compositions disclosed herein, any compound that contains an oxygen, sulfur, or nitrogen atom can be a suitable anion for the disclosed ionic liquid compositions.

Other suitable anions include, but are not limited to, halides (e.g., fluoride, chloride, bromide, and iodide), sulfates ($SO_4^-$), carbonates, bicarbonates, phosphates, phosphates, nitrates ($NO_3^-$), nitrites ($NO_2^-$), acetates ($CH_3CO_2^-$), and the like. Other examples of anions include, but are not limited to $PF_6^-$ that is immiscible in water and $BF_4^-$ that is miscible in water depending on the ratio of ionic liquid to water, system temperature, and alkyl chain length of cation. Other anions include triflate (TfO; $CF_3SO_2^-$), nonaflate (NfO; $CF_3(CF_2)_3SO_2^-$), bis(triflyl)amide ($Tf_2N$; $(CF_3SO_2)_2N^-$), trifluoroacetate (TFA; $CF_3CO_2^-$), and heptafluororobutanoate (HB; $CF_3(CF_2)_3SO_2^-$). Other types of ionic liquids include haloaluminates, such as chloroaluminate.

Other suitable anions contemplated herein are saccharin and acesulfame. Saccharin, as an alkali metal salt, and acesulfame (6-methyl-3,4-dihydro-1,2,3-oxathiazin-4-one 2,2-dioxide), which has previously only been offered as potassium salt, are in widespread use in foodstuffs as non-nutritive sweeteners. Such anions can be used when one desires to prepare an ionic liquid composition that has sweetness as one of its desired properties. For example, saccharin and acesulfame can be combined with pharmaceutically active cations to prepare sweet tasting ionic liquids that have pharmaceutical activity.

Specific examples of other anions include piperacillin, folic acid, ibuprofen, fast green FCF, docusate, acesulfamate, penicillin G, Colawet MA-80, salicylic acid, saccharinate, sulfacetamide, naproxen, benzoate, diclofenac, and trans-cinnamic acid.

Other suitable anions include, but are not limited to, substituted and un-substituted imidazolates, 1,2,3-triazolates, and 1,2,4-triazolates, benzimidazolates, benz-1,2,3-triazolates, as shown bellow:

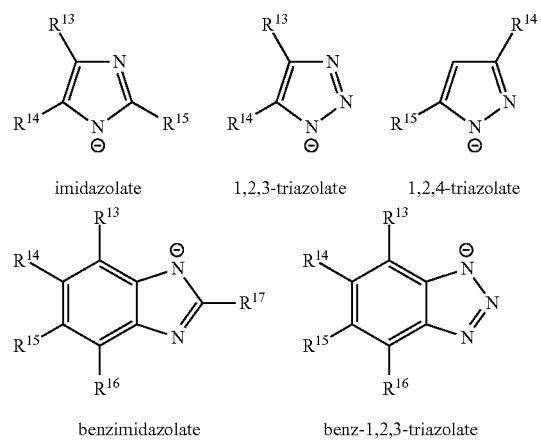

wherein $R^{13}$, $R^{14}$, $R^{16}$, $R^{17}$, ($R^{13-17}$), when present, are independently H, a $C_1$-$C_6$ alkyl, a $C_1$-$C_6$ alkoxyalkyl group, a $C_1$-$C_6$ alkoxy group, or energetic substituents like nitro, amino, cyano, azido, alkyl nitro, alkyl amino, alkyl cyano, alkyl azido, alkoxy nitro, alkoxy amino, alkoxy cyano, and alkoxy azido. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1$-$C_6$ alkoxy groups contain the above $C_1$-$C_6$ alkyl group bonded to an oxygen atom that is also bonded to the cation ring. An alkoxyalkyl group contains an ether 10 group bonded to an alkyl group, and here contains a total of up to six carbon atoms. It is to be noted that there are two isomeric 1,2,3-triazoles. In some examples, all R groups not required for anion formation can be H.

Further examples of suitable energetic anions are disclosed in Katritzky et al., "ILs Based on Energetic Azolate Anions," Chem Eur J 12:4630, 2006, which is incorporated by reference herein at least for its teachings of energetic anions.

Compound that can Exist that as Both: Anion or Cation

Examples of compounds that exist as cations in some environments and anions in other environments include, but are not limited to, 1,3-dimethylimidazolium, 1-butyl-3-methylimidazolium, 1,2,3-triazolium, tetrazolium, 1,2,4-triazolium, 1,3-dimethyl-1,2,3-triazolium, and 1,3-dimethyl-4-nitroimidazolium, which exist as a cations, and 4-nitroimidazolate, 4,5-dinitroimidazolate, 3,5-dinitro-1,2,4-triazolate, tetrazolate, 5-aminotetrazolate, 2-nitroimidazolate, which exist as an anion. Those separate ions can still form single product ionic liquids.

Examples of compounds that can change from an anion in one environment to a cation in another environment due to chemical modifications are the sulfur ylides through the reaction of a sulfide with methyliodide to form the sulfonium ion.

Specific Examples of Pharmaceutical Actives

When pharmaceutical activity is a desired property of the disclosed ionic liquids, one or more of the ions in the disclosed ionic liquid compositions can be a pharmaceutical active. Pharmaceutical actives that exist as ions or can be converted to ions, and which are suitable for use in preparing the disclosed ionic liquid compositions, include the following categories and specific examples. It is not intended that the category be limited by the specific examples. Those of ordinary skill in the art will be able to readily identify those pharmaceutical actives that can be used in the disclosed methods and compositions. For example, one can identify a compound with a given property or activity by consulting various sources, such as the Merck Index (13$^{th}$ Edition, Wiley, 2001), The United States Pharmacopeia—National Formulary (USP-NF), and the FDA's Orange book, which are each incorporated by reference herein at least for their teachings of pharmaceutical actives. Once a compound with a desired property is identified, the skilled artisan can determine whether the compound is ionic or can be made ionic. Such determinations can be performed based on the compound's structure, which can readily be determined by consulting the sources mentioned herein or experimentally. Knowing a compound's structure can readily reveal if the compound is ionic. In fact, many pharmaceutical actives exist as salts and are thus suitable for use in preparing the disclosed ionic liquid compositions. Further, if a compound is not ionic, but contains an ion forming moiety (e.g., nitrogen, oxygen, sulfur, or metal atoms, as described herein), the compound can be converted to an ion and then combined with a suitable counterion to prepare the disclosed ionic liquid compositions. Those of ordinary skill in the art will recognize numerous other compounds that fall within the categories and that are useful according to the disclosed compositions and methods.

Some specific examples of pharmaceutical actives that can be used in the disclosed ionic liquids include, but are not limited to, aspirin, LIBRIUM™, isoniazid, penicillin, PRONTOSIL™, cisplatin, 6-mercaptopurine, RITUXAN™, TAXOL™, phenobarbital, PROZAC™, ALLEGRA™, VIOXX™, quinine, ivermectin, L-dopa, THORAZINE™, salvarsan, TAGAMET™, AZT, crixivan, salbutamol, digoxin, fluride, LOVASTATIN™, erythropoietin, hydrocortisone, insulin, oral contraceptives, oxytocin, PREMARIN™, RU-486, thyroxine, thalidomide, cyclosporine, fentanyl, methadone, morphine, botox, vitamins, FOSAMAX™, RITALIN™, and VIAGRA™, including ionic derivatives thereof. Other examples of pharmaceutical active ions or pharmaceutical actives that can be made ionic include, but are not limited to, pantoprazole, sold under the trade names PROTONIX™ and PANTOZOL™, and rabeprazole, sold under the trade names ACIPHEX™ and PARIET™, which are used to treat gastrointestinal disorders. Risedronate, sold under the trade name ACTONEL™, and alendronate, sold under the trade name FOSAMAX™, are used to treat osteoporosis and are further examples of suitable compounds that can be used to prepare the disclosed ionic liquid compositions. Further examples include losartan, sold under the trade names NU-LOTAN™, COZAAR™, and HYZAAR™, and fosinopril, sold under the trade name MONOPRIL™, which are used to treat hypertension and are other examples of suitable compounds that can be used to prepare the disclosed ionic liquid compositions. Atorvastatin, sold under the trade name LIPITOR™, and pravastatin, sold under the trade name PRAVACHOL™, are used to treat cholesterol and are further examples of suitable compounds that can be used to prepare the disclosed ionic liquid compositions. A further example is montelukast, which is used to treat asthma and is sold under the trade name SINGULAIR™. Further examples of pharmaceutical actives that are ionic or can be made ionic and combined with other ions to form the disclosed ionic liquid compositions are: prostaglandin $E_2$, prostaglandin $F2_4$, sulprostone, cetapril, benzaepril, captopril, methyl hexaneamine, synephrine, isoetharine, methoxyphenamine, tamsulosin, tolazoline, bufuralol, nadoxolol, acetylsalicylsalicylic acid, ammonium salicylate, buthalital sodium, thiopental sodium, isobutyl p-aminobenzoate, phenol, clortermine, fenproporex, dermatol, niclosamide, pelletierine, dithiazanine iodide, thiabendazole, antimony sodium thioglycolate, niridazole, isotretinoin, lodoxamide, ramatroban, finasteride, minoxidil, carbarsone, diphetarsone, flutamide, nilutamide, nicorandil, ozagrel, bunitrolol, ipratropium bromide, pyridinol carbamate, bucillamine, diacerein, amlexanox, cromolyn, azidamfenicol, thiamphenicol, brodimoprim, tetroxoprim, acetosulfone sodium, dapsone, benzoylpas, cyamelide, picotamide, acetylpheneturide, albutoin, caroxazone, indalpine, calcium mesoxalate, buformin, alkofanone, metformin, edrophomium chloride, neostigmine, p-aminopro-piophenon, methylene blue, folinic acid, tiopronin, fomepizole, asoxime chloride, obidoxime chloride, chlonidine, tiapride, alizapride, bromopride, potassium p-aminobenzoate, chlordantoin, bromosalicylchloranilide, acetazolamide, benfunolol, allopurinol, carprofen, acrivastine, Metron S, Acifran, Benfluorex, Chlorisoncl-amine chloride, Pentamethon-ium bromide, 2-Aminothiazole, Methylthio-uracil, Amexinium Methyl Sulfate, Dopamine Hydrochloride, Balsalazide, Mesalamine, Enfenamic Acid, Menfenamic Acid, Flufenamic Acid Aluminum Salt, Berberine, Chloguanide, Valproic Acid, Lisuride, Naratriptan, Ambutonium Bromide, Benzilonium Bromide, 9-Amino-camptothecin, Tenuazonic Acid, Clometocillin, Fluoxetine Hydrochloride, Pamidronic Acid, Risedronate Sodium, Benserazide Hydrochloride, Carbidopa, Metyrosine, Phentolamine, Elformithine Hydrochloride monohydrate, Sulfamethox-azole, Tamsulosin Hydrochloride, Terazosin, Nitazoxanide, Acranil', Hydroxystil-bamidine, Pentamidine, Pyrimethamine, Acetarsone, Aminitrozole, Benznidazole, Eflornithine Hydrochlo-ride, Acitretin, 6-Azauridine, Amisulpride, Remoxipride Hydrochloride Monohydrate, Bufe-xamac, Bumadizon, Chloram-phenicol, Benzoxonium, Chloride, Cetalkonium Chloride, Aliben-dol, Ambutonium Bromide, Arshpenamine, Sodium Arsanilate, Anagrelide, Beraprost, Cilostazol, Bibenzonium Bromide, Sodium Dibunate, Aldioxa, Cimetidine, Allopurinol, Succinimide, Foscarnet Sodium, Efavirenz, Etifoxine, Valnoctamide, Cannabinol, Oxitropium Bromide, Tiotropium Bromide, Fendiline Hydrochloride, Prenylamine, Acetazolamide, Flumethiazide, Acadesine, Cariporide, Levosimendan, Pimobendan Hydrochloride, Ursodiol, Chenodiol, Cholic Acid Monohydrate, Clanobutin, Echothiophate Iodide, Edrophonium Chloride, Ambenonium, hloride, Distigmine Bromide, Asoxime Chloride, Obidoxime Chloride, Pemoline, Phenmetrazine, Celecoxib, Cetraxate, Irsogladine, Naphazoline Hydrochloride, Nordefrin Hydrochloride, Dapsone, Sulfapyridine Sodium Salt, Mercapto-merin Sodium, Mercumatilin Sodium, Pergolid, Pramipexole, Dihydro-chloride, Amisulpride, Sulpiride, Cephaeline, Bromhexine, Ambroxol Hydrochloride, Carnitine, Cinitapride, Cisapride, Cortivazol, Enoxolone, Clomiphene, Pentoxifylline, Adrenalone, Carbazochrome, odium Sulfonate, Thioctic Acid, Timonacid, Pidotimod, Bucillamine, 6-Mercapto-purine, Brequinar, Retinoic Acid, Salicylic Acid, Docusate Calcium (Sodium), Picosolfate Sodium, Ibudilast, Zafirlukast, Choline Chloride, Methionine, Bismuth Sodium Triglycollam-ate, Chloroquine, Prinomastat, Carbachol, Neostigmine, Acetylcysteine, Bromhexine, Tetrazepam, Tizanidine, Tropicamide, Phenylephrine, Hydrochloride, Cyclazocine, Amiphenazole, Zanamivir, Succinyl-choline Bromide/Chloride/, Iodide, Fazadinium Bromide, Omapatrilat, Riluzole, Repinotan, Indeloxazine Hydrochloride, Donepezil, Carboprost, Pinacidil, Nicorandil, Fampridine, Tedisamil, Cabergoline, Beraprost, Dimefline, Fominoben, 2-Hexyl-decanoic Acid, Sodium Tetradecyl Sulfate, Flurazepam, Etodroxizine, Hexafluor-enium, romide, Ritodrine, Terbutaline, p-Aminobenzoic Acid, Solisobenzone, Ticrynafen, Orotic Acid, Nafronyl, Nicametate, Perhexyline, Cloricromen, Ciclonicate, Cinepazide, Chromocarb, Dobesilate Calcium, Thiamine (Vit. B), Pyridoxine Hydrochloride (Vit. $B_5$), Oxaceprol, Acetylcysteine, Penicillamine, Allopurinol, Further examples of pharmaceutical actives that are ionic or can be made ionic and combined with other ions to form the disclosed ionic liquid compositions are detailed below, along with their typically pharmaceutical use.

Adrenergic: adrenalone, amidephrine mesylate, apraclonidine hydrochloride, brimonidine tartrate, dapiprazole hydrochloride, deterenol hydrochloride, dipivefrin, dopamine hydrochloride, ephedrine sulfate, epinephrine, epinephrine bitartrate, epinephryl borate, esproquin hydrochloride, etafedrine hydrochloride, hydroxyamphetamine hydrobromide, levonordefrin, mephentermine sulfate, metaraminol bitartrate, metizoline hydrochloride, naphazoline hydrochloride, norepinephrine bitartrate, oxidopamine, oxymetazoline hydrochloride, phenylephrine hydrochloride, phenylpropanolamine hydrochloride, phenylpropanolamine polistirex, prenalterol hydrochloride, propylhexedrine, pseudoephedrine hydrochloride, tetrahydrozoline hydrochloride, tramazoline hydrochloride, xylometazoline hydrochloride.

Adrenocortical steroid: ciprocinonide, desoxycorticosterone acetate, desoxycortico-sterone pivalate, dexamethasone acetate, fludrocortisone acetate, flumoxonide, hydrocortisone hemisuccinate, methylprednisolone hemisuccinate, naflocort, procinonide, timobesone acetate, tipredane.

Adrenocortical suppressant: aminoglutethimide, trilostane.

Alcohol deterrent: disulfuram.

Aldosterone antagonist: canrenoate potassium, canrenone, dicirenone, mexrenoate potassium, prorenoate potassium, spironolactone.

Amino acid: alanine, aspartic acid, cysteine hydrochloride, cystine, histidine, isoleucine, leucine, lysine, lysine acetate, lysine hydrochloride, methionine, phenylalanine, proline, serine, threonine, tryptophan, tyrosine, valine.

Ammonia detoxicant: arginine: arginine glutamate, arginine hydrochloride.

Anabolic: bolandiol dipropionate, bolasterone, boldenone undecylenate, bolenol, bolnantalate, ethylestrenol, methenolone acetate, methenolone enanthate, mibolerone, nandrolone cyclotate, norbolethone, pizotyline, quinbolone, stenbolone acetate, tibolone, zeranol.

Analeptic: modafinil.

Analgesic: acetaminophen, alfentanil hydrochloride, aminobenzoate potassium, aminobenzoate sodium, anidoxime, anileridine, anileridine hydrochloride, anilopam hydrochloride, anirolac, antipyrine, aspirin, benoxaprofen, benzydamine hydrochloride, bicifadine hydrochloride, brifentanil hydrochloride, bromadoline maleate, bromfenac sodium, buprenorphine hydrochloride, butacetin, butixirate, butorphanol, butorphanol tartrate, carbamazepine, carbaspirin calcium, carbiphene hydrochloride, carfentanil citrate, ciprefadol succinate, ciramadol, ciramadol hydrochloride, clonixeril, clonixin, codeine, codeine phosphate, codeine sulfate, conorphone hydrochloride, cyclazocine, dexoxadrol hydrochloride, dexpemedolac, dezocine, diflunisal, dihydrocodeine bitartrate, dimefadane, dipyrone, doxpicomine hydrochloride, drinidene, enadoline hydrochloride, epirizole, ergotamine tartrate, ethoxazene hydrochloride, etofenamate, eugenol, fenoprofen, fenoprofen calcium, fentanyl citrate, floctafenine, flufenisal, flunixin, flunixin meglumine, flupirtine maleate, fluproquazone, fluradoline hydrochloride, flurbiprofen, hydromorphone hydrochloride, ibufenac, indoprofen, ketazocine, ketorfanol, ketorolac tromethamine, letimide hydrochloride, levomethadyl acetate, levomethadyl acetate hydrochloride, levonantradol hydrochloride, levorphanol tartrate, lofemizole hydrochloride, lofentanil oxalate, lorcinadol, lomoxicam, magnesium salicylate, mefenamic acid, menabitan hydrochloride, meperidine hydrochloride, meptazinol hydrochloride, methadone hydrochloride, methadyl acetate, methopholine, methotrimeprazine, metkephamid acetate, mimbane hydrochloride, mirfentanil hydrochloride, molinazone, morphine sulfate, moxazocine, nabitan hydrochloride, nalbuphine hydrochloride, nalmexone hydrochloride, namoxyrate, nantradol hydrochloride, naproxen, naproxen sodium, naproxol, nefopam hydrochloride, nexeridine hydrochloride, noracymethadol hydrochloride, ocfentanil hydrochloride, octazamide, olvanil, oxetorone fumarate, oxycodone, oxycodone hydrochloride, oxycodone terephthalate, oxymorphone hydrochloride, pemedolac, pentamorphone, pentazocine, pentazocine hydrochloride, pentazocine lactate, phenazopyridine hydrochloride, phenyramidol hydrochloride, picenadol hydrochloride, pinadoline, pirfenidone, piroxicam olamine, pravadoline maleate, prodilidine hydrochloride, profadol hydrochloride, propiram fumarate, propoxyphene hydrochloride, propoxyphene napsylate, proxazole, proxazole citrate, proxorphan tartrate, pyrroliphene hydrochloride, remifentanil hydrochloride, salcolex, salethamide maleate, salicylamide, salicylate meglumine, salsalate, sodium salicylate, spiradoline mesylate, sufentanil, sufentanil citrate, talmetacin, talniflumate, talosalate, tazadolene succinate, tebufelone, tetrydamine, tifurac sodium, tilidine hydrochloride, tiopinac, tonazocine mesylate, tramadol hydrochloride, trefentanil hydrochloride, trolamine, veradoline hydrochloride, verilopam hydrochloride, volazocine, xorphanol mesylate, xylazine hydrochloride, zenazocine mesylate, zomepirac sodium, zucapsaicin.

Androgen: fluoxymesterone, mesterolone, methyltestosterone, nandrolone decanoate, nandrolone phenpropionate, nisterime acetate, oxandrolone, oxymetholone, silandrone, stanozolol, testosterone, testosterone cypionate, testosterone enanthate, testosterone ketolaurate, testosterone phenylacetate, testosterone propionate, trestolone acetate.

Anesthesia, adjunct to: sodium oxybate.

Anesthetic: aliflurane, benoxinate hydrochloride, benzocaine, biphenamine hydrochloride, bupivacaine hydrochloride, butamben, butamben picrate, chloroprocaine hydrochloride, cocaine, cocaine hydrochloride, cyclopropane, desflurane, dexivacaine, diamocaine cyclamate, dibucaine, dibucaine hydrochloride, dyclonine hydrochloride, enflurane, ether, ethyl chloride, etidocaine, etoxadrol hydrochloride, euprocin hydrochloride, fluoroxene, halothane, isobutamben, isoflurane, ketamine hydrochloride, levoxadrol hydrochloride, lidocaine, lidocaine hydrochloride, mepivacaine hydrochloride, methohexital sodium, methoxyflurane, midazolam hydrochloride, midazolam maleate, minaxolone, nitrous oxide, norflurane, octodrine, oxethazaine, phencyclidine hydrochloride, pramoxine hydrochloride, prilocalne hydrochloride, procaine hydrochloride, propanidid, proparacaine hydrochloride, propofol, propoxycaine hydrochloride, pyrrocaine, risocaine, rodocaine, roflurane, salicyl alcohol, sevoflurane, teflurane, tetracaine, tetracaine hydrochloride, thiamylal, thiamylal sodium, thiopental sodium, tiletamine hydrochloride, zolamine hydrochloride.

Anorectic compounds including dexfenfluramine.

Anorexic: a minorex, amphecloral, chlorphentermine hydrochloride, clominorex, clortermine hydrochloride, diethylpropion hydrochloride, fenfluramine hydrochloride, fenisorex, fludorex, fluminorex, levamfetamine succinate, mazindol, mefenorex hydrochloride, phenmetrazine hydrochloride, phentermine, sibutramine hydrochloride.

Antagonist: atipamezole, atosiban, bosentan, cimetidine, cimetidine hydrochloride, clentiazem maleate, detirelix acetate, devazepide, donetidine, etintidine hydrochloride, famotidine, fenmetozole hydrochloride, flumazenil, icatibant acetate, icotidine, isradipine, metiarnide, nadide, nalmefene, nalmexone hydrochloride, naloxone hydrochloride, naltrexone, nilvadipine, oxilorphan, oxmetidine hydrochloride, oxmetidine mesylate, quadazocine mesylate, ranitidine, ranitidine bismuth citrate, ranitidine hydrochloride, sufotidine, teludipine hydrochloride, tiapamil hydrochloride, tiotidine, vapiprost hydrochloride, zaltidine hydrochloride.

Anterior pituitary activator: epimestrol.

Anterior pituitary suppressant: danazol.

Anthelmintic: albendazole, anthelmycin, bromoxanide, bunamidine hydrochloride, butonate, cambendazole, carbantel lauryl sulfate, clioxanide, closantel, cyclobendazole, dichlorvos, diethylcarbamazine citrate, dribendazole, dymanthine hydrochloride, etibendazole, fenbendazole, furodazole, hexylresorcinol, mebendazole, morantel tartrate, niclosamide, nitramisole hydrochloride, nitrodan, oxantel pamoate, oxfendazole, oxibendazole, parbendazole, piperamide maleate, piperazine, piperazine citrate, piperazine edetate calcium, proclonol, pyrantel pamoate, pyrantel tartrate, pyrvinium pamoate, rafoxanide, stilbazium iodide, tetramisole hydrochloride, thiabendazole, ticarbodine, tioxidazole, triclofenol piperazine, vincofos, zilantel.

Anti-acne: adapalene, erythromycin salnacedin, inocoterone acetate, accutane.

Anti-adrenergic: acebutolol, alprenolol hydrochloride, atenolol, bretylium tosylate, bunolol hydrochloride, carteolol hydrochloride, celiprolol hydrochloride, cetamolol hydrochloride, ciclprolol hydrochloride, dexpropranolol hydrochloride, diacetolol hydrochloride, dihydroergotamine mesylate, dilevalol hydrochloride, esmolol hydrochloride, exaprolol hydrochloride, fenspiride hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, phentolamine mesylate, practolol, propranolol hydrochloride, proroxan hydrochloride, solypertine taitrate, sotalol hydrochloride, timolol, timolol maleate, tiprenolol hydrochloride, tolamolol, zolertine hydrochloride.

Anti-allergic: amlexanox, astemizole, azelastine hydrochloride, eclazolast, minocromil, nedocromil, nedocromil calcium, nedocromil sodium, nivimedone sodium, pemirolast potassium, pentigetide, pirquinozol, poisonoak extract, probicromil calcium, proxicromil, repirinast, tetrazolast meglumine, thiazinamium chloride, tiacrilast, tiacrilast sodium, tiprinast meglumine, tixanox.

Anti-amebic: berythromycin, bialamicol hydrochloride, chloroquine, chloroquine hydrochloride, chloroquine phosphate, clamoxyquin hydrochloride, clioquinol, emetine hydrochloride, iodoquinol, paromomycin sulfate, quinfamide, symetine hydrochloride, teclozan, tetracycline, tetracycline hydrochloride.

anti-androgen: benorterone, cioteronel, cyproterone acetate, delmadinone acetate, oxendolone, topterone, zanoterone.

Anti-anemic: epoetin alfa, epoetin beta, ferrous sulfate, dried, leucovorin calcium.

Anti-anginal: amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen, verapamil hydrochloride.

Anti-anxiety agent: adatanserin hydrochloride, alpidem, binospirone mesylate, bretazenil, glemanserin, ipsapirone hydrochloride, mirisetron maleate, ocinaplon, ondansetron hydrochloride, panadiplon, pancopride, pazinaclone, serazapine hydrochloride, tandospirone citrate, zalospirone hydrochloride.

Anti-arthritic: lodelaben.

Anti-asthmatic: ablukast, ablukast sodium, azelastine hydrochloride, bunaprolast, cinalukast, crornitrile sodium, cromolyn sodium, enofelast, isamoxole, ketotifen fumarate, levcromakalim, lodoxamide ethyl, lodoxamide tromethamine, montelukast sodium, ontazolast, oxarbazole, oxatomide, piriprost, piriprost potassium, pirolate, pobilukast edamine, quazolast, repirinast, ritolukast, sulukast, tetrazolast meglumine, tiaramide hydrochloride, tibenelast sodium, tomelukast, tranilast, verlukast, verofylline, zarirlukast.

Anti-atherosclerotic: mifobate, timefurone.

Anticholelithic: monoctanoin.

Anticholelithogenic: chenodiol, ursodiol.

Anticholinergic: alverine citrate, anisotropine methylbromide, atropine, atropine oxide hydrochloride, atropine sulfate, belladonna, benapryzine hydrochloride, benzetimide hydrochloride, benzilonium bromide, biperiden, biperiden hydrochloride, biperiden lactate, clidinium bromide, cyclopentolate hydrochloride, dexetimide, dicyclomine hydrochloride, dihexyverine hydrochloride, domazoline fumarate, elantrine, elucaine, ethybenztropine, eucatropine hydrochloride, glycopyrrolate, heteronium bromide, homatropine hydrobromide, homatropine methylbromide, hyoscyamine, hyoscyamine hydrobromide, hyoscyamine sulfate, isopropamide iodide, mepenzolate bromide, methylatropine nitrate, metoquizine, oxybutynin chloride, parapenzolate bromide, pentapiperium methylsulfate, phencarbamide, poldine methylsulfate, proglumide, propantheline bromide, propenzolate hydrochloride, scopolamine hydrobromide, tematropium methylsulfate, tiquinamide hydrochloride, tofenacin hydrochloride, toquizine, triampyzine sulfate, trihexyphenidyl hydrochloride, tropicamide.

Anticoagulant: ancrod, anticoagulant citrate dextrose solution, anticoagulant citrate phosphate dextrose adenine solution, anticoagulant citrate phosphate dextrose solution, anticoagulant heparin solution, anticoagulant sodium citrate solution, ardeparin sodium, bivalirudin, bromindione, dalteparin sodium, desirudin, dicumnarol, heparin calcium, heparin sodium, lyapolate sodium, nafamostat mesylate, phenprocoumon, tinzaparin sodium, warfarin sodium.

Anticoccidal: maduramicin.

Anticonvulsant: albutoin, ameltolide, atolide, buramate, carbamazepine, cinromide, citenamide, clonazepam, cyheptamide, dezinamide, dimethadione, divalproex sodium, eterobarb, ethosuximide, ethotoin, flurazepam hydrochloride, fluzinamide, fosphenyloin sodium, gabapentin, ilepcimide, lamotrigine, magnesium sulfate, mephenyloin, mephobarbital, methetoin, methsuximide, milacemide hydrochloride, nabazenil, nafimidone hydrochloride, nitrazepam, phenacemide, phenobarbital, phenobarbital sodium, phensuximide, phenyloin, phenyloin sodium, primidone, progabide, ralitoline, remacemide hydrochloride, ropizine, sabeluzole, stiripentol, sulthiame, thiopental sodium, tiletamine hydrochloride, topiramate, trimethadione, valproate sodium, valproic acid, vigabatrin, zoniclezole hydrochloride, zonisamide.

Antidepressant: adatanserin hydrochloride, adinazolam, adinazolam mesylate, alaproclate, aletamine hydrochloride, amedalin hydrochloride, amitriptyline hydrochloride, amoxapine, aptazapine maleate, azaloxan fumarate, azepindole, azipramine hydrochloride, bipenamol hydrochloride, bupropion hydrochloride, butacetin, butriptyline hydrochloride, caroxazone, cartazolate, ciclazindol, cidoxepin hydrochloride, cilobamine mesylate, clodazon hydrochloride, clomipramine hydrochloride, cotinine fumarate, cyclindole, cypenamine hydrochloride, cyprolidol hydrochloride, cyproximide, daledalin tosylate, dapoxetine hydrochloride, dazadrol maleate, dazepinil hydrochloride, desipramine hydrochloride, dexamisole, deximafen, dibenzepin hydrochloride, dioxadrol hydrochloride, dothiepin hydrochloride, doxepin hydrochloride, duloxetine hydrochloride, eclanamine maleate, encyprate, etoperidone hydrochloride, fantridone hydrochloride, fehmetozole hydrochloride, fenmetramide, fezolamine fumarate, fluotracen hydrochloride, fluoxetine, fluoxetine hydrochloride, fluparoxan hydrochloride, gamfexine, guanoxyfen sulfate, imafen hydrochloride, imiloxan hydrochloride, imipramine hydrochloride, indeloxazine hydrochloride, intriptyline hydrochloride, iprindole, isocarboxazid, ketipramine fumarate, lofepramine hydrochloride, lortalamine, maprotiline, maprotiline hydrochloride, melitracen hydrochloride, milacemide hydrochloride, minaprine hydrochloride, mirtazapine, moclobemide, modaline sulfate, napactadine hydrochloride, napamezole hydrochloride, nefazodone hydrochloride, nisoxetine, nitrafudam hydrochloride, nomifensine maleate, nortriptyline hydrochloride, octriptyline phosphate, opipramol hydrochloride, oxaprotiline hydrochloride, oxypertine, paroxetine, phenelzine sulfate, pirandamine hydrochloride, pizotyline, pridefine hydrochloride, prolintane hydrochloride, protriptyline hydrochloride, quipazine maleate, rolicyprine, seproxetine hydrochloride, sertraline hydrochloride, sibutramine hydrochloride, sulpiride, suritozole, tametraline hydrochloride, tampramine fumarate, tandamine hydrochloride, thiazesim hydrochloride, thozalinone, tomoxetine hydrochloride, trazodone hydrochloride, trebenzomine hydrochloride, trimipramine, trimipramine maleate, venlafaxine hydrochloride, viloxazine hydrochloride, zimeldine hydrochloride, zometapine.

Antidiabetic: acetohexamide, buformin, butoxamine hydrochloride, camiglibose, chlorpropamide, ciglitazone, englitazone sodium, etoformin hydrochloride, gliamilide, glibornuride, glicetanile sodium, gliflumide, glipizide, glucagon, glyburide, glyhexamide, glymidine sodium, glyoctamide, glyparamide, insulin, insulin, dalanated, insulin human, insulin human, isophane, insulin human zinc, insulin human zinc, extended, insulin, isophane, insulin lispro, insulin, neutral, insulin zinc, insulin zinc, extended, insulin, prompt, linogliride, linogliride fumarate, metformin, methyl palmoxirate, palmoxirate sodium, pioglitazone hydrochloride, pirogliride tartrate, proinsulin human, seglitide acetate, tolazamide, tolbutamide, tolpyrramide, troglitazone, zopolrestat, and sitagliptin.

Antidiarrheal: rolgamidine, diphenoxylate hydrochloride (lomotil), metronidazole (flagyl), methylprednisolone (medrol), sulfasalazine (azulfidine).

Antidiuretic: argipressin tannate, desmopressin acetate, lypressin.

Antidote: dimercaprol, edrophonium chloride, fomepizole, leucovorin calcium, levoleucovorin calcium, methylene blue, protamine sulfate.

Antidyskinetic: selegiline hydrochloride.

Anti-emetic: alosetron hydrochloride, batanopride hydrochloride, bemesetron, benzquinamide, chlorpromazine, chlorpromazine hydrochloride, cleboride, cyclizine hydrochloride, dimenhydrinate, diphenidol, diphenidol hydrochloride, diphenidol pamoate, dolasetron mesylate, domperidone, dronabinol, fludorex, flumeridone, galdansetron hydrochloride, granisetron, granisetron hydrochloride, lurosetron mesylate, meclizine hydrochloride, metoclopramide hydrochloride, metopimazine, ondansetron hydrochloride, pancopride, prochlorperazine, prochlorperazine edisylate, prochlorperazine maleate, promethazine hydrochloride, thiethylperazine, thiethylperazine malate, thiethylperazine maleate, trimethobenzamide hydrochloride, zacopride hydrochloride.

Anti-epileptic: felbamate, loreclezole, tolgabide.

Anti-estrogen: clometherone, delmadinone acetate, nafoxidine hydrochloride, nitromifene citrate, raloxifene hydrochloride, tamoxifen citrate, toremifene citrate, trioxifene mesylate.

Antifibrinolytic: nafamostat mesylate.

Antifungal: acrisorcin, ambruticin, amphotericin b, azaconazole, azaserine, basifungin, bifonazole, biphenamine hydrochloride, bispyrithione magsulfex, butoconazole nitrate, calcium undecylenate, candicidin, carbol-fuchsin, chlordantoin, ciclopirox, ciclopirox olamine, cilofungin, cisconazole, clotrimazole, cuprimyxin, denofungin, dipyrithione, doconazole, econazole, econazole nitrate, enilconazole, ethonam nitrate, fenticonazole nitrate, filipin, fluconazole, flucytosine, fungimycin, griseofulvin, hamycin, isoconazole, itraconazole, kalafungin, ketoconazole, lomofimgin, lydimycin, mepartricin, miconazole, miconazole nitrate, monensin, monensin sodium, naftifine hydrochloride, neomycin undecylenate, nifuratel, nifurmerone, nitralamine hydrochloride, nystatin, octanoic acid, orconazole nitrate, oxiconazole nitrate, oxifungin hydrochloride, parconazole hydrochloride, partricin, potassium iodide, proclonol, pyrithione zinc, pyrrolnitrin, rutamycin, sanguinarium chloride, saperconazole, scopafungin, selenium sulfide, sinefungin, sulconazole nitrate, terbinafine, terconazole, thiram, ticlatone, tioconazole, tolciclate, tolindate, tolnaftate, triacetin, triafungin, undecylenic acid, viridofulvin, zinc undecylenate, zinoconazole hydrochloride. One specific antifungal that is suitable is itraconazole.

Antiglaucoma agent: alprenoxime hydrochloride, colforsin, dapiprazole hydrochloride, dipivefrin hydrochloride, naboctate hydrochloride, pilocarpine, pimabine.

Antihemophilic: antihemophilic factor.

Antihemorrhagic: poliglusam.

Antihistaminic: acrivastine, antazoline phosphate, astemizole, azatadine maleate, barmastine, bromodiphenhydramine hydrochloride, brompheniramine maleate, carbinoxamine maleate, cetirizine hydrochloride, chlorpheniramine maleate, chlorpheniramine polistirex, cinnarizine, clemastine, clemastine fumarate, closiramine aceturate, cycliramine maleate, cyclizine, cyproheptadine hydrochloride, dexbrompheniramine maleate, dexchlorpheniramine maleate, dimethindene maleate, diphenhydramine citrate, diphenhydramine hydrochloride, dorastine hydrochloride, doxylamine succinate, ebastine, levocabastine hydrochloride, loratadine, mianserin hydrochloride, noberastine, orphenadrine citrate, pyrabrom, pyrilamine maleate, pyroxamine maleate, rocastine hydrochloride, rotoxamine, tazifylline hydrochloride, temelastine, terfenadine, tripelennamine citrate, tripelennamine hydrochloride, triprolidine hydrochloride, zolamine hydrochloride.

Antihyperlipidemic: cholestyramine resin, clofibrate, colestipol hydrochloride, crilvastatin, dalvastatin, dextrothyroxine sodium, fluvastatin sodium, gemfibrozil, lecimibide, lovastatin, niacin, pravastatin sodium, probucol, simvastatin, tiqueside, xenbucin.

Antihyperlipoproteinemic: acifran, beloxamide, bezafibrate, boxidine, butoxamine hydrochloride, cetaben sodium, ciprofibrate, gemcadiol, halofenate, lifibrate, meglutol, nafenopin, pimetine hydrochloride, theofibrate, tibric acid, treloxinate.

Antihypertensive: alfuzosin hydrochloride, alipamide, althiazide, amiquinsin hydrochloride, amlodipine besylate, amlodipine maleate, anaritide acetate, atiprosin maleate, belfosdil, bemitradine, bendacalol mesylate, bendroflumethiazide, benzthiazide, betaxolol hydrochloride, bethanidine sulfate, bevantolol hydrochloride, biclodil hydrochloride, bisoprolol, bisoprolol fumarate, bucindolol hydrochloride, bupicomide, buthiazide: candoxatril, candoxatrilat, captopril, carvedilol, ceronapril, chlorothiazide sodium, cicletanine, cilazapril, clonidine, clonidine hydrochloride, clopamide, cyclopenthiazide, cyclothiazide, darodipine, debrisoquin sulfate, delapril hydrochloride, diapamide, diazoxide, dilevalol hydrochloride, diltiazem malate, ditekiren, doxazosin mesylate, ecadotril, enalapril maleate, enalaprilat, enalkiren, endralazine mesylate, epithiazide, eprosartan, eprosartan mesylate, fenoldopam mesylate, flavodilol maleate, flordipine, flosequinan, fosinopril sodium, fosinoprilat, guanabenz, guanabenz acetate, guanacline sulfate, guanadrel sulfate, guancydine, guanethidine monosulfate, guanethidine sulfate, guanfacine hydrochloride, guanisoquin sulfate, guanoclor sulfate, guanoctine hydrochloride, guanoxabenz, guanoxan sulfate, guanoxyfen sulfate, hydralazine hydrochloride, hydralazine polistirex, hydroflumethiazide, indacrinone, indapamide, indolaprif hydrochloride, indoramin, indoramin hydrochloride, indorenate hydrochloride, lacidipine, leniquinsin, levcromakalim, lisinopril, lofexidine hydrochloride, losartan potassium, losulazine hydrochloride, mebutamate, mecamylamine hydrochloride, medroxalol, medroxalol hydrochloride, methalthiazide, methyclothiazide, methyldopa, methyldopate hydrochloride, metipranolol, metolazone, metoprolol fumarate, metoprolol succinate, metyrosine, minoxidil, monatepil maleate, muzolimine, nebivolol, nitrendipine, oformine, pargyline hydrochloride, pazoxide, pelanserin hydrochloride, perindopril erbumine, phenoxybenzamine hydrochloride, pinacidil, pivopril, polythiazide, prazosin hydrochloride, primidolol, prizidilol hydrochloride, quinapril hydrochloride, quinaprilat, quinazosin hydrochloride, quinelorane hydrochloride, quinpirole hydrochloride, quinuclium bromide, ramipril, rauwolfia serpentina, reserpine, saprisartan potassium, saralasin acetate, sodium nitroprusside, sulfinalol hydrochloride, tasosartan, teludipine hydrochloride, temocapril hydrochloride, terazosin hydrochloride, terlakiren, tiamenidine, tiamenidine hydrochloride, ticrynafen, tinabinol, tiodazosin, tipentosin hydrochloride, trichlormethiazide, trimazosin hydrochloride, trimethaphan camsylate, trimoxamine hydrochloride, tripamide, xipamide, zankiren hydrochloride, zofenoprilat arginine.

Antihypotensive: ciclafrine hydrochloride, midodrine hydrochloride.

Anti-infective: difloxacin hydrochloride, lauryl isoquinolinium bromide, moxalactam disodium, omidazole, pentisomicin, sarafloxacin hydrochloride, protease inhibitors of hiv and other retroviruses, integrase inhibitors of hiv and other retroviruses, cefaclor (CECLOR™), acyclovir (ZOVIRAX™), norfloxacin (NOROXIN™), cefoxitin (MEFOXIN™), cefuroxime axetil (CEFTIN™), ciprofloxacin (CIPRO™).

Anti-infective, topical: alcohol, aminacrine hydrochloride, benzethonium chloride: bithionolate sodium, bromchlorenone, carbamide peroxide, cetalkonium chloride, cetylpyridinium chloride: chlorhexidine hydrochloride, clioquinol, domiphen bromide, fenticlor, fludazonium chloride, fuchsin, basic, furazolidone, gentian violet, haiquinols, hexachlorophene: hydrogen peroxide, ichthammol, imidecyl iodine, iodine, isopropyl alcohol, mafenide acetate, meralein sodium, mercufenol chloride, mercury, ammoniated, methylbenzethonium chloride, nitrofurazone, nitromersol, octenidine hydrochloride, oxychlorosene, oxychlorosene sodium, parachlorophenol, camphorated, potassium permanganate, povidone-iodine, sepazonium chloride, silver nitrate, sulfadiazine, silver, symclosene, thimerfonate sodium, thimerosal: troclosene potassium.

Anti-inflammatory: acetominophen, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium.

Antikeratinizing agent: doretinel, linarotene, pelretin.

Antimalarial: acedapsone, amodiaquine hydrochloride, amquinate, arteflene, chloroquine, chloroquine hydrochloride, chloroquine phosphate, cycloguanil pamoate, enpiroline phosphate, halofantrine hydrochloride, hydroxychloroquine sulfate, mefloquine hydrochloride, menoctone, mirincamycin hydrochloride, primaquine phosphate, pyrimethamine, quinine sulfate, tebuquine.

Antimicrobial: aztreonam, chlorhexidine gluconate, imidurea, lycetamine, nibroxane, pirazmonam sodium, propionic acid, pyrithione sodium, sanguinarium chloride, tigemonam dicholine.

Antimigraine: dolasetron mesylate, naratriptan hydrochloride, sergolexole maleate, sumatriptan succinate, zatosetron maleate.

Antimitotic: podofilox.

Antimycotic: amorolfine.

Antinauseant: buclizine hydrochloride, cyclizine lactate, naboctate hydrochloride.

Antineoplastic: acivicin, aclarubicin, acodazole hydrochloride, acrqnine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, ethiodized oil I 131, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, gold au 198, hydroxyurea, idarubicin hydrochloride, ifosfamide, ilmofosine, interferon alfa-2a, interferon alfa-2b, interferon alfa-N1, interferon alfa-N3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safmgol, safingol hydrochloride, semustine, simtrazene, sparfosate sodium, sparsomycin, spirogermanium hydrochloride, spiromustine, spiroplatin, streptonigrin, streptozocin, strontium chloride sr 89, sulofenur, talisomycin, taxane, taxoid, tecogalan sodium, tegafur, teloxantrone hydrochloride, temoporfin, teniposide, teroxirone, testolactone, thiamiprine, thioguanine, thiotepa, tiazofurin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Other anti-neoplastic compounds include: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, atrsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dioxamycin, diphenyl spiromustine, docosanol, dolasetron, doxifluridine, droloxifene, dronabinol, duocannycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance genie inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, zinostatin stimalamer.

Anti-cancer supplementary potentiating agents: tricyclic anti-depressant drugs (e.g., imipramine, desipramine, amitryptyline, clomiprainine, trimipramine, doxepin, nortriptyline, protriptyline, amoxapine and maprotiline), non-tricyclic anti-depressant drugs (e.g., sertraline, trazodone and citalopram), Ca$^{++}$ antagonists (e.g., verapamil, nifedipine, nitrendipine and caroverine), calmodulin inhibitors (e.g., prenylamine, trifluoroperazine and clomipramine), amphotericin B, triparanol analogues (e.g., tamoxifen), antiarrhythmic drugs (e.g., quinidine), antihypertensive drugs (e.g., reserpine), thiol depleters (e.g., buthionine and sulfoximine) and Multiple Drug Resistance reducing agents such as Cremaphor EL.

Antineutropenic: filgrastim, lenograstim, molgramostim, regramostim, sargramostim.

Antiobsessional agent: fluvoxamine maleate.

Antiparasitic: abamectin, clorsulon, ivermectin.

Antiparkinsonian: benztropine mesylate, biperiden, biperiden hydrochloride, biperiden lactate, carmantadine, ciladopa hydrochloride, dopamantine, ethopropazine hydrochloride, lazabemide, levodopa, lometraline hydrochloride, mofegiline hydrochloride, naxagolide hydrochloride, pareptide sulfate, procyclidine hydrochloride, quinetorane hydrochloride, ropinirole hydrochloride, selegiline hydrochloride, tolcapone, trihexyphenidyl hydrochloride, antiperistaltic: difenoximide hydrochloride, difenoxin, diphenoxylate hydrochloride, fluperamide, lidamidine hydrochloride, loperamide hydrochloride, malethamer, nufenoxole, paregoric.

Antipneumocystic: atovaquone.

Antiproliferative agent: piritrexim isethionate.

Antiprostatic hypertrophy: sitogluside.

Antiprotozoal: amodiaquine, azanidazole, bamidazole, camidazole, chlortetracycline bisulfate, chlortetracycline hydrochloride, flubendazole, flunidazole, halofuginone hydrobromide, imidocarb hydrochloride, ipronidazole, metronidazole, misonidazole, moxnidazole, nitarsone, partricin, puromycin, puromycin hydrochloride, ronidazole, sulnidazole, tinidazole.

Antipruritic: cyproheptadine hydrochloride, methdilazine, methdilazine hydrochloride, trimeprazine tartrate.

Antipsoriatic: acitretin, anthralin, azaribine, calcipotriene, cycloheximide, enazadrem phosphate, etretinate, liarozole fumarate, lonapalene, tepoxalin.

Antipsychotic: acetophenazine maleate, alentemol hydrobromide, alpertine, azaperone, batelapine maleate, benperidol, benzindopyrine hydrochloride, brofoxine, bromperidol, bromperidol decanoate, butaclamol hydrochloride, butaperazine, butaperazine maleate, carphenazine maleate, carvotroline hydrochloride, chlorpromazine, chlorpromazine hydrochloride, chlorprothixene, cinperene, cintriamide, clomacran phosphate, clopenthixol, clopimozide, clopipazan mesylate, cloroperone hydrochloride, clothiapine, clothixamide maleate, clozapine, cyclophenazine hydrochloride, droperidol, etazolate hydrochloride, fenimide, flucindole, flumezapine, fluphenazine decanoate, fluphenazine enanthate, fluphenazine hydrochloride, fluspiperone, fluspirilene, flutroline, gevotroline hydrochloride, halopemide, haloperidol, haloperidol decanoate, iloperidone, imidoline hydrochloride, lenperone, mazapertine succinate, mesoridazine, mesoridazine besylate, metiapine, milenperone, milipertine, molindone hydrochloride, naranol hydrochloride, neflumozide hydrochloride, ocaperidone, olanzapine, oxiperomide, penfluridol, pentiapine maleate, perphenazine, pimozide, pinoxepin hydrochloride, pipamperone, piperacetazine, pipotiazine palniitate, piquindone hydrochloride, prochlorperazine edisylate, prochlorperazine maleate, promazine hydrochloride, remoxipride, remoxipride hydrochloride, rimcazole hydrochloride, seperidol hydrochloride, sertindole, setoperone, spiperone, thioridazine, thioridazine hydrochloride, thiothixene, thiothixene hydrochloride, tioperidone hydrochloride, tiospirone hydrochloride, trifluoperazine hydrochloride, trifluperidol, triflupromazine, triflupromazine hydrochloride, ziprasidone hydrochloride.

Antirheumatic: auranofin, aurothioglucose, bindarit, lobenzarit sodium, phenylbutazone, pirazolac, prinomide tromethamine, seprilose.

Antischistosomal: becanthone hydrochloride, hycanthone, lucanthone hydrochloride, niridazole, oxamniquine, pararosaniline pamoate, teroxalene hydrochloride.

Antiseborrheic: chloroxine, piroctone, piroctone olamine, resorcinol monoacetate, antisecretory: arbaprostil, deprostil, fenoctimine sulfate, octreotide, octreotide acetate, omeprazole sodium, rioprostil, trimoprostil.

Antispasmodic: stilonium iodide, tizanidine hydrochloride.

Antithrombotic: anagrelide hydrochloride, bivalirudin, dalteparin sodium, danaparoid sodium, dazoxiben hydrochloride, efegatran sulfate, enoxaparin sodium, ifetroban, ifetroban sodium, tinzaparin sodium, trifenagrel.

Antitussive: benzonatate, butamirate citrate, chlophedianol hydrochloride, codeine polistirex, codoxime, dextromethorphan, dextromethorphan hydrobromide, dextromethorphan polistirex, ethyl dibunate, guaiapate, hydrocodone bitartrate, hydrocodone polistirex, levopropoxyphene napsylate, noscapine, pemerid nitrate, pipazethate, suxemerid sulfate.

Anti-ulcerative: aceglutamide aluminum, cadexomer iodine, cetraxate hydrochloride, enisoprost, isotiquimide, lansoprazole, lavoltidine succinate, misoprostol, nizatidine, nolinium bromide, pantoprazole, pifarnine, pirenzepine hydrochloride, rabeprazole sodium, remiprostol, roxatidine acetate hydrochloride, sucralfate, sucrosofate potassium, tolimidone.

Anti-urolithic: cysteamine, cysteamine hydrochloride, tricitrates.

Appetite suppressant: dexfenfluramine hydrochloride, phendimetrazine tartrate, phentermine hydrochloride.

Benign prostatic hyperplasia therapy agent: tamsulosin hydrochloride.

Blood glucose regulators: human insulin, glucagon, tolazamide, tolbutamide, chloropropamide, acetohexamide and glipizide.

Bone resorption inhibitor: alendronate sodium, etidronate disodium, pamidronate disodium.

Bronchodilator: albuterol, albuterol sulfate, azanator maleate, bamifylline hydrochloride, bitolterol mesylate, butaprost, carbuterol hydrochloride, clorprenaline hydrochloride, colterol mesylate, doxaprost, doxofylline, dyphylline, enprofylline, ephedrine, ephedrine hydrochloride, fenoterol, fenprinast hydrochloride, guaithylline, hexoprenaline sulfate, hoquizil hydrochloride, ipratropium bromide, isoetharine, isoetharine hydrochloride, isoetharine mesylate, isoproterenol hydrochloride, isoproterenol sulfate, metaproterenol polistirex, metaproterenol sulfate, nisbuterol mesylate, oxtriphylline, picumeterol fumarate, piquizil hydrochloride, pirbuterol acetate, pirbuterol hydrochloride, procaterol hydrochloride, pseudoephedrine sulfate, quazodine, quinterenol sulfate, racepinephrine, racepinephrine hydrochloride, reproterol hydrochloride, rimiterol hydrobromide, salmeterol, salmeterol xinafoate, soterenol hydrochloride, sulfonterol hydrochloride, suloxifen oxalate, terbutaline sulfate, theophylline, xanoxate sodium, zindotrine, zinterol hydrochloride.

Carbonic anhydrase inhibitor: acetazolamide, acetazolamide sodium, dichlorphenamide, dorzolamide hydrochloride, methazolamide, sezolamide hydrochloride.

Cardiac depressant: acecamide hydrochloride, acetylcholine chloride, actisomide, adenosine, amiodarone, aprindine, aprindine hydrochloride, artilide fumarate, azimilide Dihydrochloride, bidisomide, bucamide maleate, bucromarone, butoprozine hydrochloride, capobenate sodium, capobenic acid, cifenline, cifenline succinate, clofilium phosphate, disobutamide, disopyramide, disopyramide phosphate, dofetilide, drobuline, edifolone acetate, emilium tosylate, encamide hydrochloride, flecamide acetate, ibutilide fumarate, indecamide hydrochloride, ipazilide fumarate, lorajmine hydrochloride, lorcamide hydrochloride, meobentine sulfate, mexiletine hydrochloride, modecamide, moricizine, oxiramide, pirmenol hydrochloride, pirolazamide, pranolium chloride, procainamide hydrochloride, propafenone hydrochloride, pyrinoline, quindonium bromide, quinidine gluconate, quinidine sulfate, recainam hydrochloride, recainam tosylate, risotilide hydrochloride, ropitoin hydrochloride, sematilide hydrochloride, suricamide maleate, tocamide, tocamide hydrochloride, transcamide.

Cardioprotectant: dexrazoxane, draflazine.

Cardiotonic: actodigin, aminone, bemoradan, butopamine, carbazeran, carsatrin succinate, deslanoside, digitalis, digitoxin, digoxin, dobutamine, dobutamine hydrochloride, dobutamine lactobionate, dobutamine tartrate, enoximone, imazodan hydrochloride, indolidan, isomazole hydrochloride, levdobutamine lactobionate, lixazinone sulfate, medorinone, milrinone, pelrinone hydrochloride, pimobendan, piroximone, prinoxodan, proscillaridin, quazinone, tazolol hydrochloride, vesnarinone.

Cardiovascular agent: dopexamine, dopexamine hydrochloride.

Choleretic: dehydrocholic acid, fencibutirol, hymecromone, piprozolin, sincalide, tocamphyl.

Cholinergic: aceclidine, bethanechol chloride, carbachol, demecarium bromide, dexpanthenol, echothiophate iodide, isofluorophate, methacholine chloride, neostigmine bromide, neostigmine methylsulfate, physostigmine, physostigmine salicylate, physostigmine sulfate, pilocarpine, pilocarpine hydrochloride, pilocarpine nitrate, pyridostigmine bromide.

Cholinergic agonist: xanomeline, xanomeline tartrate.

Cholinesterase deactivator: obidoxime chloride, pralidoxime chloride, pralidoxime iodide, pralidoxime mesylate.

Coccidiostat: arprinocid, narasin, semduramicin, semduramicin sodium.

Dognition adjuvant: ergoloid mesylates, piracetam, pramiracetam hydrochloride, pramiracetam sulfate, tacrine hydrochloride.

Cognition enhancer: besipirdine hydrochloride, linopirdine, sibopirdine.

Depressant: omeprazole.

Diagnostic aid: aminohippurate sodium, anazolene sodium, arclofenin, arginine, bentiromide, benzylpenicilloyl polylysine, butedronate tetrasodium, butilfenin, coccidioidin, corticorelin ovine triflutate, corticotropin, repository, corticotropin zinc hydroxide, diatrizoate meglumine, diatrizoate sodium, diatrizoic acid, diphtheria toxin for schick test, disofenin, edrophonium chloride, ethiodized oil, etifenin, exametazime, ferristenc, ferumoxides, ferumoxsil, fluorescein, fluorescein sodium, gadobenate dimeglumine, gadoteridol, gadodiamide, gadopentetate dimegiumine, gadoversetamide, histoplasmin, impromidine hydrochloride, indigotindisulfonate sodium, indocyanine green, iobenguane sulfate $I^{123}$, iobenzamic acid, iocarmate meglumine, locarmic acid, iocetamic acid, iodamide, lodamide megiumine, iodipamide meglumine, iodixanol, iodoxamate meglumine, iodoxamic acid, ioglicic acid, ioglucol, ioglucomide, ioglycamic acid, iogulamide, lohexyl, iomeprol, iopamidol, iopanoic acid, iopentol, iophendylate, iprofenin, iopronic acid, ioprocemic acid, iopydol, iopydone, iosefamic acid, ioseric acid, iosulamide meglumine, iosumetic acid, iotasul, iotetric acid, iothalamate meglumine, iothalamate sodium, iothalamic acid, iotrolan, iotroxic acid, ioversol, ioxaglate meglumine, ioxagiate sodium, ioxaglic acid, ioxilan, ioxotrizoic acid, ipodate calcium, ipodate sodium, isosulfan blue, leukocyte typing serum, lidofenin, mebrofenin, meglumine, metrizamide, metrizoate sodium, metyrapone, metyrapone tartrate, mumps skin test antigen, pentetic acid, propyliodone, quinaldine blue, sermorelin acetate, sodium iodide $I^{123}$, sprodiamide, stannous pyrophosphate, stannous sulfur colloid, succimer, teriparatide acetate, tetrofosmin, tolbutamide sodium, tuberculin, tyropanoate sodium, xylose.

Diuretic: ambuphylline, ambuside, amiloride hydrochloride, azolimine, azosemide, brocrinat, bumetanide, chlorothiazide, chlorthalidone, clazolimine, clorexolone, ethacrynate sodium, ethacrynic acid, etozolin, fenquizone, furosemide, hydrochlorothiazide, isosorbide, mannitol, mefruside, ozolinone, piretanide, spiroxasone, torsemide, triamterene, triflocin, urea.

Dopaminergic agent: ibopamine.

Ectoparasiticide: nifluridide, permethrin.

Emetic: apomorphine hydrochloride.

Enzyme inhibitor: acetohydroxamic acid, alrestatin sodium, aprotinin, benazepril hydrochloride, benazeprilat, benurestat, bromocriptine, bromocriptine mesylate, cilastatin sodium, fluorofamide, lergotrile, lergotrile mesylate, levcycloserine, libenzapril, pentopril, pepstatin, perindopril, polignate sodium, sodium amylosulfate, sorbinil, spirapril hydrochloride, spiraprilat, taleranol, teprotide, tolfamide, zofenopril calcium.

Estrogen: chlorotrianisene, dienestrol, diethylstilbestrol, diethylstilbestrol diphosphate, equilin, estradiol, estradiol cypionate, estradiol enanthate, estradiol undecylate, estradiol valerate, estrazinol hydrobromide, estriol, estrofurate, estrogens, conjugated, estrogens, esterified, estrone, estropipate, ethinyl estradiol, fenestrel, mestranol, nylestriol, quinestrol.

Fibrinolytic: anistreplase, bisobrin lactate, brinolase.

Free oxygen radical scavenger: pegorgotein.

Gastrointestinal motility agents: cisapride (PROPULSID™), metoclopramide (REGLAN™), hyoscyamine (LEVSIN™).

Glucocorticoid: amcinonide, beclomethasone dipropionate, betamethasone, betamethasone acetate, betamethasone benzoate, betamethasone dipropionate, betamethasone sodium phosphate, betamethasone valerate, carbenoxolone sodium, clocortolone acetate, clocortolone pivalate, cloprednol, corticotropin, corticotropin, repository, corticotropin zinc hydroxide, cortisone acetate, cortivazol, descinolone acetonide, dexamethasone, dexamethasone sodium phosphate, diflucortolone, diflucortolone pivalate, flucloronide, flumethasone, flumethasone pivalate, flunisolide, fluocinolone acetonide, fluocinonide, fluocortolone, fluocortolone caproate, fluorometholone, fluperolone acetate, fluprednisolone, fluprednisolone valerate, flurandrenolide, formocortal, hydrocortisone, hydrocortisone acetate, hydrocortisone buteprate, hydrocortisone butyrate, hydrocortisone sodium phosphate, hydrocortisone sodium succinate, hydrocortisone valerate, medrysone, methylprednisolone, methylprednisolone acetate, methylprednisoloime sodium phosphate, methylprednisolone sodium succinate, nivazol, paramethasone acetate, prednicarbate, prednisolone, prednisolone acetate, prednisolone hemisuccinate, prednisolone sodium phosphate, prednisolone sodium succinate, prednisolone tebutate, prednisone, prednival, ticabesone propionate, tralonide, triamcinolone, triamcinolone acetonide, triamcinolone acetonide sodium, triamcinolone diacetate, triamcinolone hexacetonide.

Gonad-stimulating principle: buserelin acetate, clomiphene citrate, ganirelix acetate, gonadorelin acetate, gonadorelin hydrochloride, gonadotropin, chorionic, menotropins.

Hair growth stimulant: minoxidil.

Hemostatic: aminocaproic acid, oxamarin hydrochloride, sulmarin, thrombin, tranexarnic acid.

Histamine H2 receptor antagonists: ranitidine (ZANTAC™), famotidine (PEPCID™), cimetidine (TAGAMET™), nizatidine (AXID™).

Hormone: diethylstilbestrol, progesterone, 17 hydroxy progesterone, medroxyprogesterone, norgestrel, norethynodrel, estradiol, megestrol (megace), norethindrone, levonorgestrel, ethyndiol, ethinyl estradiol, mestranol, estrone, equilin, 17 alpha dihydroequilin, equilenin, 17 alpha dihydroequilenin, 17 alpha estradiol, 17 beta estradiol, leuprolide (LUPRON™), glucagon, testolactone, clomiphene, human menopausal gonadotropins, human chorionic gonadotropin, urofollitropin, bromocriptine, gonadorelin, luteinizing hormone releasing hormone and analogs, gonadotropins, danazol, testosterone, dehydroepiandrosterone, androstenedione, dihydroestosterone, relaxin, oxytocin, vasopressin, folliculostatin, follicle regulatory protein, gonadoctrinins, oocyte maturation inhibitor, insulin growth factor, follicle stimulating hormone, luteinizing hormone, tamoxifen, corticorelin ovine triftutate, cosyntropin, metogest, pituitary, posterior, seractide acetate, somalapor, somatrem, somatropin, somenopor, somidobove.

Hypocholesterolemic: lifibrol.

Hypoglycemic: darglitazone sodium: glimepiride.

Hypolipidemic: azalanstat dihydrochloride, colestolone, surfomer, xenalipin.

Hypotensive: viprostol.

Hmgcoa reductase inhibitors: lovastatin (MEVACOR™), simvastatin (ZOCOR™), pravastatin (PRAVACHOL™), fluvasatin (LESCOL™).

Immunizing agent: antirabies serum, antivenin (*latrodectus mactans*), antivenin (*micrurus fulvius*), antivenin (*crotalidae*) polyvalent, BCG vaccine, botulism antitoxin, cholera vaccine, diphtheria antitoxin, diphtheria toxoid, diphtheria toxoid adsorbed, globulin, immune, hepatitis b immune globulin, hepatitis B virus vaccine inactivated, influenza virus vaccine, measles virus vaccine live, meningococcal polysaccharide vaccine group A, meningococcal polysaccharide vaccine group C, mumps virus vaccine live, pertussis immune globulin, pertussis vaccine, pertussis vaccine adsorbed, plague vaccine, poliovirus vaccine inactivated, poliovirus vaccine live oral, rabies immune globulin, rabies vaccine, $Rh_o$ (D) immune globulin, rubella virus vaccine live, smallpox vaccine, tetanus antitoxin, tetanus immune globulin, tetanus toxoid, tetanus toxoid adsorbed, typhoid vaccine, yellow fever vaccine, vaccinia immune globulin, varicella-zoster immune globulin.

Immunomodulator: dimepranol acedoben, imiquimod, interferon beta-Ib, lisofylline, mycophenolate mofetil, prczatide copper acetate.

Immunoregulator: azarole, fanetizole mesylate, frentizole, oxamisole hydrochloride, ristianol phosphate, thymopentin, tilomisole.

Immunostimulant: loxoribine, teceleukin.

Immunosuppressant: azathioprine, azathioprine sodium, cyclosporine, daltroban, gusperimus trihydrochloride, sirolimus, tacrolimus.

Impotence therapy adjunct: delequamine hydrochloride.

Inhibitor: acarbose, atorvastatin calcium, benserazide, brocresine, carbidopa, clavulanate potassium, dazmegrel, docebenone, epoprostenol, epoprostenol sodium, episteride, finasteride, flurbiprofen sodium, furegrelate sodium, lufironil, miglitol, orlistat, pimagedine hydrochloride, pirmagrel, ponalrestat, ridogrel, sulbactam benzathine, sulbactampivoxil, sulbactam sodium, suronacrine maleate, tazobactam, tazobactam sodium, ticlopidine hydrochloride, tirilazad mesylate, tolrestat, velnacrine maleate, zifrosilone, zileuton.

Keratolytic: alcloxa, aldioxa, benzoyl peroxide, dibenzothiophene, etarotene, isotretinoin, motretinide, picotrin diolamine, resorcinol, resorcinol monoacetate, salicylic acid, sumarotene, tazarotene, tetroquinone, tretinoin.

LHRL agonist: deslorelin, goserelin, histrelin, lutrelin acetate, nafarelin acetate.

Liver disorder treatment: malotilate.

Luteolysin: fenprostalene.

Memory adjuvant: dimoxamine hydrochloride, ribaminol.

Mental performance enhancer: aniracetam.
Mood regulator: fengabine.
Mucolytic: acetylcysteine, carbocysteine, domiodol.
Mucosal protective agents: misoprostol (CYTOTEC™).
Mydriatic: berefrine.
Nasal decongestant: nemazoline hydrochloride, pseudoephedrine polistirex.
Neuroleptic: duoperone fumarate, risperidone.
Neuromuscular blocking agent: atracurium besylate, cisatracurium besylate, doxacurium chloride, gallamine triethiodide, metocurine iodide, mivacurium chloride, pancuronium bromide, pipecuronium bromide, rocuronium bromide, succinylcholine chloride, tubocurarine chloride, vecuronium bromide.
Neuroprotective: dizocilpine maleate.
NMDA antagonist: selfotel.
Non-hormonal sterol derivative: pregnenolone succinate.
Oxytocic: carboprost, carboprost methyl, carboprost tromethamine, dinoprost, dinoprost tromethamine, dinoprostone, ergonovine maleate, meteneprost, methylergonovine maleate, oxytocin, sparteine sulfate.
Plasminogen activator: alteplase, urokinase.
Platelet activating factor antagonist: lexipafant.
Platelet aggregation inhibitor: acadesine, beraprost, beraprost sodium, ciprostene calcium, itazigrel, lifarizine, oxagrelate.
Post-stroke and post-head trauma treatment: citicoline sodium.
Potentiator: pentostatin, talopram hydrochloride.
Progestin: algestone acetophenide, amadinone acetate, anagestone acetate, chlormadinone acetate, cingestol, clogestone acetate, clomegestone acetate, desogestrel, dimethisterone, dydrogesterone, ethynerone, ethynodiol diacetate, etonogestrel, fluorogestone acetate, gestaclone, gestodene, gestonorone caproate, gestrinone, haloprogesterone, hydroxyprogesterone caproate, levonorgestrel, lynestrenol, medrogestone, medroxyprogesterone acetate, methynodiol diacetate, norethindrone, norethindrone acetate, norethynodrel, norgestimate, norgestomet, norgestrel, oxogestone phenpropionate, progesterone, quingestanol acetate, quingestrone, tigestol.
Prostaglandin: cloprostenol sodium, fluprostenol sodium, gemeprost, prostalene, sulprostone.
Prostate growth inhibitor: pentomone.
Prothyrotropin: protirelin.
Psychotropic: minaprine.
Pulmonary surface: beractant, colfosceril palmitate.
Radioactive agent: fibrinogen $I^{125}$, fludeoxyglucose $F^{18}$, fluorodopa $F^{18}$, insulin $I^{125}$, insulin $I^{131}$, iobenguane $I^{123}$, iodipamide sodium $I^{131}$, iodoantipyrine $I^{131}$, iodocholesterol $I^{131}$, iodohippurate sodium $I^{123}$, iodohippurate sodium $I^{125}$, iodohippurate sodium $I^{131}$, iodopyracet $I^{125}$, iodopyracet $I^{131}$, iofetamine hydrochloride $I^{123}$, iomethin $I^{125}$, iomethin $I^{131}$, iothalamate sodium $I^{125}$, iothalamate sodium $I^{131}$, iotyrosine $I^{131}$, liothyronine $I^{125}$, liothyronine $I^{131}$, merisoprol acetate $Hg^{197}$, merisoprol acetate $Hg^{203}$, merisoprol $Hg^{197}$, selenomethionine $Se^{75}$, technetium $Tc^{99m}$ antimony trisulfide colloid, technetium $Tc^{99m}$ bicisate, technetium $Tc^{99m}$ disofenin, technetium $Tc^{99m}$ etidronate, technetium $Tc^{99m}$ exametazime, technetium $Tc^{99m}$ furifosmin, technetium $Tc^{99m}$ gluceptate, technetium $Tc^{99m}$ lidofenin, technetium $Tc^{99m}$ mebrofenin, technetium $Tc^{99m}$ medronate, technetium $Tc^{99m}$ medronate disodium, technetium $Tc^{99m}$ mertiatide, technetium $Tc^{99m}$ oxidronate, technetium $Tc^{99m}$ pentetate, technetium $Tc^{99m}$ pentetate calcium trisodium, technetium $Tc^{99m}$ sestamibi, technetium $Tc^{99m}$ siboroxime, technetium $Tc^{99m}$ succimer, technetium $Tc^{99m}$ sulfur colloid, technetium $Tc^{99m}$ teboroxime, technetium $Tc^{99m}$ tetrofosmin, technetium $Tc^{99m}$ tiatide, thyroxine $I^{125}$, thyroxine $I^{131}$, tolpovidone $I^{131}$, triolein $I^{125}$, triolein $I^{131}$.
Regulator: calcifediol, calcitonin, calcitriol, clodronic acid, dihydrotachysterol, etidronic acid, oxidronic acid, piridronate sodium, risedronate sodium, secalciferol.
Relaxant: adiphenine hydrochloride, alcuronium chloride, aminophylline, azumolene sodium, baclofen, benzoctamine hydrochloride, carisoprodol, chlorphenesin carbamate, chlorzoxazone, cinflumide, cinnamedrine, clodanolene, cyclobenzaprine hydrochloride, dantrolene, dantrolene sodium, fenalamide, fenyripol hydrochloride, fetoxylate hydrochloride, flavoxate hydrochloride, fletazepam, flumetramide-flurazepam hydrochloride, hexafluorenium bromide, isomylamine hydrochloride, lorbamate, mebeverine hydrochloride, mesuprine hydrochloride, metaxalone, methocarbamol, methixene hydrochloride, nafomine malate, nelezaprine maleate, papaverine hydrochloride, pipoxolan.
Hydrochloride, quinctolate, ritodrine, ritodrine hydrochloride, rolodine, theophylline sodium glycinate, thiphenamil hydrochloride, xilobam.
Repartitioning agent: cimaterol.
Scabicide: amitraz, crotamiton.
Sclerosing agent: ethanolamine oleate, morrhuate sodium, tribenoside.
Sedative: propiomazine.
Sedative-hypnotic: allobarbital, alonimid, alprazolam, amobarbital sodium, bentazepam, brotizolam, butabarbital, butabarbital sodium, butalbital, capuride, carbocloral, chloral betaine, chloral hydrate, chlordiazepoxide hydrochloride, cloperidone hydrochloride, clorethate, cyprazepam, dexclamol hydrochloride, diazepam, dichloralphenazone, estazolam, ethchlorvynol, etomidate, fenobam, flunitrazepam, fosazepam, glutethimide, halazepam, lormetazepam, mecloqualone, meprobamate, methaqualone, midaflur, paraldehyde, pentobarbital, pentobarbital sodium, perlapine, prazepam, quazepam, reclazepam, roletamide, secobarbital, secobarbital sodium, suproclone, thalidomide, tracazolate, trepipam maleate, triazolam, tricetamide, triclofos sodium, trimetozine, uldazepam, zaleplon, zolazepam hydrochloride, zolpidem tartrate.
Selective adenosine al antagonist: apaxifylline.
Serotonin antagonist: altanserin tartrate, amesergide, ketanserin, ritanserin.
Serotonin inhibitor: cinanserin hydrochloride, fenclonine, fonazine mesylate, xylamidine tosylate.
Serotonin receptor antagonist: tropanserin hydrochloride.
Steroid: dexamethasone aceflrate, mometasone furoate.
Stimulant: amfonelic acid, amphetamine sulfate, ampyzine sulfate, arbutamine hydrochloride, azabon, caffeine, ceruletide, ceruletide diethylamine, cisapride, dazopride fumarate, dextroamphetamine, dextroamphetamine sulfate, difluanine hydrochloride, dimefline hydrochloride, doxapram hydrochloride, etryptamine acetate, ethamivan, fenethylline hydrochloride, flubanilate hydrochloride, fluorothyl, histamine phosphate, indriline hydrochloride, mefexamide, methamphetamine hydrochlo ride, methylphenidate hydrochloride, pemoline, pyrovalerone hydrochloride, xamoterol, xamoterol fumarate.
Suppressant: amfhutizole, coxchicine, tazofelone.
Symptomatic multiple sclerosis: fampridine.
Synergist: proadifen hydrochloride.
Thyroid hor move: levothyroxine sodium, liothyronine sodium, liotrix.
Thyroid inhibitor: methimazole, propylthiouracil.
Thyromimetic: thyromedan hydrochloride.

Tranquilizer: bromazepam, buspirone hydrochloride, chlordiazepoxide, clazolam, clobazam, clorazepate dipotassium, clorazepate monopotassium, demoxepam, dexmedetomidine, enciprazine hydrochloride, gepirone hydrochloride, hydroxyphenamate, hydroxyzine Hydrochloride, hydroxyzine pamoate, ketazolam, lorazepam, lorzafone, loxapine, loxapine succinate, medazepam hydrochloride, nabilone, nisobamate, oxazepam, pentabamate, pirenperone, ripazepam, rolipram, sulazepam, taciamine hydrochloride, temazepam, triflubazam, tybamate, valnoctamide.

Amyotrophic lateral sclerosis agents: riluzole.
Cerebral ischemia agents: dextrorphan hydrochloride.
Paget's disease agents: tiludronate disodium.
Unstable angina agents: tirofiban hydrochloride.
Uricosuric: benzbromarone, irtemazole, probenecid, sulfinpyrazone.
Vasoconstrictor: angiotensin amide, felypressin, methysergide, methysergide maleate.
Vasodilator: alprostadil, azaclorzine hydrochloride, bamethan sulfate, bepridil hydrochloride, buterizine, cetiedil citrate, chromonar hydrochloride, clonitrate, diltiazem hydrochloride, dipyridamole, droprenilamine, erythrityl tetranitrate, felodipine, flunarizine hydrochloride, fostedil, hexobendine, inositol niacinate, iproxamine hydrochloride, isosorbide dinitrate, isosorbide mononitrate, isoxsuprine hydrochloride, lidoflazine, mefenidil, mefenidil fumarate, mibefradil dihydrochloride, mioflazine hydrochloride, mixidine, nafronyl oxalate, nicardipine hydrochloride, nicergoline, nicorandil, nicotinyl alcohol, nifedipine, nimodipine, nisoldipine, oxfenicine, oxprenolol hydrochloride, pentaerythritol tetranitrate, pentoxifylline, pentrinitrol, perhexyline maleate, pindolol, pirsidomine, prenylamine, propatyl nitrate, suloctidil, terodiline hydrochloride, tipropidil hydrochloride, tolazoline hydrochloride, xanthinol niacinate.
Vulnerary: allantoin.
Wound healing agent: ersofermin.
Xanthine oxidase inhibitor: allopurinol, oxypurinol.
Other pharmaceutical agents include: 1-decpyrrolidinone, 1-dodecpyrrolidinone, 16α-fluoroestradiol, 16-epiestriol, 16α-gitoxin, 17α estradiol, 17β estradiol, 1alpha-hydroxyvitamin D2,2'-nor-cGMP, 20-epi-1,25 dihydroxyvitamin D3, 22-oxacalcitriol, 2CVV, 3-isobutyl GABA, 6-FUDCA, 7-methoxytacrine, abamectin, abanoquil, abecamil, abiraterone, acadesine, acamprosate, acarbose, aceclofenac, acemannan, acetomepregenol, acetyl-L-carnitine, acetylcysteine, N-acetylmethadol, acifran, acipimox, acitemate, acitretin, aclarubicin, aclatonium, napadisilate, aconiazide, acrivastinet, adafenoxate, adapalene, adatanserin, adecypenol, adefovir dipivoxil, adelmidrol, ademetionine, adinazolam, adiposin, adozelesin, adrafinil, alacepril, aladapcin, alaptide, albendazole, albolabrin, aldecalmycin, aldesleukin, alendronic acid, alentemol, alfacalcidol, alfuizosin, alglucerase, alinastine, alosetron, alpha idosone, alprostadil, altretamine, altromycin B, ambamustine, amelometasone, amesergide, amezinium metilsulfate, amfebutamone, amidox, amifloxacin, amifostine, amiodarone, amisulpride, amlexanox, amlodipine, amlodipine, ampiroxicam, aminone, amrubicin, amsacrine, amylin, amythiamicin, anagrelide, anakinra, ananain, anaritide, anastrozole, andrographolide, anordrin, apadoline, apafant, apaxifylline, aphidicolin glycinate, apraclonidine, aprosulate sodium, aptiganel, apurinic acid, aranidipine, arbekacin, arbidol, arbutamine, ardeparin sodium, arecatannin B1, argatroban, aripiprazol, arotinolol, asimadoline, aspalatone, asperfuran, aspoxicillin, astemizole, asulacrine, atamestanie, atenolol, S-atevirdine, atosiban, atovaquone, atpenin B, atrimustine, atrinositol, aureobasidin A, azadirachtine, azasetron, azatyrosine, azelaic acid, azelastine, azelnidipine, azimilide, azithromycin, azosemide, aztreonam, baccatin III, bacoside A, bacoside B, bactobolamine, balazipone, balhimycin, balofloxacin, balsalazide, bambuterol, baohuoside 1, bamidipine, basifungin, batebulast, batimastat, beauvericin, becaplermin, becliconazole, befloxatone, belfosdil, bellenamine, benflumetol, benidipine, benzisoxazole, benzochlorins, benzoidazoxan, benzoylstaurosporine, benztropine, bepridil, beractant, beraprost, berlafenone, bertosamil, besipirdine, beta-alethine, betaclamycin B, betamipron, betaxolol, betulinic acid, bevantolol, bicalutamide, bifemelane, bimakalim, bimithil, binospirone, bioxalomycin alpha2, biriperone, bis-benzimidazole A, bis-benzimidazole B, bisantrene, bisaramil, bisaziridinylspermine, bisnafide, bisoprolol, bistramide D, bistramide K, bistratene A, boldine, bopindolol, brefeldin, breflate, brimonidine, bromfenac, bromperidol, bropirimine, bucindolol, budesonide, budipine, budotitane, bunaprolast, bunazosin, butenafine, buthionine sulfoximine, butixocort propionate, cadexomer iodine, calanolide A, calcipotriol, calphostin C, camonagrel, candesartan, candesartan cilexetil, candoxatril, candoxatrilat, capecitabine, capromab, capsaicin, captopril, carbazomycin C, carbetocin, carbovir, carboxamide-amino-triazole, carboxyamidotriazole, carboxymethylated β-1,3-glucan, carperitide, carteolol, carumonam, carvedilol, carvotroline, carzelesin, castanospermine, cebaracetam, cecropin B, cefcapene pivoxil, cefdaloxime pentexil tosilate, cefdinir, cefditoren pivoxil, cefepime, cefetamet, cefetamet pivoxil, cefixime, cefluprenam, cefmnetazole, cefmninox, cefodizime, cefoselis, cefotetan, cefotiam, cefotiam hexetil, cefozopran, cefpimizole, cefpiramide, cefpirome, cefpodoxime proxetil, cefprozil, cefsulodin, cefteram, ceftibuten, cefriaxone, cefuroxime axetil, celastrol, celikalim, celiprolol, cepacidine A, cericlamine, cerivastatin, ceronapril, certoparin sodium, cetiedil, cetirizine, chloroorienticin A, chloroorienticin B, chloroquinoxaline sulfonamide, cibenzoline, cicaprost, ciclesonide, cicletanine, cicloprolol, cidofovir, cilansetron, cilazapril, cilnidipine, cilobradine, cilostazol, cimetropium bromide, cinitapride, cinolazepam, cioteronel, ciprofibrate, ciprofloxacin, ciprostene, cis-porphyrin, cisapride, cisatracurium besilate, cistinexine, citalopram, citicoline, citreamicin alpha, cladribine, clarithromycin, clausenamide, clebopride, clinafloxacin, clobazam, clobetasone butyrate, clodronic acid, clomethiazole, clopidogrel, clotrimazole, colestimide, colfosceril palmitate, collismycin A, collismycin B, combretastatin A4, complestatin, conagenin, contignasterol, contortrostatin, cosalane, costatolide, cotinine, coumermycin A1, cucumariosid, curacin A, curdlan sulfate, curiosin, cyclazosin, cyclic HPMPC, cyclobenzaprine, cyclobut A, cyclobut G, cyclocapron, cycloplatam, cyclosin, cyclothialidine, cyclothiazomycin, cypemycin, cyproterone, cytarabine ocfosfate, cytochalasin B, dacliximab, dactimicin, daidzein, daidzin, dalfopristin, dalteparin sodium, danaparoid, daphnodorin A, dapiprazole, dapitant, darifenacin, darlucin A, darsidomine, ddUTP, decitabine, deferiprone, deflazacort, dehydrodidemnin B, dehydroepiandrosterone, delapril, delequamine, delfaprazine, delmopinol, delphinidin, deoxypyridinoline, deprodone, depsidomycin, deramciclane, dermatan sulfate, desflurane, desirudin, deslorelin, desmopressin, desogestrel, desoxoarniodarone, detajmium bitartrate, dexifosfamide, dexketoprofen, dexloxiglumide, dexmedetomidine, dexpemedolac, dexrazoxane, dexsotalol, dextrin 2-sulphate, dexverapamil, dezinamide, dezocine, diaziquone, diclofenac digolil, diclofenac potassium, dicranin, didemnin B, didox, dienogest, diethylhomospermine, diethylnorspermine, dihydrexidine, dihydro-5-azacytidine, dimethyl prostaglandin A1, dimethylhomospermine, dimiracetam, dioxamycin, diphencyprone, diphenyl spiromustine, diprafenone, dipropylnorspermine, dirithromycin, discodermolide, disulfuram, ditekiren, docarpamine, docosanol, 1-dofetilide, dolasetron, domitroban, dopexamine, dorzolamide, dosmalfate, dotarizine, doxacurium chloride, doxazosin, doxifluridine, doxofylline, draculin, draflazine, droloxifene, dronabinol, drosperidone, drotaverine acephyllinate, droxicam, ebiratide, ebrotidine, ebselen, ecabapide, ecabet, ecadotril, ecdisteron, echicetin, echistatin, ecomustine, ecteinascidin 722, ecteinascidin 729, ecteinascidin 743, edaravone, edelfosine, edobacomab, edrecolomab, efegatran, eflornithine, efonidipine, egualen, elcatonin, eletriptan, elgodipine, eliprodil, eltenac, emakalim, emedastine, emiglitate, emitefur, emoctakin, enadoline hydrochloride, enalapril, enazadrem, englitazone, enlimomab, enoxacin, enoxaparin sodium, enoximone, entacapone, enterostatin, epoprostenol, epoxymexrenone, epristeride, eprosartan, eptastigmine, erdosteine, ersentilide, ersofermin, erytlritol, esuprone, etanidazole, etanterol, ethacizin, ethinylestradiol, etizolam, etodolac, etoposide phosphate, etrabamine, everninomicin, examorelin, exemestane, fadrozole, faeriefungin, famciclovir, fampridine, fantofarone, faropenem, fasidotril, fasudil, fazarabine, fedotozine, felbamate, fenofibrate, fenoldopam, fenretinide, fenspiride, fenticonazole, fepradinol, ferpifosate sodium, ferristene, ferrixan, ferumoxsil, fexofenadine, flavopiridol, flecamide, flerobuterol, fleroxacin, flesinoxan, flezelastine, flobufen, flomoxef, florfenicol, florifenine, flosatidil, fluasterone, fluconazole, fludarabine, flumazenil, flumecinol, flumequine, flunarizine, fluocalcitriol, fluorodaunorunicin hydrochloride, fluoxetine, R-fluoxetine, S-fluparoxan, flupirtine, flurbiprofen axetil, flurithromycin, fluticasone propionate, flutrimazole, fluvastatin, fluvoxamine, forasartan, forfenimex, formestane, formoterol, formoterol, R,R-fosfomycin, trometamol, fosinopril, fosphenyloin, fostriecin, fotemustine, gabapentin, gadobenic acid, gadobutrol, gadodiamide, gadodiamide-EOB-DTPA, gadolinium texaphyrin, gadoteric acid, gadoteridol, gadoversetamide, galantamine, galdansetron, gallopamil, galocitabine, gamolenic acid, ganirelix, gepirone, gestrinone, girisopam, glaspimod, glaucocalyxin A, glutapyrone, glycopine, glycopril, granisetron, grepafloxacin, halichondrin B, halofantrine, halomon, halopredone, hatomamicin, hatomarubigin A, hatomarubigin B, hatomarubigin C, hatomarubigin D, ibogaine, ibopamine, ibudilast, illimaquinone, ilmofosine, ilomastat, iloperidone, iloprost, imidapril, imidazenil, indinavir, indolidan, indometacin farnesil, indometacin, tropine ester, indoramin, inocoterone, inogatran, inolimomab, interferon alfa, interferon alfa-2a, interferon alfa-2B, interferon alfa-N 1, interferon alfa-N3, interferon β, interferon β-1 A1, interferon β-1B, interferon gamma-1A, interferon gamma-1B, interferon omega, interferon, consensus, interleukin-1, interleukin-1 alpha, interleukin-1β, interleukin-10, interleukin-11, interleukin-12, interleukin-12, interleukin-15, interleukin-2, interleukin-3, interleukin-4, interleukin-5, interleukin-7, interleukin-8, iobenguane, iobitridol, iodoamiloride, iododoxorubicin, iofratol, iomeprol, iopentol, iopromide, iopyrol, iotriside, ioversol, ioxilan, ipazilide, IpdR, ipenoxazone, ipidacrine, ipomeanol, 4-ipriflavone, ipsapirone, irbesartan, irinotecan, irloxacin, irsogladine, irtemazole, isalsteine, isbogrel, isepamicin, isobengazole, isofloxythepin, isohomohalicondrin B, isopropyl unoprostone, isradipine, itameline, itasetron, itopride, itraconazole, ketoprofen, R-ketoprofen, S-ketorolac, lacidipine, lactitol, lactivicin, laennec, lafutidine, lamelrarin-N triacetate, lamifiban, lamivudine, lamotrigine, lanoconazole, lanperisone, lanreotide, lansoprazole, latanoprost, lateritin, laurocapram, lazabemide, lemefloxacin, lemildipine, leminoprazole, lenercept, lenograstim, lentinan sulfate, leptin, leptolstatin, lercanidipine, lerisetron, lesopitron, letrazuril, letrozole, leucomyzin, leuprorelin, levcromakalim, levetiracetam, levobetaxolol, levobunolol, levobupivacaine, levocabastine, levocamitine, levodropropizine, levofloxacin, levomoprolol, levonorgestrel, levormeloxifene, levosimendan, levosulpiride, linotroban, linsidomine, lintitript, lintopride, liothyronine sodium, lirexapride, lisinopril, lobaplatin, lobucavir, lodoxamide, lombricine, lomefloxacin, lomerizine, lometrexol, lonazolac, lonidamine, loracarbef, loratadine, lorglumide, lomoxicam, losartan, losigamone, losoxantrone, loteprednol, loviride, loxoribine, lubeluzole, lurtotecan, luteinizing hormone, lutetium, luzindole, lydicamycin, lysofylline, lysostaphin, magainin 2 amide, magnolol, mallotochromene, mallotojaponin, malotilate, mangafodipir, manidipine, maniwamycin A, mannostatin A, manumycin E, manumycin F, mapinastine, marimastat, masoprocol, maspin, massetolide, meterelin, methoxatone, methylhistamine, R-alpha, methylinosine monophosphate, methylprednisolone aceponate, methylprednisolone suleptanate, metipamide, metoclopramide, metoprolol, S-metrifonate, mibefradil, michellamine B, microcolin A, midodrine, mifepristone, miglitol, milacemide, milameline, mildronate, milnacipran, milrinone, miltefosine, minaprine, miokamycin, mipragoside, mirfentanil, mirimostim, mirtazapine, misoprostol, mitoguazone, mitolactol, mitonafide, mitoxantrone, mivacurium chloride, mivazerol, mixanpril, mizolastine, mizoribine, moclobemide, modafinil, moexipril, mofarotene, mofezolac, molgramostim, mometasone, montirelin, mopidamol, moracizine, mosapramine, mosapride, motilide, moxiraprine, moxonidine, nadifloxacin, nadroparin calcium, nafadotride, nafamostat, nafarelin, naftopidil, naglivan, nagrestip, nalmefene, naphterpin, napsagatran, naratriptan, nartograstim, nasaruplase, nateplase, niperotidine, niravoline, nisamycin, nisin, nisoldipine, nitazoxanide, nitecapone, nitrendipine, nitrendipine, S-nitrofurantoin monohydrate, nitrullyn, nizatidine, ofloxacin, okicenone, olanzapine, olopadine, olprinone, olsalazine, omeprazole, onapristone, ondansetron, ondansetron, R-ontazolast, oracin, otenzepad, oxaliplatin, oxamisole, oxandrolone, oxaprozin, oxaunomycin, oxcarbazepine, oxiconazole, oxiracetam, oxodipine, ozagrel, palauamine, palinavir, palmitoylrhizoxin, pamaqueside, pamicogrel, pamidronic acid, panamesine, panaxytriol, panipenem, panipenum, pannorin, panomifene, pantethine, pantoprazole, parabactin, pamaparin sodium, paroxetine, parthenolide, pazelliptine, pazufloxacin, pefloxacin, pegaspargase, peldesine, pemedolac, pemirolast, penciclovir, pentafuside, pentamidine, pentamorphone, pentigetide, pentosan, pentostatin, pentrozole, perflubron, perfosfamide, pergolide, perindoprilat, perospirone, phenaridine, phenazinomycin, phenserine, phensuccinal, phentolamine mesilate, phenylacetate, phenylalanyl ketoconazole, picenadol, picibanil, picroliv, picumeterol, pidotimod, pilocarpine hydrochloride, pilsicamide, pimagedine, pimilprost, pimobendan, pinacidil, pinocebrin, pioglitazone, pipecuronium bromide, pirarubicin, piretanide, pirfenidone, piritrexim, pirlindole, pirmagrel, pirmenol, pirodavir, pirodomast, piroxicam cinnamate, propagermanium, propentofylline, propionylcamitine, L-propiram, propiram+paracetamol, propiverine, propyl bis-acridone, prostaglandin J2, prostratin, protegrin, protosufloxacin, prulifloxacin, pyrazoloacridine, quazepam, quetiapine, quiflapon, quinagolide, quinapril, quinfamide, quinupristin, raloxifene, raltitrexed, ramatroban, ramipril, ramosetron, ranelic acid, ranitidine bismuth citrate, ranolazine, recainam, regavirumab, relaxin, repirinast, resinferatoxin, reticulon, reviparin sodium, revizinone, ricasetron, ridogrel, rifabutin, rifapentine, rifaximin, rilopirox, riluzole, rimantadine, rimexolone, rimoprogin, riodipine, ripisartan, risedronic acid, rispenzepine, risperidone, ritanserin, ritipenem, ritipenem acoxil, ritolukast, ritonavir, rizatriptan benzoate, rohitukine, rokitamycin, ropinirole, ropivacaine, roquinimex, roxatidine, roxindole, roxithromycin, rubiginone B1, ruboxyl, rufloxacin, rupatidine, ruzadolane, safingol, safironil, saintopin, salbutamol, R-salmeterol, salmeterol, R-sainacedin, sameridine, sampatrilat, sanfetrinem, saprisartan, sapropterin, saquinavir, sarcophytol A sargramostim, sarpogrelate, saruplase, saterinone, satigrel, satumomab pendetide, selegiline, selenium thiosemicarbazone, sematilide, semduramicin, semotiadil, semustine, sermorelin, sertaconazole, sertindole, sertraline, setiptiline, sevirumab, sevoflurane, sezolamide, silipide, silteplase, simendan, simvastatin, sinitrodil, sinnabidol, sipatrigine, sirolimus, sizofuran, somatomedin B, somatomedin C, somatrem, somatropin, sonermin, stalol, staurosporine, stavudine, stepronin, stipiamide, stiripentol, stobadine, succibun, sucralfate, sulfasalazine, sulfmosine, sulfoxamine, sulopenem, sultamicillin, sultopride, sulukast, sumatriptan, symakalim, tandospirone, tapgen, taprostene, tasosartan, tazanolast, tazarotene, teicoplanin, telenzepine, tellurapyrylium, telmesteine, telmisartan, temocapril, temoporfin, temozolomide, tenidap, teniposide, tenosal, tenoxicam, tepirindole, tepoxalin, terazosin, terbinafine, terfenadine, terflavoxate, terguride, terlakiren, terlipressin, terodiline, tertatolol, testosterone buciclate, tetrachlorodecaoxide, tetrazomine, thaliblastine, thalidomide, thiocoraline, thiofedrine, thiomarinol, thioperamide, thyroid stimulating hormone, tiagabine, tianeptine, tiapafant, tibolone, ticlopidine, tienoxolol, tilisolol, tilnoprofen arbamel, tiludronic acid, tinzaparin sodium, tiotropium bromide, tipredane, tiqueside, tirandalydigin, tirapazamine, tirilazad, tirofiban, tiropramide, topsentin, torasemide, toremifene, tosufloxacin, trafermin, trandolapril, traxanox, tretinoin, tretinoin tocoferil, triacetyluridine, tricaprilin, trichohyalin, trichosanthin, alpha, triciribine, trientine, triflavin, trimegestone, triptorelin, troglitazone, trombodipine, tropisetron, trospectomycin, trovafloxacin, trovirdine, tucaresol, tulobuterol, tylogenin, urapidil, uridine triphosphate, valaciclovir, valproate magnesium, valproate semisodium, valsartan, vamicamide, vanadeine, vaminolol, vapreotide, variolin B, velaresol, venlafaxine, veramine, verapamil, S-verdins, veroxan, verteporfin, vesnarinone, vexibinol, vigabatrin, vinbumine citrate, vinbumine resinate, vinconate, vinorelbine, vinpocetine, vinpocetine citrate, vintoperol, vinxaltine, voriconazole, vorozole, voxergolide, xemilofiban, ximoprofen, yangambin, zabicipril, zacopride, zacopride, R-zafirlukast, zalcitabine, zaleplon, zalospirone, zaltoprofen, zanamivir, zankiren, zanoterone, zatebradine, zatosetron, zenarestat, zeniplatin, zifrosilone, zilascorb, zileuton, zinostatin stimalamer, ziprasidone, zoledronic acid, zolmitriptan, zolpidem, zonisamide, zopiclone, zopiclone, S-zopolrestat, zotepine.

Specific Examples of Antibacterials

When antibacterial activity is a desired property of the disclosed ionic liquids, one or more of the ions in the disclosed ionic liquids can be an antibacterial. That is the one or more kinds of cations, one or more kinds of anions, or both cations and anions can be an antibacterial. Many of suitable antibacterial have already been disclosed herein (e.g., many QACs have antibacterial properties). Further examples of suitable antibacterial agents include, but are not limited to, acedapsone, acetosulfone sodium, alamecin, alexidine, amdinocillin, amdinocillin pivoxil, amicycline, amifloxacin, amifloxacin mesylate, amikacin, amikacin sulfate, aminosalicylic acid, aminosalicylate sodium, amoxicillin, amphomycin, ampicillin, ampicillin sodium, apalcillin sodium, apramycin, aspartocin, astromicin sulfate, avilamycin, avoparcin, azithromycin, azlocillin, azlocillin sodium, bacampicillin hydrochloride, bacitracin, bacitracin methylene disalicylate, bacitracin zinc, bambermycins, benzoylpas calcium, berythromycin, betamicin sulfate, biapenem, biniramycin, biphenamine hydrochloride, bispyrithione magsulfex, butikacin, butirosin sulfate, capreomycin sulfate, carbadox, carbenicillin disodium, carbenicillin indanyl sodium, carbenicillin phenyl sodium, carbenicillin potassium, carumonam sodium, cefaclor, cefadroxil, cefamandole, cefamandole nafate, cefamandole sodium, cefaparole, cefatrizine, cefazaflur sodium, cefazolin, cefazolin sodium, cefbuperazone, cefdinir, cefepime, cefepime hydrochloride, cefetecol, cefixime, cefmenoxime hydrochloride, cefmetazole, cefmetazole sodium, cefonicid monosodium, cefonicid sodium, cefoperazone sodium, ceforanide, cefotaxime sodium, cefotetan, cefotetan disodium, cefotiam hydrochloride, cefoxitin, cefoxitin sodium, cefpimizole, cefpimizole sodium, cefpiramide, cefpiramide sodium, cefpirome sulfate, cefpodoxime proxetil, cefprozil, cefroxadine, cefsulodin sodium, ceftazidime, ceftibuten, ceftizoxime sodium, ceftriaxone sodium, cefuroxime, cefuroxime axetil, cefuroxime pivoxetil, cefuroxime sodium, cephacetrile sodium, cephalexin, cephalexin hydrochloride, cephaloglycin, cephaloridine, cephalothin sodium, cephapirin sodium, cephradine, cetocycline hydrochloride, cetophenicol, chloramphenicol, chloramphenicol palmitate, chloramphenicol pantothenate complex, chloramphenicol sodium succinate, chlorhexidine phosphanilate, chloroxylenol, chlortetracycline bisulfate, chlortetracycline hydrochloride, cinoxacin, ciprofloxacin, ciprofloxacin hydrochloride, cirolemycin, clarithromycin, clinafloxacin hydrochloride, clindamycin, clindamycin hydrochloride, clindamycin palmitate hydrochloride, clindamycin phosphate, clofazimine, cloxacillin benzathine, cloxacillin sodium, cloxyquin, colistimethate sodium, colistin sulfate, coumermycin, coumermycin sodium, cyclacillin, cycloserine, dalfopristin, dapsone, daptomycin, demeclocycline, demeclocycline hydrochloride, demecycline, denofungin, diaveridine, dicloxacillin, dicloxacillin sodium, dihydrostreptomycin sulfate, dipyrithione, dirithromycin, doxycycline, doxycycline calcium, doxycycline fosfatex, doxycycline hyclate, droxacin sodium, enoxacin, epicillin, epitetracycline hydrochloride, erythromycin, erythromycin acistrate, erythromycin estolate, erythromycin ethylsuccinate, erythromycin gluceptate, erythromycin lactobionate, erythromycin propionate, erythromycin stearate, ethambutol hydrochloride, ethionamide, fleroxacin, floxacillin, fludalanine, flumequine, fosfomycin, fosfomycin tromethamine, fumoxicillin, furazolium chloride, furazolium tartrate, fusidate sodium, fusidic acid, gentamicin sulfate, gloximonam, gramicidin, haloprogin, hetacillin, hetacillin potassium, hexedine, ibafloxacin, imipenem, isoconazole, isepamicin, isoniazid, josamycin, kanamycin sulfate, kitasamycin, levofuraltadone, levopropylcillin potassium, lexithromycin, lincomycin, lincomycin hydrochloride, lomefloxacin, lomefloxacin hydrochloride, lomefloxacin mesylate, loracarbef, mafenide, meclocycline, meclocycline sulfosalicylate, megalomicin potassium phosphate, mequidox, meropenem, methacycline, methacycline hydrochloride, methenamine, methenamine hippurate, methenamine mandelate, methicillin sodium, metioprim, metronidazole hydrochloride, metronidazole phosphate, mezlocillin, mezlocillin sodium, minocycline, minocycline hydrochloride, mirincamycin hydrochloride, monensin, monensin sodiumr, nafcillin sodium, nalidixate sodium, nalidixic acid, natainycin, nebramycin, neomycin palmitate, neomycin sulfate, neomycin undecylenate, netilmicin sulfate, neutramycin, nifuiradene, nifuraldezone, nifuratel, nifuratrone, nifurdazil, nifurimide, nifiupirinol, nifurquinazol, nifurthiazole, nitrocycline, nitrofurantoin, nitromide, norfloxacin, novobiocin sodium, ofloxacin, onnetoprim, oxacillin sodium, oximonam, oximonam sodium, oxolinic acid, oxytetracycline, oxytetracycline calcium, oxytetracycline hydrochloride, paldimycin, parachlorophenol, paulomycin, pefloxacin, pefloxacin mesylate, penamecillin, penicillin G benzathine, penicillin G potassium, penicillin g procaine, penicillin g sodium, penicillin V, penicillin V benzathine, penicillin V hydrabamine, penicillin V potassium, pentizidone sodium, phenyl aminosalicylate, piperacillin sodium, pirbenicillin sodium, piridicillin sodium, pirlimycin hydrochloride, pivampicillin hydrochloride, pivampicillin pamoate, pivampicillin probenate, polymyxin B sulfate, porfiromycin, propikacin, pyrazinamide, pyrithione zinc, quindecamine acetate, quinupristin, racephenicol, ramoplanin, ranimycin, relomycin, repromicin, rifabutin, rifametane, rifamexil, rifamide, rifampin, rifapentine, rifaximin, rolitetracycline, rolitetracycline nitrate, rosaramicin, rosaramicin butyrate, rosaramicin propionate, rosaramicin sodium phosphate, rosaramicin stearate, rosoxacin, roxarsone, roxithromycin, sancycline, sanfetrinem sodium, sarmoxicillin, sarpicillin, scopafungin, sisomicin, sisomicin sulfate, sparfloxacin, spectinomycin hydrochloride, spiramycin, stallimycin hydrochloride, steffimycin, streptomycin sulfate, streptonicozid, sulfabenz, sulfabenzamide, sulfacetamide, sulfacetamide sodium, sulfacytine, sulfadiazine, sulfadiazine sodium, sulfadoxine, sulfalene, sulfamerazine, sulfameter, sulfamethazine, sulfamethizole, sulfamethoxazole, sulfamonomethoxine, sulfamoxole, sulfanilate zinc, sulfanitran, sulfasalazine, sulfasomizole, sulfathiazole, sulfazamet, sulfisoxazole, sulfisoxazole acetyl, sulfisboxazole diolamine, sulfomyxin, sulopenem, sultamricillin, suncillin sodium, talampicillin hydrochloride, teicoplanin, temafloxacin hydrochloride, temocillin, tetracycline, tetracycline hydrochloride, tetracycline phosphate complex, tetroxoprim, thiamphenicol, thiphencillin potassium, ticarcillin cresyl sodium, ticarcillin disodium, ticarcillin monosodium, ticlatone, tiodonium chloride, tobramycin, tobramycin sulfate, tosufloxacin, trimethoprim, trimethoprim sulfate, trisulfapyrimidines, troleandomycin, trospectomycin sulfate, tyrothricin, vancomycin, vancomycin hydrochloride, virginiamycin, and zorbamycin. Penicillin G, which is used as an antibacterial agent for infections including pneumonia, meningitis, and skin, bone, joint, stomach, blood, and heart valve infections, is a particular example suitable for use herein. tazobactum, sold under the trade names ZOSYN™ and TAZOCIN™, ceftrioxone, sold under the trade name ROCEPHIN™, and metronidazol, sold under the trade name FLAGYL™, are also used to treat bacterial infections and are further examples of suitable compounds that can be used to prepare the disclosed ionic liquids.

These and other suitable antibacterials can be identified based on the desired properties of the antibacterial and whether the antibacterial active is or can be converted into an ion. As noted, identification of whether an antibacterial active is an ion or can be converted into an ion can be done by a skilled artisan inspecting the chemical structure of the antibacterial.

Specific Examples of Antiviral

When antiviral activity is a desired property of the disclosed ionic liquids, one or more of the ions in the disclosed ionic liquids can be an antiviral. Examples of suitable antiviral actives include, but are not limited to, acemannan, acyclovir, acyclovir sodium, adefovir, alovudine, alvircept sudotox, amantadine hydrochloride, aranotin, arildone, atevirdine mesylate, pyridine, cidofovir, cipamfylline, cytarabine hydrochloride, delavirdine mesylate, desciclovir, didanosine, disoxaril, edoxudine, enviradene, enviroxime, famciclovir, famotine hydrochloride, fiacitabine, fialuridine, fosarilate, foscarnet sodium, fosfonet sodium, ganciclovir, ganciclovir sodium, idoxuridine, kethoxal, lamivudine, lobucavir, memotine hydrochloride, methisazone, nevirapine, penciclovir, pirodavir, ribavirin, rimantadine hydrochloride, saquinavir mesylate, somantadine hydrochloride, sorivudine, statolon, stavudine, tilorone hydrochloride, trifluridine, valacyclovir hydrochloride, vidarabine, vidarabine phosphate, vidarabine sodium phosphate, viroxime, zalcitabine, zidovudine, zinviroxime, and Tamiflu.

These and other suitable antivirals can be identified based on the desired properties of the antiviral and whether the antiviral is or can be converted into an ion. As noted, identification of whether an antiviral is an ion or can be converted into an ion can be done by a skilled artisan inspecting the chemical structure of the antiviral.

Specific Examples of Pesticidal Actives

When pesticidal activity is a desired property of the disclosed ionic liquids, one or more of the ions in the disclosed ionic liquids can be a pesticide. Included within the meaning of "pesticide" are insecticides and fungicides. Examples of suitable pesticides include, but are not limited to, carfentrazone-ethyl, sulfentrazone, clomazone, diclofop-methyl, oxamyl propargite, prosulfuron, pyridate, pyriftalid, S-metolachlor, simazine, terbuthylazine, terbutryn, triasulfuron, trifloxysulfuron, trinexapac-ethyl, ametryn, atrazine, benoxacor, bifenthrin, butafenacil, choline azide, chlortoluron, cinosulfuron, clodinafop, cloquintocet, DEET, desmetryn, dicamba, dimethachlor, dimethametryn, DTPA NaFe, EDDHA NaFe, fenclorim, flumetralin, fluometuron, fluthiacetmethyl, halosulfuron, isoproturon, metobromuron, metolachlor, norflurazon, oxasulfuron, piperophos, pretilachlor, primisulfuron, prometryn, propaquizafop, acibenzolar-s-methyl, chlorothalonil, cyproconazole, cyprodinil, difenoconazole, fenpropidin, fenpropimorph, furalaxyl, metalaxyl, metalaxyl-m, oxadixyl, penconazole, propiconazole, pyrifenox, thiabendazol, abamectin, bromopropylate, cypermethrin, cypermethrin high-cis, cyromazine, diafenthiuron, diazinon, dichlorvos, disulfoton, emamectinbenzoate, fenoxycarb, formothion, furathiocarb, lufenuron, methidathion, permethrine, codlemone, phosphamidon, profenofos, pymetrozine, quinalphos, terrazole, thiamethoxam, thiocyclam, thiometon, triallate, trifloxystrobin, vinclozolin, zetacypermethrin, and the like. Prohexadione is a FDA approved reduced risk fungicide and is also useful for the disclosed ionic liquids. Further examples of suitable pesticides can be found in The Pesticide Manual, 11$^{th}$ Edition, British Crop Protection Council, 1997, which is incorporated by reference herein at least for its teaching of pesticides.

These and other suitable pesticides can be identified based on the desired properties of the pesticide and whether the pesticide is or can be converted into an ion. As noted, identification of whether a pesticide is an ion or can be converted into an ion can be done by a skilled artisan inspecting the chemical structure of the pesticide.

Specific Examples of Herbicidal Actives

When herbicidal activity is a desired property of the disclosed ionic liquids, one or more of the ions in the disclosed ionic liquids can be a herbicide. Examples of suitable herbicides include, but are not limited to, carfentrazone, imazapyr, benefin, acifluorfen, and 2-[2-chloro-3-(2,2,2-trifluoroethoxymethyl)-4-methylsulfonylbenzoyl]cyclohexane-1.

Other suitable herbicides include inhibitors of the biosynthesis of branched amino acids such as ethoxysulfuron, flumetsulam, halosulfuron, imazamox, imazapyr, imazaquin, imazethapyr, metosulam, nicosulfuron, primisulfuron, prosulfuron, rimsulfuron, thifensulfuron-methyl, triflusulfuron, N-[(4,6-dimethoxypyrimidin-2-yl)aminocarbonyl]-2-dimethylaminocar-bonyl-5-formylaminobenzenesulfonamide (Foramsulfuron), and the like. Still further, suitable herbicides include inhibitors of the photosynthesis electron transport such as ametryne, atrazine, bromoxynil, cyanazine, diuron, hexazinone, metribuzin, pyridate, terbuthylazine, and the like. In yet further examples, suitable herbicides for the disclosed ionic liquids include synthetic auxins such as copyralid, dicamba, diflufenzopyr, fluoroxypyr, and the like. Inhibitors of fatty acid biosynthesis, such as butylate, EPTC, fenoxaprop-P-ethyl, and the like, can also be used in the disclosed ionic liquid compositions. In other examples, suitable herbicides can include inhibitors of cell division such as acetochlor, alachlor, dimethenamid, flufenacet, mefenacet, metolachlor, S-metolachlor, thenylchlor, and the like. In still other examples, the herbicide can be an inhibitor of protoporphyrinogen oxidase, such as fluthiacet-methyl, carfentrazone-ethyl, and the like. Inhibitors of hydroxyphenylpyruvate dioxygenase, such as isoxaflutole, mesotrione, sulcotrione, 4-(4-trifluoromethyl-2-methylsulfonylbenzoyl)-5-hydroxy-1-methyl-3-methylpyrazole, and the like, can also be used. Further examples of suitable herbicides include, but are not limited to, glyphosate, pendimethalin, trifluralin, asulam, triaziflam, diflufenican, glufosinate-ammonium, and the like. Clofencet, fluoroxypyr, mesosulfuron, diflufenzopyr are further examples of suitable herbicides and they are FDA approved.

Specific Examples of Other Ions

In addition to the pharmaceutical, antibacterial, antiviral, pesticidal, and herbicidal actives disclosed herein, other compounds that are ions or can be converted to ions can be used in the disclosed ionic liquid compositions. Specific examples of these include, but are not limited to, the food additives Allura Red AC (FD&C Red No. 40), Tartrazine (FD&C Yellow No. 5), Indigotine (FD&C Blue No. 2), Erythrosine (FD&C Red No. 3), and Sunset Yellow (FD&C Yellow No. 6), which are FDA-approved color additives for food use. Further, nutraceuticals such as fatty acids, cholesterols, vitamins, minerals, and trace elements can be suitable ions for the disclosed ionic liquid compositions. SEA-NIN-211 is an antifoulant that can be used as an ion id the disclosed compositions.

Liquid Ion Pairs

Dual functioning organic salts that do not behave as free ions either neat or in a solvent (including water) will retain the functionality of each ion in close enough proximity to lead to synergistic effects. The degree of association (or conversely dissociation) will affect the physical, chemical, and importantly, the biological properties.

Ion pairing/clustering which imparts some extra (other than merely additive) effect in operation, e.g., enhances the therapeutic effect or increases the activity of the individual ions OR decreases the activity! While this latter may often seem to be unimportant there are cases where it would be desirable, e.g., in slow release formulations (activity here may refer to solubility or rate of diffusion from the reservoir).

The ability to "design" a liquid salt that is the thermodynamically most stable state AT a specific temperature, i.e., NOT a quenched amorphous phase that may crystallize, is important as this offers opportunities in formulation of, e.g., emulsions and will almost always provide a more soluble or dispersible form than a crystalline form.

The concept of specific stoichiometric salts—note that this sort of clustering may also be of import.

The activity of drugs in the body is not the only consideration, but also the formulation advantages that may accrue from having an ion-pairing or ion-clustering salt.

In applications other than drugs (though also applies here, particularly to pro-drugs that hydrolyze or easily degraded drugs—analogous to protection against UV degradation by formulation as inclusion complexes), some of the advantages will be in the ability to create a liquid formulation that DOES NOT require water—advantages are a) stabilization; b) ease of dispersion/dissolution upon introduction into an aqueous system and c) possibilities to dissolve other substances in these salts—for example "edible IL to dissolve drugs"—the liquid salts could be used to dissolve other solid actives.

Figure 7:
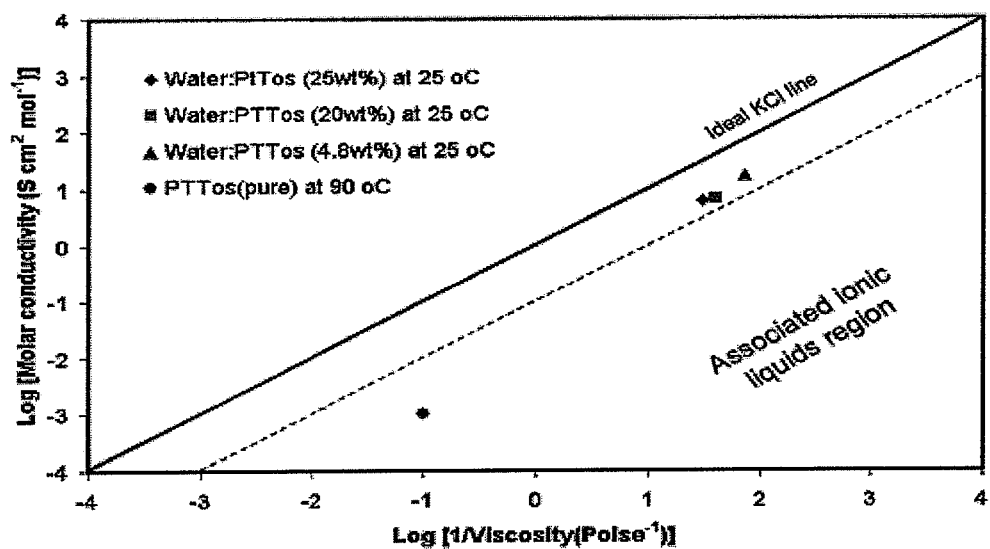
FIG. 7 depicts the Walden plot for various propantheline p-toluenesulfonates.

Many examples of liquid organic salts are far from fully ionized. Instead, they form ion pairs and aggregates of ions in the liquid state and are better described as Liquid Ion Pairs than "Ionic Liquids". The distinction between these states can be made on the basis of the behavior of the transport property data when plotted in a Walden plot. The Walden plot is a graph of log equivalent conductivity (corrected for molar volume) vs. log fluidity and thus may be used to estimate the degree of association cations and anions (as correlated motion of cation and anion clusters). Ionic Liquids typically lie within one order of magnitude of the "Ideal Ionic Liquid" line (that line on which salts which exhibit no correlated motion of cation and anion lie) meaning that they are between 10 and 100% ionic. Liquid Ion Pairs lie beyond this region, i.e., more than one order of magnitude away from the Ideal line. Such liquid salts are less than 10% ionized. Examples of such liquid salts of therapeutic ions include propanthaline tosylate which is about 1% ionized, as estimated from the Walden plot (FIG. 7).

This degree of association of cations and anions (as ion pairs or larger clusters) will affect various physico-chemical properties of the salts; for example, greater "ion-pairing" (which should be understood to mean clustering of any number of cations and anions) will yield a more fluid and more volatile salt as ion pairs (or clusters) move as single entities and may be vaporized as uncharged clusters which thus more readily escape the liquid due to decreased coloumbic interactions with the bulk.

If such ion-pairing, or clustering, persists in solution cation or anion interactions with the environment, e.g., the body, will not simply be additive and the salt will not behave in the same way as a 1:1 molar mixture of salts containing the same cation and anion. In addition, such ion-pairing, or ion-clustering, salts may form a separate phase in certain solvent systems and may thus be utilized as emulsions or other dispersed phases. The non-additive effect of cation and anion in ion-paired, or clustered, salts may be either synergistic (enhanced efficacy) or antagonistic (decreased efficacy) and this allows modulation of properties by judicious choice of cation/anion pairs in salt formation.

Opportunities exist for the preparation of:
Enhanced therapeutic salt substances which combine:
  2 API ions chosen for specific activity
  an API ion and second active which alters physico-chemical properties such as lipophilicity, thus changing, for example, membrane or transdermal transport
  an API ion and second ion which serves to mask unpleasant taste and/or smell
  animal therapeutic substances
Enhanced agrochemical substances which may have similar effects to those above and yields a material easily dispersible in a second carrier, for example, as an emulsion, which nonetheless retains its lipophilicity and thus is not easily removed from surfaces, e.g. leaves Solvates/Hydrates Liquid salts can exist in a defined intermediate stage where they are solvated, but not 'in solution. This stage is characterized by all solvent present in the liquid salt being bound rather than free as demonstrated by DSC and other data.

A convenient method of determining the point where an ionic liquid containing dissolved water becomes an aqueous solution, in which water is the solvent rather than the solute, is low temperature thermal analysis. By this means we can determine the point, with increasing water content, at which the crystallization and melting of bulk ice first appears in the mixtures. The low temperature phase behaviour of aqueous salt solutions has been extensively studied in the context of cryobiology (Angell, C. A., D. R. MacFarlane et al., *Journal of Physical Chemistry,* 1981. 85 p. 1461-1464; MacFarlane, D. R., R. K. Kadiyala, and C. A. Angell, *Journal of Chemical Physics,* 1983. 79 p. 3921-3927*; Journal of Physical Chemistry,* 1983. 87 p. 1094-1095; MacFarlane, D., *Cryobiology,* 1985. 22 p. 601-602; MacFarlane, D. R., *Cryobiology,* 1986. 23 p. 559-560; MacFarlane, D. R., *Cryobiology,* 1986. 23 p. 230-244; MacFarlane, D. R., *Cryobiology,* 1987. 24 p. 181-195). Typical binary phase diagrams have been established and show the characteristics illustrated in FIG. 1.

At high water contents (Region A of the diagram) the sample will crystallize ice during cooling in the DSC and exhibit a subsequent melting peak during warming. This peak is more precisely described as the ice liquidus peak, corresponding to the process of ice dissolution into the solution. The liquidus line of ice in these solutions is denoted TL.

At lower water contents, corresponding to the middle of this diagram, Region B, the ice crystalisation during cooling, or at low temperatures during subsequent warming, becomes less extensive and more sluggish, since less bulk water is available to freeze into ice. Annealing experiments can be used to allow the ice to form and one observes the liquidus line falling rapidly in Region B. In the absence of a fully formed eutectic, which is common in many aqueous—salt binaries, part of the solution remains unfrozen during the cooling or annealing treatment. This part contains all of the salt and some water. The composition of the unfrozen part can be estimated from the phase diagram and the lever rule. Evidence for this can also be seen via the appearance of a glass transition at temperature denoted Tg' in the partially frozen solution. Since the composition of the unfrozen fraction is independent of starting concentration, Tg' is almost composition independent through regions A and B as seen in the diagram.

At some point in region B, depending on the cooling rate applied, it will be possible to quench the sample into the glassy state without the crystallisation of any ice. The warming DSC trace then will show the true Tg for that composition (marked as Tg in FIG. 1). Typically Tg is a strong function of composition through regions B and C. Despite the ability to quench into a fully glassy state, the sample can still crystallize ice during warming in region B, indicating that solvent water still exists in the solution.

However, in region B TL is rapidly approaching Tg and, at the composition where it falls below Tg, formation of ice becomes an insignificant event on any measurable timescale. At that point it can be said that the solution shows no evidence, on any measurable timescale, of "solvent" water and that the remaining water is involved in direct solvation interactions with the ions. This marks the beginning of region C, which we refer to as the 'hydrate ionic liquid' region. In this region the ionic liquid should be considered to be the solvent.

Note that it is possible that the melting point of the pure salt may be higher than room temperature, or even higher than 100° C. If the addition of the solute amount of water to the salt to form a mixture of composition in region C is sufficient to lower the melting point of the salt to below room temperature (or other temperature of interest) then the mixture can still be considered to be a hydrate ionic liquid. The important properties of such mixtures is that they are still (in common with single component ionic liquids) liquids comprised solely of ions, in this case hydrated ions.

The use of the term "hydrate" here is justified by its use in solid state chemistry to describe salts which contain water molecules in their crystal structures. In many cases eg $Ca(NO_3)_2.4H_2O$, there is a well understood metal solvation involved such that one could consider this salt to be $Ca(H_2O)_4(NO_3)_2$. Indeed it melts congruently at 65° C. to a fluid, conductive liquid state. Such hydrate salt ionic liquids have been studied in detail (MacFarlane, D. R. and D. K. Y. Wong, *Journal of Physical Chemistry,* 1985. 89 p. 5849-5855; MacFarlane, D. R. and C. A. Angell, *Journal of Physical Chemistry,* 1984. 88 p. 4779-4781). The solid hydrate salts often contain a variable number of water molecules suggesting a solid solution situation exists in some cases. Nonetheless these salts are still referred to as hydrates. We therefore propose that the parallel situation in which a liquid salt-water mixture containing a variable amount of solute water be referred to as a hydrate ionic liquid as long as it exists in Region C of the binary phase diagram.

Intermediate Partially Ionized Liquid Phases

Without wishing to be bound by theory, for the purposes of the present disclosure, when a disclosed acid (HA) is combined with a disclosed base (B), an equilibrium can exist as follows:

$$HA+B \leftrightarrow [BH]A$$

As such, the combination of a functional acid, HA, and a functional base, B, can produce liquid compositions having a dual function or capacity, i.e., the properties of each individual component. Disclosed herein are examples of an acid that is a solid at room temperature which when combined with a base that is a solid at room temperature, leads to a liquid that is a partially ionized composition. Therefore, the formulator, by controlling the equilibrium, can also adjust or modify the physical, chemical, and biological properties of the final compound.

Multiple Functional Co-Ionic Liquids

Disclosed herein are pharmaceutically active, multiply functional co-ionic liquids comprising oligomeric cations or anions and wherein the co-ionic liquids provide a method for the modification of physico-chemical properties of pharmaceutically active salts. Used here, the term "co-ionic liquids" includes ionic liquids with excess of any free base in equilibrium with the cation or excess of any free acid anion in equilibrium with the anion; thus it is possible to prepare pharmaceutically active ionic liquids with dimeric or oligomeric ions of the type:

These compositions differ from conventional mixture of ionic liquids with neutral compounds by the fact that a proton is shared between anion and any acid or between cation and any base and all components are therefore present as ions.

These compositions also differ from conventional mixtures of ionic liquids by the fact that the total amount of cationic compounds is not balanced by the total amount of anionic compounds anymore, although an overall cation:anion ratio of 1:1 is obtained.

For example, whereas a conventional ionic liquid would have been 1 part cation, 0.5 part first anion, and 0.5 part second anion, the co-ionic liquids disclosed in this invention can be 1 part cation, 1 part first anionic unit and 1 part of a second anionic unit that are in proton exchanged to form one mixed anion with a total charge of −1. When the disclosed ionic liquid compositions have two or more ions with a bio-active property (e.g., pharmaceutical active ingredients, pesticidal actives, herbicidal actives, and the like), these compositions can be particularly desired because each of the active ingredients in the composition would have the same solubility and would dissolve together when formulated or administered.

The present invention provides in a first aspect a method to transform solid salts into liquid mixtures by simply changing the stoichiometry of the active pharmaceutical salts without addition of a new compound that might completely alter the biological properties. This can be particularly useful when overcoming formulation, solubility, bioavailability, size, and polymorphism issues.

In the current invention, it is not even necessary to add an additional equivalent of acid or base to form dimeric anions or cations. For example, an co-ionic liquid composition disclosed herein can eliminate the melting point of a solid salt by addition of sub-stoichiometric amounts of acid, as it is demonstrated in the example with tetrabutylphosphonium salicylate: an excess of 0.1 equivalent of salicylic acid does already reduce the melting point of the conventional salt from 57 to 39° C., and a 0.3 molar excess completely eliminates the melting point to yield a free flowing liquid (FIG. 2), despite the fact that both ionic liquid and free acid are solid at room temperature. A permanent proton exchange between anion and corresponding acid is present in these coionic liquids making both species undistinguishable on a NMR time scale. The degree of additional acid or base does therefore affect various physico-chemical properties of the salts; for example, the formation of a "super-anion" or "super-cation" (which is a result of a proton exchange between the ion and the corresponding acid or base) will lead to a permanent delocalization of charge and depress the melting point or completely eliminate crystallization. The presence of distinct oligomeric species, e.g. dimeric or trimeric anions can be demonstrated via conductivity measurements: The presence of local maxima for conductivity of $P(Bu)_4[(Sal)_xH]$ for the species $P(Bu)_4Sal_2H$ and $P(Bu)_4Sal_3H$ strongly indicates the presence of hydrogen-bonded oligomeric anions (FIG. 3).

Current strategies for reduction of melting point of pharmaceutical active salts mainly rely on the formation of conventional eutectics, however, this includes the addition of a third and different compound that could completely alter the chemical properties of the salt. Our invention differs by the absence of an eutectic point: Addition of acid or base eliminates the melting point or drives it below the glass transition temperature and will eventually lead to a point of saturation at a certain stoichiometry. Higher concentrations result in the precipitation of excess acid and in a suspension of solid acid in a co-ionic liquid with a dimeric anion. The identity of the cation or of the anion is not critical to the scope of this invention: Independently of the cation, a depression of elimination of the melting point or—in case of salts that appear as glasses—a decrease of the glass transition temperature was observed was observed with different pharmaceutically active acids with 2- or 3-fold excess. Some specific examples of co-ionic liquids include, but are not limited to the pharmaceutically active anions salicylate and ibuprofenate as well as to the biological active cations cetylpyridinium, lidocainium, ephedrinium, choline or caffeine.

Salicylate is chiefly used in anti-acne formulation, but also in various skin-care products. Ibuprofen is used as an anti-inflammatory and available as over-the-counter analgesic. Lidocaine is a common local anesthetic. Cetylpyridinium is used as an antiseptic agent alone or in combination with other drugs for oral and throat care. It is essentially nontoxic and can be applied to the skin or mucous membranes. Besides their pharmaceutical activity, caffeine and ephedrine are also common in dietary supplement.

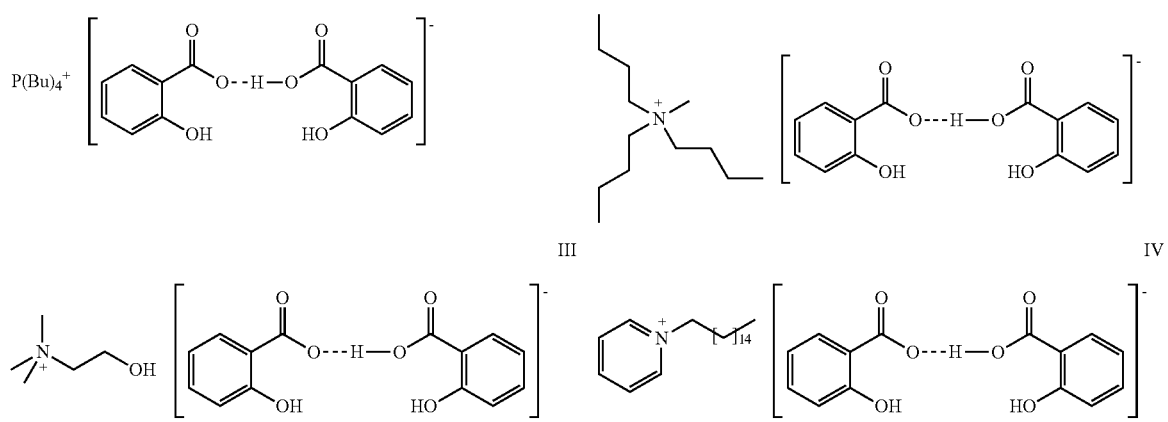

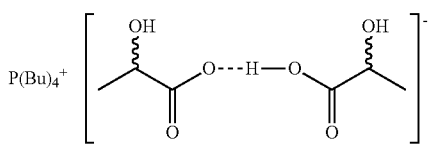

V

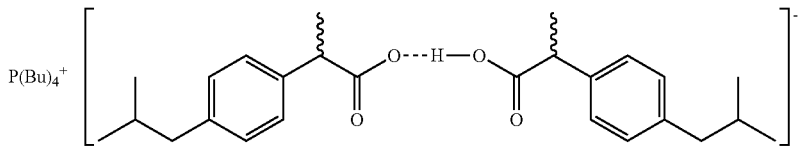

VI

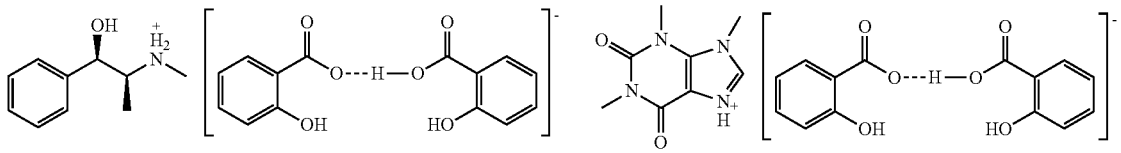

VII VIII

By example, an elimination of melting point or a reduction of melting point or glass transition with excess acid was obtained for tetrabutylphosphonium salicylate I, tributylmethylammonium salicylate II choline salicylate III, cetylpyridinium salicylate IV, tetrabutylphoshonium lactate V, tetrabutylphoshonium ibuprofenate VI, lidocaine salicylate VII and caffeine salicylate VIII for tetrabutylphosphonium lactate.

Figure 4:
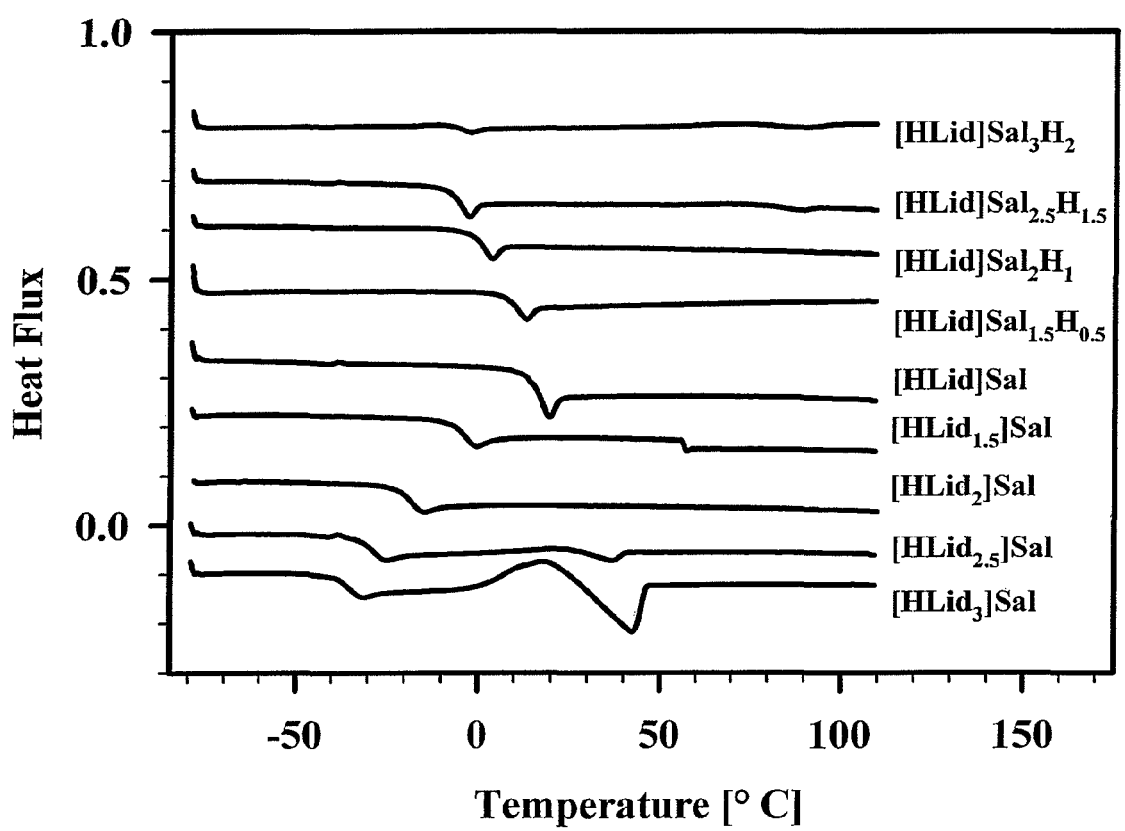
FIG. 4 depicts the depression of glass transition and saturation of double functional co-ionic liquids based on lidocainium salicylate.
Figure 5:
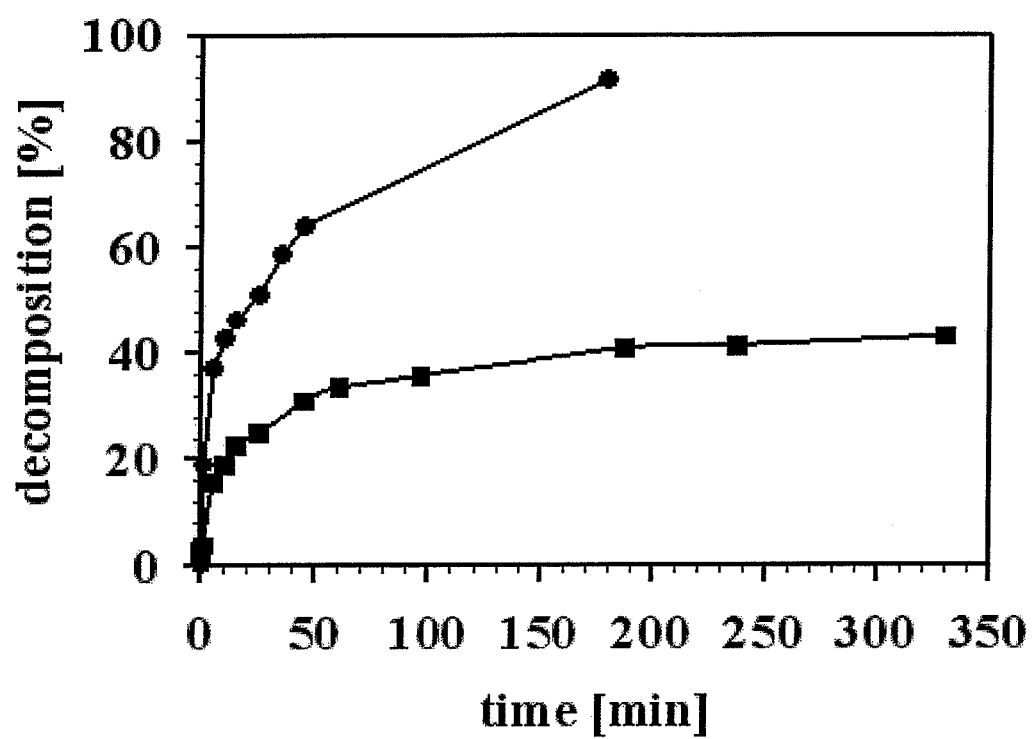
FIG. 5 depicts the decomposition of the prodrug ionic liquids 1-[2-(4-acetamidophenoxy)-2-oxoethyl]-3-methyl-1H-imidazol-3-ium chloride (●) and [2-(4-acetamidophenoxy)-2-oxoethyl]tributylphosphonium chloride (■) versus time in phosphate buffer pH 7.4 at 37° C.

In further examples, the disclosed co-ionic liquid compositions are not limited to higher anionic species, but can be observed almost in the same manner when excess base is added: An excess of lidocaine to the parent salt lidocaine salicylate results not only in a decreased glass transition temperature, but also in a notable reduction of viscosity until at a certain excess of lidocaine a point of saturation is obtained and a solid sample results (FIG. 4). Specific examples of such protic compositions include, but are not limited to, compositions where the cation is a local anesthetic like lidocaine IX or a decongestant like ephedrine X or one of its diastereomers and are shown below.

IX

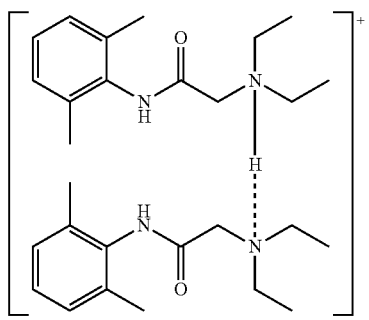 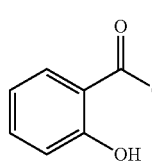

-continued

X

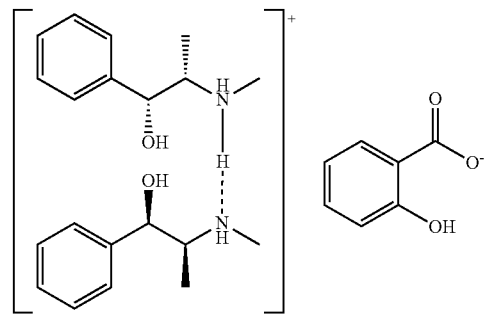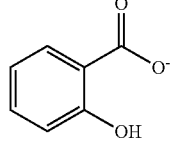

In the present invention, the concept double functional co-ionic liquids is not limited to mixtures of a neutral salt with the corresponding acid or base, but can be also applied to the addition of different solid acids or bases other than the parent compounds to obtain liquids type $B[A^1HA^2]$ or $[B^1HB^2]A$. It is therefore possible to expand the scope of ionic liquids to more than two compounds that are none the less all involved in proton-exchange process and therefore differ from a simple solution of a third compound in a conventional ionic liquid.

Some specific examples of co-ionic liquids include, but are not limited to the pharmaceutically active anions salicylate and ibuprofenate, or the vitamin niacine. Examples also include chiral species, as it was demonstrated with camphorsulfonic acid.

XI

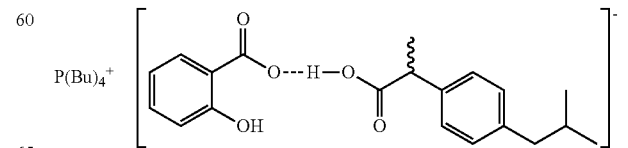

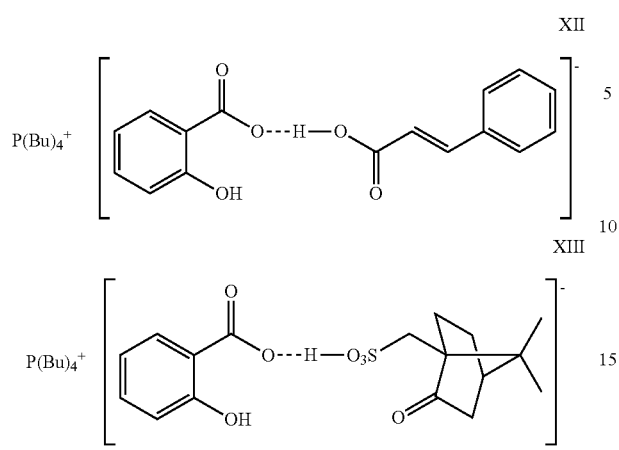

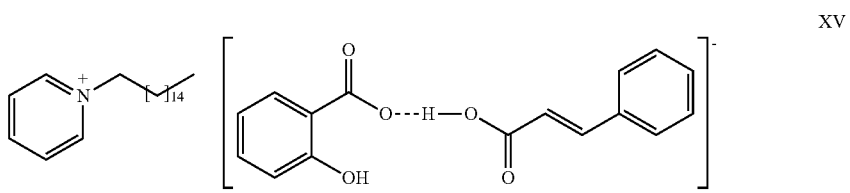

It is notable in all cases a liquid product is obtained with a glass transition temperature at around −50° C. only, although both starting materials tetrabutyl phosphonium salicylate and the shown acids are solid at room temperature. This elimination of melting point is most likely related to a formation of a mixed "super-anion" that is derived from proton delocatization as it was observed in the tetrabutylphosphonium salicylate-salicylic acid dimer. A reasonable difference in pKa of about 2 units is therefore necessary to allow a permanent hydrogen exchange between the acids $A^1$ and $A^2$ and the inhibition of crystallization.

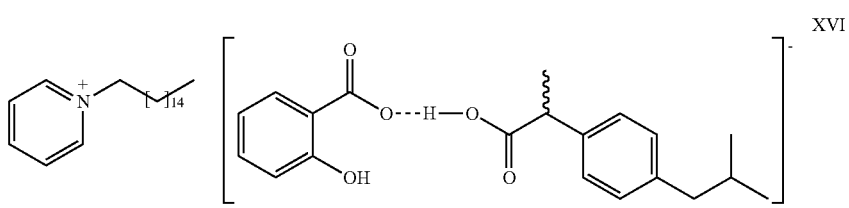

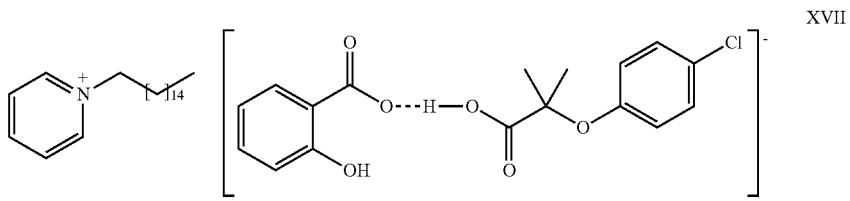

Other therapeutic useful combinations of 3 or more active compounds include the antibacterial cation cetylpyridinium in combination with various pharmaceutically active anions: Salicylate is chiefly used in anti-acne formulation, but also in various skin-care products. Ibuprofen is used as an anti-inflammatory and available as over-the-counter analgesic, and clofibric acid is used as lipid-lowering agent. Some specific examples of triple functional ionic liquids that show a melting depression compared to the common dual functional co-ionic liquids include, but are not limited to the combinations cetylpyridinium salicylate-cinammate XV, cetylpyridinium salicylate-ibuprofenate XVI and cetylpyridinium salicylate-clofibrate XVII.

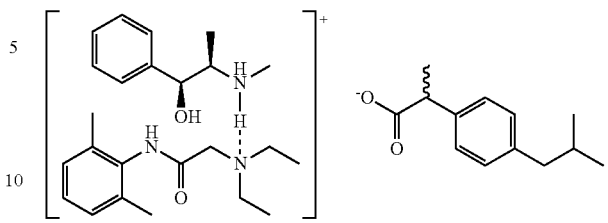

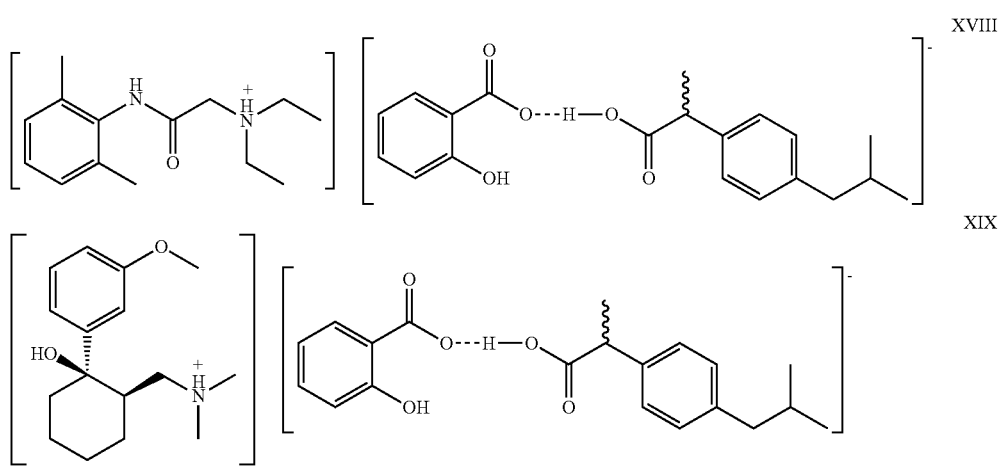

Other examples include co-ionic liquids comprising three analgesics compounds, as demonstrated in the compounds lidocaine salicylate-ibuprofenate XVIII and tramadolium salicylate-ibuprofenate XIX.

In another embodiment of the disclosed co-ionic liquids relates to ionic liquids comprising two or more biologically functional compound sharing one proton with the total charge of +1 and one biological functional anion. Non-limiting examples of this embodiment include combinations of the decongestant ephedrine with two analgesic or anaesthetic compounds, as present in ephedrinium-lidocainium salicylate XX or ephedrinium-lidocainium ibuprofenate XXI. Similarly to dimeric anions, triple functional painkillers can be prepared from 3 analgesic compounds like tramadolium-lidocainium ibuprofenate XXII or tramadolium-lidocainium salicylate XXIII.

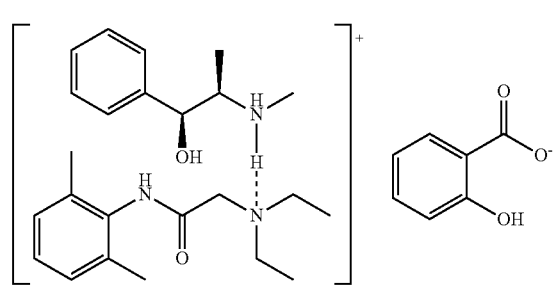

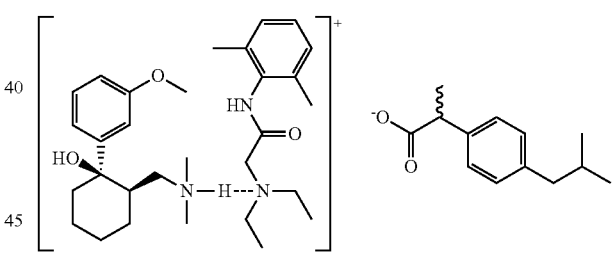

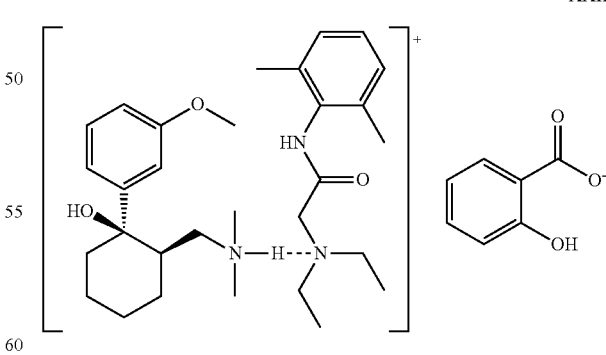

Despite the fact that lidocaine, tramadole hydrate, ibuprofene and even the conventional salt tramadolium ibuprofenate are solid at room temperature the co-ionic liquid of the type $[B^1HB^2]A$ was obtained as clear liquid with a glass transition temperature at −37° C. Synergistic (enhanced efficiency) as previously described for API ionic liquids, e.g. in lidocainium docusate are very likely in these multiple-compound ionic liquids and allow modulation of properties by judicious choice of cation/anions with the desired activities.

Other therapeutically useful combinations include ionic liquids comprised of the decongestant ephedrine and the common antiemetic and antihistaminic promethazine, a combination of promethazine and ephedrine that is established against e.g. seasickness. Triple functional ionic liquids can be obtained in combination with an emollient anion like docusate XXIV or with salicylicylate XXV. It notable that these triple-functional ionic liquids are not limited to stoichiometric mixtures of the three active compounds in the ratio 1:1:1, but allow individual dosing of a selected compounds, as would be present in the co-ionic liquid promethazine-ephedrinium docusate in the ratio 0.5:1:1.

salicylate salt of the type $B[A'HA^2]$. Similarly, if the melting points of at least one of the starting materials or the product are below the decomposition temperature of the API-IL, the pharmaceutically active co-ionic liquids can be prepared in molten state from the acid-base precursors, as it was demonstrated with the system ephedrinium-salicylate 3:1.

Ionic Liquid Prodrugs

This invention relates to the use of ionic liquids for immobilization, delivery, and controlled release of pharmaceutically active liquid or low melting salt compositions. The present invention is based upon the discovery that active compounds, especially pharmaceuticals, can be covalently

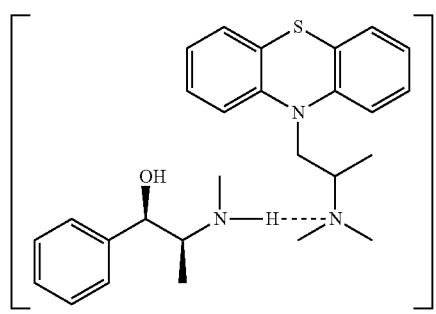
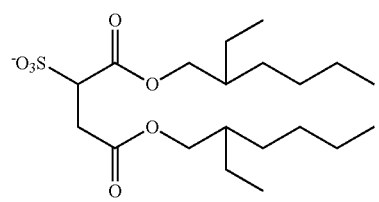

XXIV

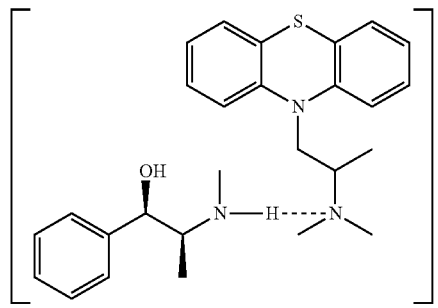
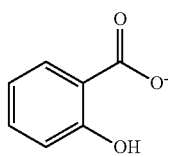

XXV

In a further aspect, this invention relates to solvent-free methods of preparation for co-ionic liquids. The synthesis of double- or multiple functional co-ionic liquids can be easily achieved by stirring additional acid or base with the conventional API IL in an appropriate solvent that dissolves both starting materials, e.g. reaction of cetylpyridinium salicylate and salicylic acid in acetone. Alternatively, if the cation is available as hydroxide salt, direct reaction with the appropriate excess of one or more acids in a co-solvent will directly give rise to co-ionic liquids of the type $B[A^1HA^2]$, as demonstrated with tetrabutylphosphonium salicylate-salicylic acid.

However, methods of preparation also include solvent-free techniques, e.g. grinding or reaction in molten state. Solid tetrabutylphoshonium salicylate and salicylic acid can be easily liquefied by simple grinding in a mortar or by melting the solid tetrabutylphoshonium salicylate and salicylic acid to obtain the liquid tetrabutylphosphonium salicylate-salicylic acid. This solvent-free preparation technique can be even expanded to the preparation of triple-functional co-ionic liquids directly from the acid/base precursors: Grinding of solid lidocaine, ibuprofenic acid and salicylic acid for 15 minutes at room temperature gave the liquid lidocainium-ibuprofenatelinked with ionic structural moiety and turned into an ionic liquid by appropriate choice of the counter ion.

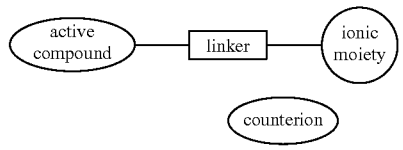

Current methods for the modification of the physical properties of solid drugs rely mainly on its transformation into a salt; however, this is limited to acidic or basic pharmaceutically active compounds. The term "active compound" is used to include any pharmaceutically or biologically active compound, but also nutritional, fragrance or flavour compound, as long as a functional group, typically a hydroxy or amine group, is present to covalently attach this compound on the ionic structure. Thus the neutral compound can be transferred into salts, wherein the active compound is immobilized as part of the ionic liquid in either positive or negative charge.

The term "linking unit" comprises a spacer to attach the neutral active compound to the charged moiety, thus it must possess two reactive positions. In the present invention, linking is achieved by esterification of the neutral active compound with a halogenated acid chloride, e.g. chloroacetyl chloride that can be further alkylated with any cation precursor to transfer the neutral compound into a charged species. The labile ester bond allows cleaving the prodrug and liberating the active compound under defined conditions that include, but are not limited to hydrolysis, pH-dependent cleavage, enzymatic hydrolysis, thermical cleavage or photo cleavage.

However, the linking unit is not limited to ester functionalities; basically, any functional group that can be cleaved under defined conditions can be used as linking unit. Examples include, but are not limited to esters, amides, acetals, diorthoesters, vinylethers, dithiols or azo conjugates.

The term "ionic moiety" can include both cationic or anionic groups covalently attached to the active compound. In case of cations, conventional ionic liquids structural motives include, but are not limited to, quaternary ammonium or phosphonium compounds like imidazolium, pyridinium, pyrrolidinium. Special emphasis has to be put pharmaceutically acceptable cations that will leave approved materials after cleavage, e.g. alkylation with trimethylamine will leave betaine after hydrolysis and release of the active compound. The role of this cationic group is, however not limited to conventional ionic liquid cations, it is also possible to attach the neutral active compound to a second, charged active compound.

Alternatively, in case of immobilization of the neutral compound on the anion, any functional group bearing a negative charge can be chosen. Examples include, but are not limited to carboxylates, sulphates, sulphonates or phosphonates.

The term "counter ion" can include both cations and anions, including pharmaceutical or biological active compounds. The role of the counterion is to control the physiological properties of the ionic liquid composition, such as liquid range, hydrophobicity and lipophilicity, melting point, etc. In the current invention, the ionic liquid acts not only as support for the active compounds, being able to store pharmaceuticals in inactive form but also allow a simple tuning of physical properties of compounds that cannot be directly transferred into salts.

This invention provides in a first aspect a synthetic methodology to transfer neutral compounds into liquid salts to overcome polymorphism, overcome solubility and delivery problems, to control release rates, add functionality, enhance efficacy (synergy), and improve ease of use and manufacture. It has been discovered that the physical properties of the active compound are depending both on the type of ionic liquid ion used for immobilization but also on the counter ion. An appropriate choice of the counter ion can therefore be used to dramatically change solubility of the parent compound or turn hydrophilic salts into hydrophobic salts.

This ionic liquid prodrug approach provides an opportunity to model release kinetics of the active compound on the structure. The choice of linking unit, the covalently attached ionic moiety and the counter ion can all be used to design a prodrug that is labile under defined conditions only. For example, in the present invention it has been demonstrated that a change of ionic liquid unit covalently attached to the active compound can dramatically influence drug release. Specifically, the ionic liquid prodrugs can be considered as versatile liquid delivery systems with a wide range of tuneable properties for neutral compounds.

The invention also provides the possibility to form dual functioning salts by introduction of a second, pharmaceutically or biologically active counter ion or a second, charged active compound. Prodrug decomposition will than provide a neutral and a charged active compound in exactly the same dosage.

This invention also includes triple-functional salts, wherein a neutral active compound is covalently attached to a second, charged active compounds, replace to the typical structural elements that are present in ionic liquids, e.g. imidazolium cations. The constitution of which, can then be paired with a third charged active compounds, which will result in the delivery of 3 active compounds in the same dosage.

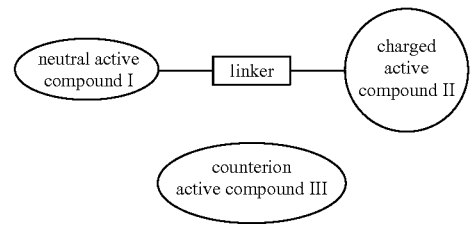

Specific examples in the current invention include ionic liquids prodrugs based on acetaminophen, a widely used analgesic and antipyretic drug used for the relief of fever, headaches, and other minor aches and pains. The phenol proton is not acidic enough to form a stable anion and pair it with appropriate cations; however, we demonstrated that our ionic liquid prodrug strategy can be used to transfer acetaminophen in a stable liquid salt.

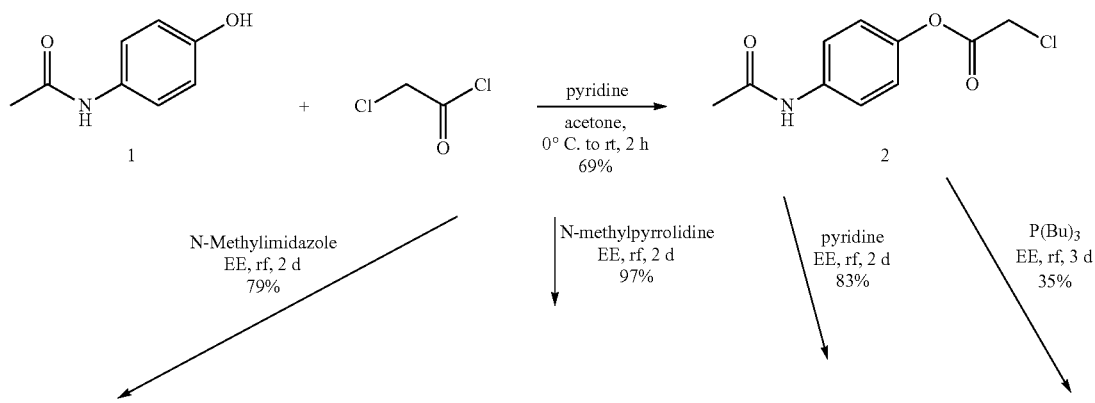

-continued

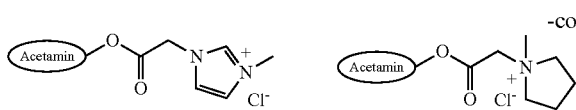

3 Paracet-MeIm-Cl     4 Paracet-Mepyr-Cl     5 Paracet-Py-Cl     6 Paracet-P(Bu)₃-Cl AgDoc MeOH rt, 15 min >99%

AgLac MeOH rt, 15 min >99% anion exchange to hydrophobic docusates 7, 8, 9, 10     anion exchange to hydrophilic lactates

Ionic Liquid Supported Fragrances

This invention relates to the use of ionic liquids for storage and controlled release of volatile compounds, especially fragrances and flavors as liquid salt compositions. The present invention is based upon the discovery that volatile compounds can be covalently linked with ionic structural moiety and turned into an ionic liquid by appropriate choice of the counter ion.

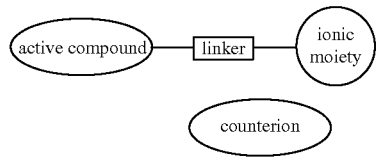

Current methods to issue the loss of volatile frangance or flavour compounds address specific delivery systems like microcapsules and carriers for long-lasting scents.

In the current invention, the ionic liquid acts not only as support for the active compounds, being able to store fragrances and flavors or, in general volatile compounds in non-volatile form but also allows a simple tuning of release conditions.

This invention provides in a first aspect a synthetic methodology to transfer neutral volatile compounds into liquid salts to modify physical properties, avoid evaporation, overcome solubility and delivery problems, to control release rates, add functionality, and improve ease of use, storage and manufacture. It has been discovered that the physical properties of the active compound are depending both on the type of ionic liquid ion used for immobilization, the linking unit but also on the counter ion. The term "active compound" is used to include any active compound, but especially nutritional, fragrance or flavor compound, as long as a functional group, typically a hydroxy or amine group, is present to covalently attach this compound on the ionic structure. Thus the neutral compound can be transferred into a low-volatile salt, wherein the active compound is immobilized as part of the ionic liquid in either positive or negative charge. Examples include, but are not limited to fragrance alcohols like geraniol, menthol, prenol, citronellol or farnesol. The term "linker" comprises a spacing unit to attach the neutral active compound to the charged moiety, thus it must possess two reactive positions. For specific examples in the present invention, linking is achieved by esterification of a fragrance alcohol with a halogenated acid chloride, e.g. chloroacetyl chloride that can be further alkylated with any cation precursor to transfer the neutral compound into a charged species. The labile ester bond allows cleaving the prodrug and liberating the neutral active compound under defined conditions that include, but are not limited to hydrolysis, pH-dependent cleavage, enzymatic hydrolysis, thermical cleavage, photo cleavage or electrodecomposition.

However, the linking unit is not limited to ester functionalities; basically, any functional group that can be cleaved under defined conditions can be used as linking unit. Examples include, but are not limited to esters, amides, acetals, diorthoesters, vinylethers, dithiols or azo conjugates.

The selection of a particular linker, ionic group and counterion depends on the nature of the product in which the delivery system is to be used as well as on the kind of release mechanism required. For example, in the present invention it has been demonstrated that a change of linking unit can lead to different release systems. Specifically, the ionic liquid compositions can be considered as smart retention and delivery devices for triggered release of fragrance, flavour or any other volatile compound.

By example, the typical fragrance alcohol geraniol can be reacted with chloroacetyl chloride as linking unit and further alkylated with N-methylimidazol to the quaternary imidazolium salt 3, which provides, as any ionic liquid neglible volatility. Further ion exchange to docusate 4 can dramatically change physical properties, e.g. solubility and turn a hydrophilic chloride salt 3 into a hydrophobic liquid.

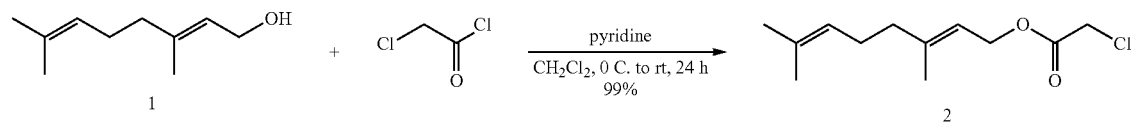

N-methylimidazole neat, rt, on 67%

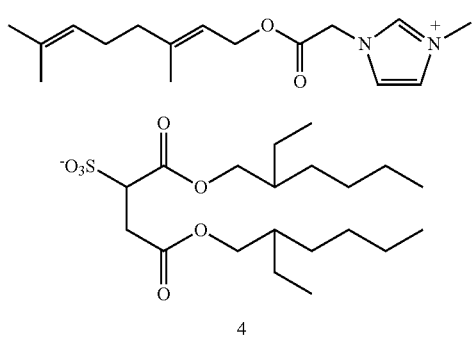

4

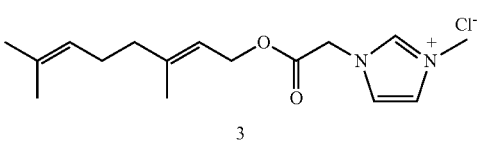

3

Figure 6:
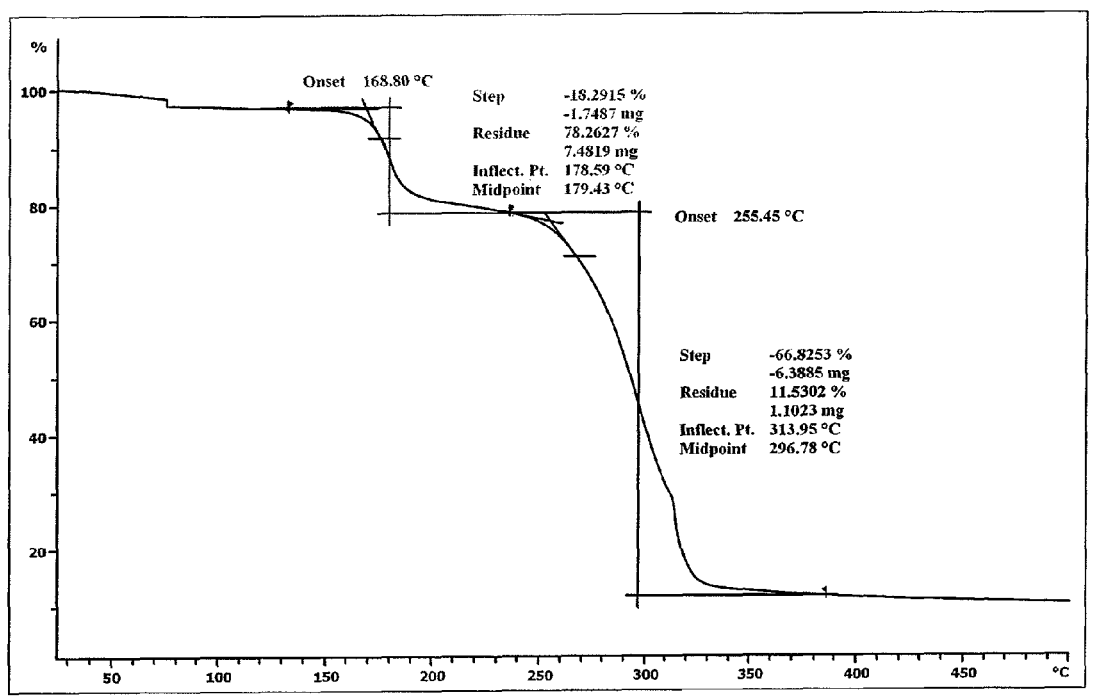
FIG. 6 depicts the decomposition of (E)-4-(3,7-dimethylocta-2,6-dienyloxy)-4-oxobutanoic acid versus on temperature. The first decomposition step represents the release of the volatile fragrance geraniol.

Ionic liquid-supported hydrophobic fragrance 4 shows, as typically for any ionic liquid, neglible volatility but can be decomposed by means of heat only to liberate geraniol (FIG. 6).

Food and pharmaceutical regulations restrict the palette of material used for sustained release. The invention also includes example for immobilization of the active compound on the anion of the ionic liquid delivery system, which can be completely composed of GRAS (Generally Recognized As Safe) compounds. A typical example of this type of ionic liquid delivery system includes the immobilization of fragrance alcohols as hemisuccinates that can be further deprotonated with any basic component, e.g. hydroxides of quaternary amines to give an ionic liquid.

ion or a second, charged active compound. Ionic liquid decomposition will than provide a neutral and a charged active fragrance or flavour in exactly the same dosage.

This invention also includes triple-functional salts, wherein a neutral active compound is covalently attached to a second, charged active compounds, replace to the typical structural elements that are present in ionic liquids, e.g. imidazolium cations. The constitution of which, can then be paired with a third charged active compounds, which will result in the delivery of 3 active compounds in the same rate and dosage.

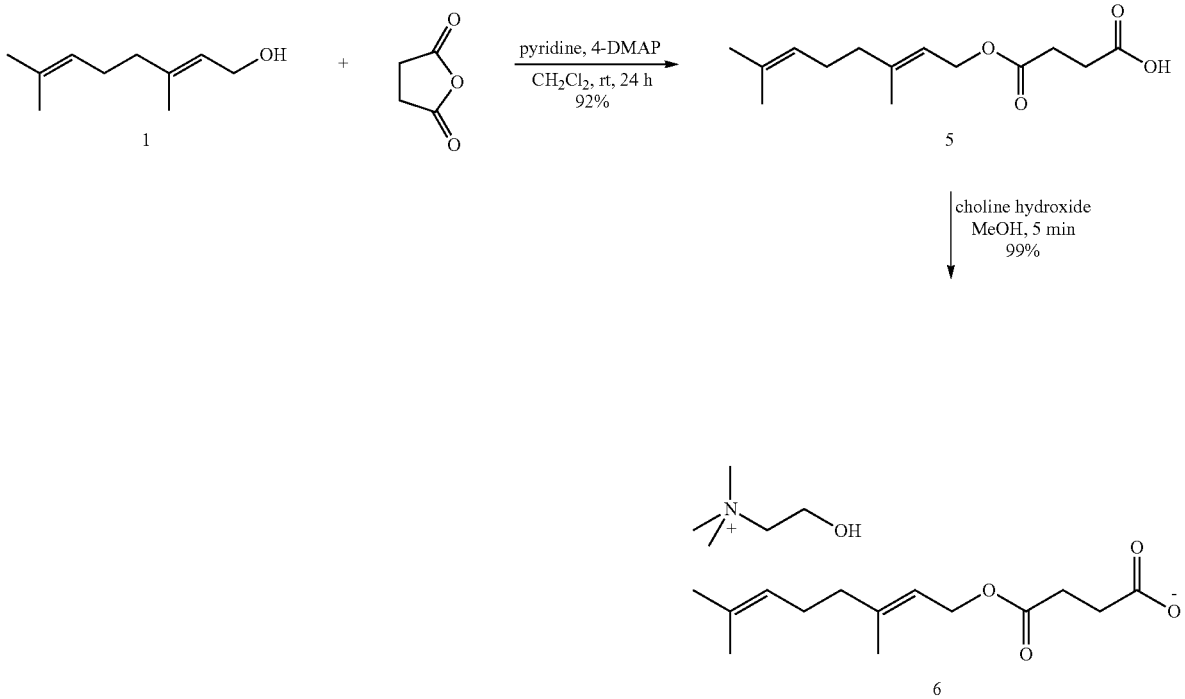

Cleavage of ionic liquid immobilized fragrance 6 by the process of acidic, basic or enzymatic ester hydrolysis will release the fragrance and leave only choline (a vitamine) and succinic acid, a compound that is generally recognized as safe (GRAS).

The invention also provides the possibility to form dual functioning salts by introduction of a second active counter

EXAMPLES

The following examples are set forth below to illustrate the methods and results according to the disclosed subject matter. These examples are not intended to be inclusive of all aspects of the subject matter disclosed herein, but rather to illustrate representative methods and results. All chemicals used were of analytical grade, purchased from Sigma-Aldrich (UK), and used without further purification unless otherwise noted. Commercially available solutions of hydroxides were titrated prior to use to determine the exact concentration.

Multiple Functional Co-Ionic Liquids

Example 1

Tetrabutylphosphonium Salicylate-Salicylic Acid

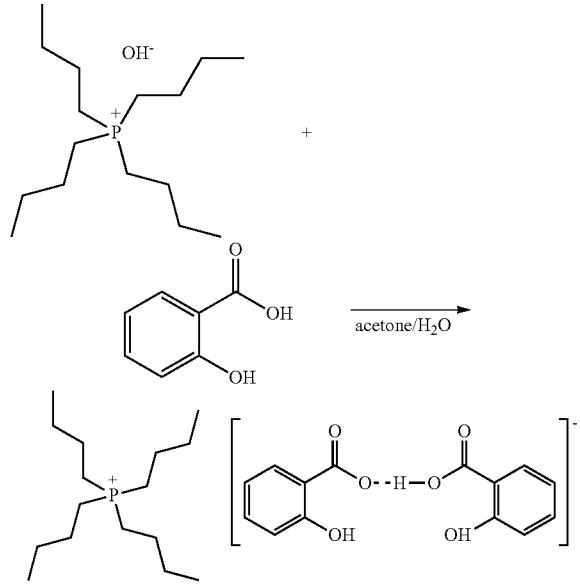

Salicylic acid (5-20 mmol) and tetrabutylphosphonium hydroxide (~40% sol. in $H_2O$) (3.414 g, 5 mmol) were dissolved in 20 ml of acetone stirred for 15 min at room temperature. The solvent was evaporated and the remaining viscous liquid was dried under reduced pressure (0.01 mbar, 50° C.) with stirring for 24 hrs. $^1$H-NMR (300 MHz, $d_6$-DMSO) δ(ppm)=7.74 (dd, $J_1$=7.7 Hz, $J_2$=1.9 Hz, 1H), 7.32 (dt, $J_1$=7.6 Hz, $J_2$=1.8 Hz, 1H), 6.8 (m, 2H), 2.20 (m, 4 H), 1.41 (m, 8 H), 0.9 (t, J=7.1 Hz, 6 H). $^{31}$P-NMR (121.5 MHz, $d_6$-DMSO) δ(ppm)=35.1. $^{13}$C-NMR (75 MHz, $d_6$-DMSO) δ(ppm)= 171.9(s), 163.1(s), 131.1 (d), 129.8(d), 120.6 (s), 115.7 (d), 115.6 (d), 23.3 (d, J=16.4 Hz), 22.6 (d, J=4.8 Hz), 17.3 (d, J=47.3 Hz), 13.2 (s).

TABLE I

| Composition P(Bu)$_4$:Sal | Appearance | mp [° C.][a] | $T_{5\% \, onset}$ [° C.][c] | water content [% m/m] |
|---|---|---|---|---|
| 1:1 | Solid | 57 | 312 | 0.0766 |
| 1:1.1 | Solid | 52 | 297 | 0.1359 |
| 1:1.2 | Solid | −54[b] | 211 | 0.1283 |
| 1:1.3 | Liquid | −54[b] | 207 | 0.2280 |
| 1:1.4 | Liquid | −51[b] | 209 | 0.1308 |
| 1:1.5 | Liquid | −52[b] | 206 | 0.1587 |
| 1:1.6 | Liquid | −50[b] | 200 | 0.3210 |
| 1:1.7 | Liquid | −48[b] | 194 | 0.1807 |
| 1:1.8 | Liquid | −47[b] | 198 | 0.1529 |
| 1:1.9 | Liquid | −46[b] | 198 | 0.2462 |
| 1:2 | Liquid | −46[b] | 192 | 0.1924 |
| 1:2.4 | Liquid | −45[b] | 184 | 0.1517 |
| 1:2.7 | Liquid | −43[b] | 173 | 0.1412 |
| 1:2.8 | Liquid | −43[b] | 169 | 0.1127 |

TABLE I-continued

| Composition P(Bu)$_4$:Sal | Appearance | mp [° C.][a] | $T_{5\% \, onset}$ [° C.][c] | water content [% m/m] |
|---|---|---|---|---|
| 1:3.0 | Liquid | −43[b] | 164 | |
| 1:3.1 | Suspension | −43[b] | | |
| 1:3.5 | Suspension | −45[b] | | |
| 1:3.7 | Suspension | −43[b] | 150 | 0.1033 |
| Salicylic acid | Solid | 158 (lit) | 136 | |

[a]determined on a Mettler Toledo Star$^e$ DSC unit by heating to 110° C. with 5° C./min and cooling with −2.5° C./min to −80° C. for 3 cycles.
[b]glass transition temperature.
[c]determined on a Mettler Toledo Star$^e$ TGA/DSC unit by heating from 25° C. to 600° C. with 5° C./min under nitrogen.

Table I shows thermal data and water content of different tetrabutylphosphonium salicylate-salicylic acid co-ionic liquids.

Figure 2:
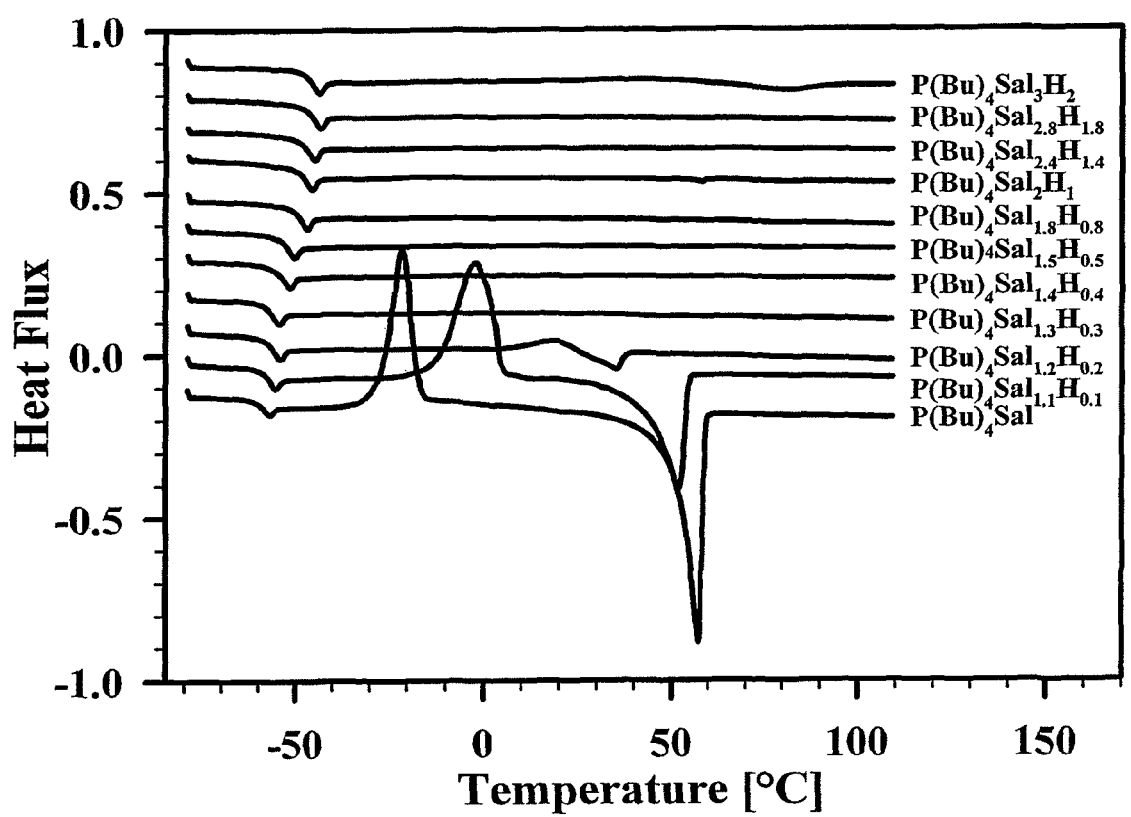
FIG. 2 depicts the depression and elimination of the melting point of $P(Bu)_4[Sal_xH_{x-1}]$ in a series of co-ionic liquids comprising oligomeric anions.
Figure 3:
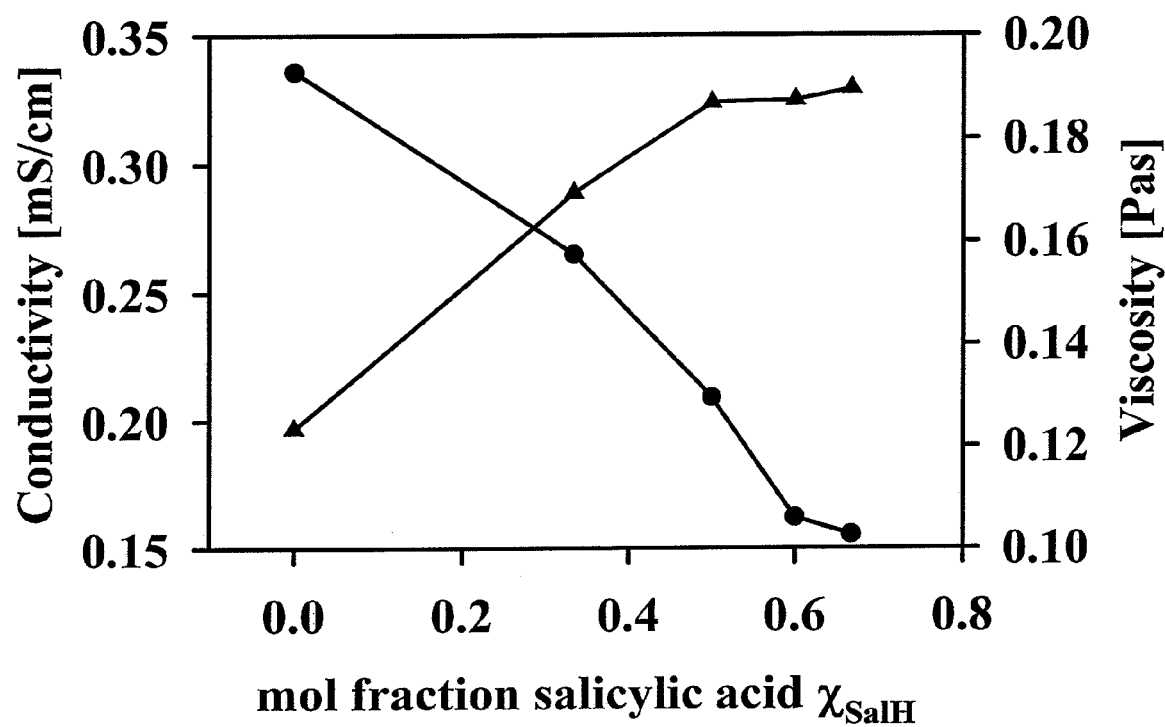
FIG. 3 depicts the conductivity and viscosity of various $P(Bu)_4[Sal_xH_{x-1}]$ compositions in a series of co-ionic liquids comprising oligomeric anions.

FIG. 2 is a plot of the melting point depression and melting point elimination curves for the data depicted in Table I.

FIG. 3 depicts the conductivity of different P(Bu)$_4$[Sal$_x$H] compositions in a series of co-ionic liquids comprising oligomeric anions.

Example 2

Tetrabutylphosphonium Salicylate-salicylic Acid-solvent-free Synthesis Via Grinding

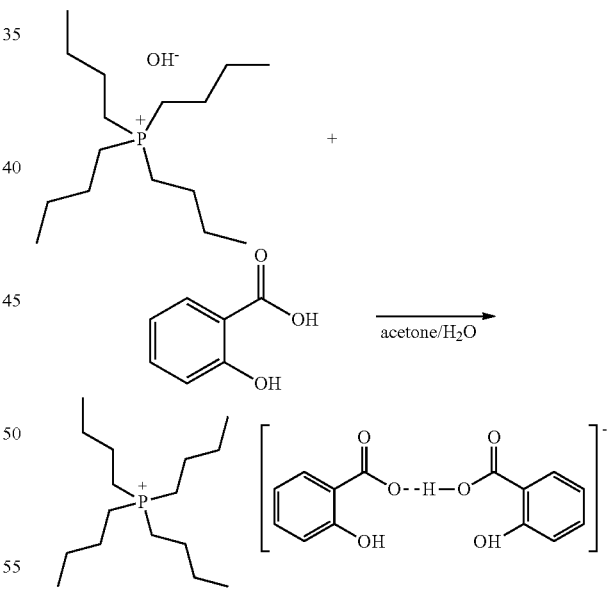

Solid tetrabutylphosphonium salicylate (3.963 g, 10 mmol) and Salicylic acid (1.601 g, 10 mmol) were grinded for 2 minutes in a mortar until a colorless, free-flowing liquid was obtained. Physical data were similar to those obtained with conventional synthesis (example 1).

$^1$H-NMR (300 MHz, $d_6$-DMSO) δ(ppm)=7.74 (dd, $J_1$=7.7 Hz, $J_2$=1.87 Hz), 7.32 (dt, $J_1$=7.6 Hz, $J_2$=1.80 Hz, 1H), 6.77 (m, 2H), 2.20 (m, 4 H), 1.41 (m, 8 H), 0.9 (t, J=7.1 Hz, 6 H). $^{13}$C-NMR (75 MHz, $d_6$-DMSO) δ(ppm)=172.0 (s), 162.3 (s), 133.8 (d), 130.5 (d), 117.9 (d), 117.1 (s), 116.8 (d), 23.30 (d, J=15.94 Hz), 22.61 (d, J=5.31 Hz), 17.31 (d, J=47.82 Hz), 13.73 (s).

Example 3

Methyltributylammonium Salicylate-salicylic Acid

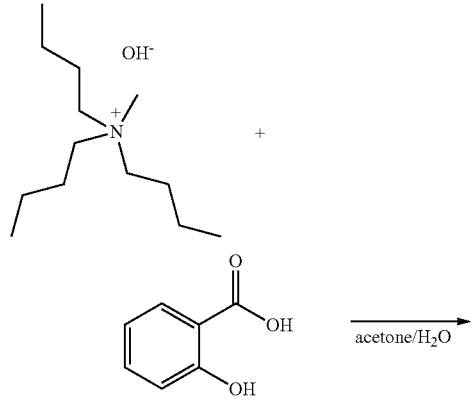

Salicylic acid (5-20 mmol) and tributylmethylammonium hydroxide (5 mmol, 40% solution in $H_2O$) were dissolved in 20 ml of acetone stirred for 15 min at room temperature. The solvent was evaporated and the remaining viscous liquid was dried at 0.1 mbar with stirring for 24 hrs.

$^1$H-NMR (300 MHz, $d_6$-DMSO) δ(ppm)=7.63 (dd, $J_1$=7.7 Hz, $J_2$=1.9 Hz, 1H), 7.10 (m, 1H), 6.57 (m, 2H), 3.19 (m, 6H), 2.94 (s, 3H), 1.59 (m, 6H), 1.29 (sext, J=7.4 Hz, 6H), 0.9 (t, J=7.4 Hz, 9H). $^{13}$C-NMR (75 MHz, $d_6$-DMSO) δ(ppm)= 171.9, 162.0, 133.4, 130.1, 117.5, 116.9, 60.4, 47.5, 23.4, 19.2, 13.5.

TABLE II

| Ratio N(Bu)$_3$Me:Sal | Appearance | mp [° C.][a] | $T_{5\% \, onset}$ [° C.][c] |
|---|---|---|---|
| 1:1 | solid | 83 | 193 |
| 1:2 | liquid | −37[b] | 196 |
| 1:3 | liquid | −41[b] ($T_g$) | 177 |

[a]determined on a Mettler Toledo Star$^e$ DSC unit by heating to 110° C. with 5° C./min and cooling with −2.5° C./min to −80° C. for 3 cycles.
[b]glass transition temperature.
[c]determined on a Mettler Toledo Star$^e$ TGA/DSC unit by heating from 25° C. to 600° C. with 5° C./min under nitrogen.

Table II shows thermal data of different tributylmethylammonium salicylate-salicylic acid co-ionic liquids.

Example 4

Choline Salicylate-salicylic Acid

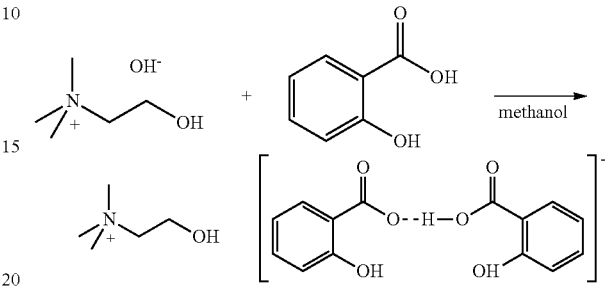

Salicylic acid (5 or 10 mmol) and choline hydroxide (5 mmol, 40% solution in MeOH) were dissolved in 20 ml of methanol and stirred for 15 min at room temperature. The solvent was evaporated and the remaining viscous liquid was dried at 0.1 mbar with stirring for 24 hrs.

$^1$H-NMR (300 MHz, $d_6$-DMSO) δ(ppm)=7.64 (dd, $J_1$=7.4 Hz, $J_2$=1.9 Hz, 1H), 7.3 (m, 1H), 6.6 (m, 2H), 3.8 (m, 2H), 3.4 (m, 2H), 3.1 (s, 9H).

TABLE III

| Ratio Cho:Sal | Appearance | mp [° C.][a] | $T_{5\% \, onset}$ [° C.][c] |
|---|---|---|---|
| 1:1 | solid | 48 (lit) | 203 |
| 1:2 | liquid | −41[b] | 173 |

[a]determined on a Mettler Toledo Star$^e$ DSC unit by heating to 110° C. with 5° C./min and cooling with −2.5° C./min to −80° C. for 3 cycles.
[b]glass transition temperature.
[c]determined on a Mettler Toledo Star$^e$ TGA/DSC unit by heating from 25° C. to 600° C. with 5° C./min under nitrogen.

Table III shows thermal data of different choline salicylate-salicylic acid co-ionic liquids.

Example 5

Cetylpyridinium Salicylate-salicylic Acid

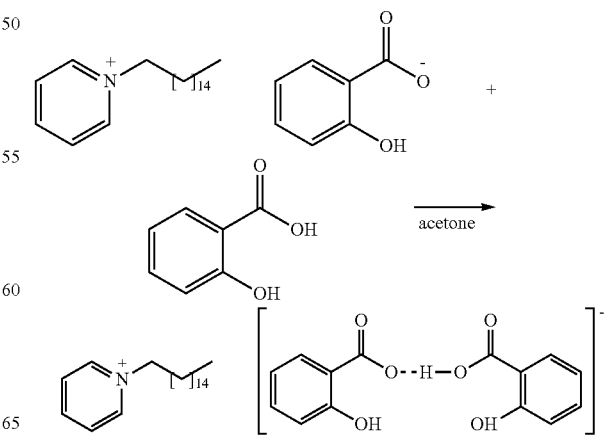

Salicylic acid (5-15 mmol) and cetylpyridinium salicylate (5 mmol) were dissolved in 20 ml of acetone and stirred for 15 min at room temperature. The solvent was evaporated and the remaining viscous liquid was dried at 0.1 mbar with stirring for 24 hrs.

$^1$H-NMR (300 MHz, $d_6$-DMSO) δ(ppm)=9.12 (d, J=6.1 Hz, 2H), 8.59 (t, J=8.3 Hz, 1H), 8.16 (t, J=7.3 Hz, 2H), 7.64 (d, 7.5 Hz, 1H), 7.12 (t, J=7.5, 1H), 6.57 (m, 2H), 4.59 (t, J=7.4 Hz, 2H), 1.88 (m, 2H), 1.22 (s, 27H), 0.84 (t, J=7.1 Hz, 3H). $^{13}$C-NMR (75 MHz, $d_6$-DMSO) δ(ppm)=171.8, 163.4, 145.8, 145.2, 131.4, 130.2, 128.4, 121.1, 116.1, 160.0, 61.2, 31.7, 31.2, 29.4, 29.3, 29.2, 29.1, 28.8, 25.8, 22.5, 14.2.

TABLE IV

| Ratio CetPy:Sal | Appearance | mp [° C.][a] | $T_{5\% \, onset}$ [° C.][c] |
|---|---|---|---|
| 1:1 | solid | 71 | 206 |
| 1:2 | solid | 54 | 184 |
| 1:3 | solid | −21[b] | 162 |

[a]determined on a Mettler Toledo Star$^e$ DSC unit by heating to 110° C. with 5° C./min and cooling with −2.5° C./min to −80° C. for 3 cycles.
[b]glass transition temperature.
[c]determined on a Mettler Toledo Star$^e$ TGA/DSC unit by heating from 25° C. to 600° C. with 5° C./min under nitrogen.

Table IV shows thermal data of different cetylpyridinium salicylate-salicylic acid co-ionic liquids.

Example 6

Tetrabutylphosphonium Ibuprofenate-ibuprofenic Acid

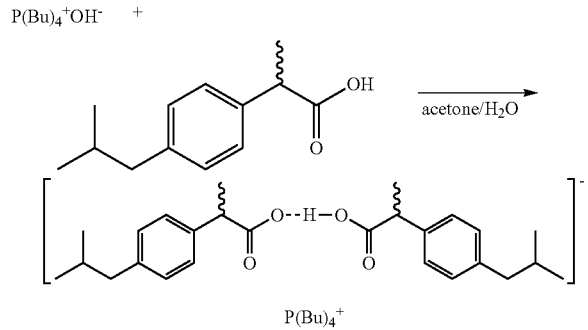

Ibuprofenic acid (5-15 mmol) and tetrabutylphosphonium hydroxide (~40% sol. in $H_2O$) (3.414 g, 5 mmol) were dissolved in 20 ml of acetone and stirred for 15 min at room temperature. The solvent was evaporated and the remaining viscous liquid was dried at 0.1 mbar with stirring for 24 hrs.
$^1$H-NMR (300 MHz, $d_6$-DMSO) δ(ppm)=7.13 (d, J=8.1 Hz, 2H), 6.94 (d, 8.1 Hz, 2H), 3.21 (q, 7.7 Hz, 1H), 2.48 (m, 2H), 2.36 (d, 7.3 Hz, 2H), 2.14 (m, 8H), 1.77 (sept, 6.2 Hz, 1H), 1.40 (m, 16 H), 1.18 (d, J=7.0 Hz, 3H), 0.91 (t, 7.0 Hz, 12H), 0.84 (d, J=7.0 Hz, 6H). $^{13}$C-NMR (75 MHz, $d_6$-DMSO) δ(ppm)=174.8, 144.2, 136.9, 127.8, 127.2, 49.3, 44.4, 29.7, 23.4 (d, J=15.8 Hz), 22.7 (d, J=4.7 Hz), 22.2, 20.5, 17.3 (d, J=48.1 Hz), 13.3.

TABLE V

| Ratio P(Bu)$_4$Ibu | Appearance | $T_g$ [° C.][a] | $T_{5\% \, onset}$ [° C.][b] |
|---|---|---|---|
| 1:1 | liquid | −43 | 234 |
| 1:2 | liquid | −40 | 264 |
| 1:3 | liquid | −39 | 189 |

[a]determined on a Mettler Toledo Star$^e$ DSC unit by heating to 110° C. with 5° C./min and cooling with −2.5° C./min to −80° C. for 3 cycles.
[b]determined on a Mettler Toledo Star$^e$ TGA/DSC unit by heating from 25° C. to 600° C. with 5° C./min under nitrogen.

Table V shows thermal data of different tetrabutylphosphonium ibuprofenate-ibuprofenic co-ionic liquids.

Example 7

Tetrabutylphosphonium Lactate-lactic Acid

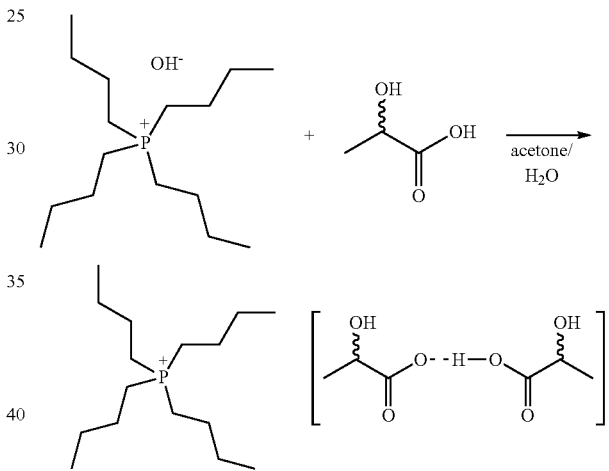

Lactic acid (5-15 mmol) and tetrabutylphosphonium hydroxide (~40% sol. in $H_2O$) (3.414 g, 5 mmol) were dissolved in 20 ml of acetone and stirred for 15 min at room temperature. The solvent was evaporated and the remaining viscous liquid was dried at 0.1 mbar with stirring for 24 hrs.
$^1$H-NMR (300 MHz, $d_6$-DMSO) δ(ppm)=3.84 (br s, 1H), 3.44 (q, J=6.7 Hz, 1H), 2.18 (m, 8H), 1.41 (m, 16H), 1.05 (d, J=7.2 Hz, 3H), 0.91 (t, J=6.7 Hz, 12H). $^{31}$P-NMR (121.5 MHz, $d_6$-DMSO) δ(ppm)=35.0. $^{13}$C-NMR (75 MHz, $d_6$-DMSO) δ(ppm)=176.8, 67.3, 23.72 (d, J=15.5 Hz), 23.01 (d, J=4.7 Hz), 21.91, 17.70 (d, J=47.9 Hz), 13.62 (s).

TABLE VI

| Ratio P(Bu)$_4$Lac | Appearance | $T_g$ [° C.][a] | $T_{5\% \, onset}$[b] |
|---|---|---|---|
| 1:1 | liquid | 1.78 (mp) | 262 |
| 1:2 | liquid | −56 | 215 |
| 1:3 | liquid | −55 | 176 |

[a]determined on a Mettler Toledo Star$^e$ DSC unit by heating to 110° C. with 5° C./min and cooling with −2.5° C./min to −80° C. for 3 cycles.
[b]determined on a Mettler Toledo Star$^e$ TGA/DSC unit by heating from 25° C. to 600° C. with 5° C./min. under nitrogen.

Table VI shows thermal data of different tetrabutylphosphonium lactate-lactic acid co-ionic liquids.

Example 8

Lidocaine Salicylates

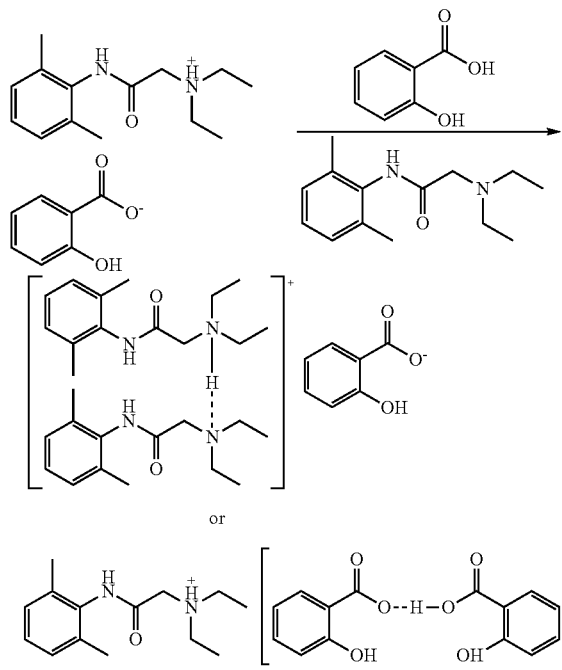

Salicylic acid or lidocaine free base (0.5, 1, 1.5 or 2 eq.) and lidocaine salicylate were suspended in acetone (20 ml) and stirred at room temperature until a clear solution was obtained. The solvent was evaporated and remaining volatile material removed under vacuum (0.01 mbar, 40° C.). $^1$H-NMR (300 MHz, $d_6$-DMSO) δ(ppm)=10.05 (br s, 1H), 7.72 (dd, $J_1$=7.8 Hz, $J_2$=1.8 Hz, 1H), 7.24 (m, 1H), 7.09 (s, 3H), 6.70 (m, 2H), 3.98 (s, 2H), 3.10 (q, J=7.3 Hz, 4 H), 2.16 (s, 6H), 1.22 (t, J=7.3 Hz, 6H). $^{13}$C-NMR (75 MHz, $d_6$-DMSO) δ(ppm)=171.9, 164.6, 161.9, 135.0, 134.0, 133.4, 130.1, 127.8, 126.9, 117.6, 116.9, 116.4, 53.3, 48.3, 18.1, 9.5.

TABLE VII

| Lid | Sal | Appearance | $T_g$ [° C.][a] | $T_{onset\ 5\%}$ [° C.][b] |
|---|---|---|---|---|
| 3 | 1 | solid | −32 | 161 |
| 2.5 | 1 | solid | −25 | 137 |
| 2 | 1 | glass | −15 | 154 |
| 1.5 | 1 | glass | −1 | 169 |
| 1 | 1 | glass | 19 | 161 |
| 1 | 1.5 | viscous liquid | 13 | 142 |
| 1 | 2 | viscous liquid | 3 | 138 |
| 1 | 2.5 | solid | −4 | 132 |
| 1 | 3 | solid | −3 | 128 |
| 1 |  | solid | 69 (mp) | 152 |
|  | 1 | solid | 160 (mp) | 134 |

[a]determined on a Mettler Toledo Star$^e$ DSC unit by heating to 110° C. with 5° C./min and cooling with −2.5° C./min to −80° C. for 3 cycles.
[b]determined on a Mettler Toledo Star$^e$ TGA/DSC unit by heating from 25° C. to 600° C. with 5° C./min. under nitrogen.

Table VII shows thermal data of different lidocaine salicylateco-ionic liquids.

FIG. 4 depicts the depression of glass transition and saturation of double functional co-ionic liquids based on lidocainium salicylate.

Example 9

Ephedrine Salicylate

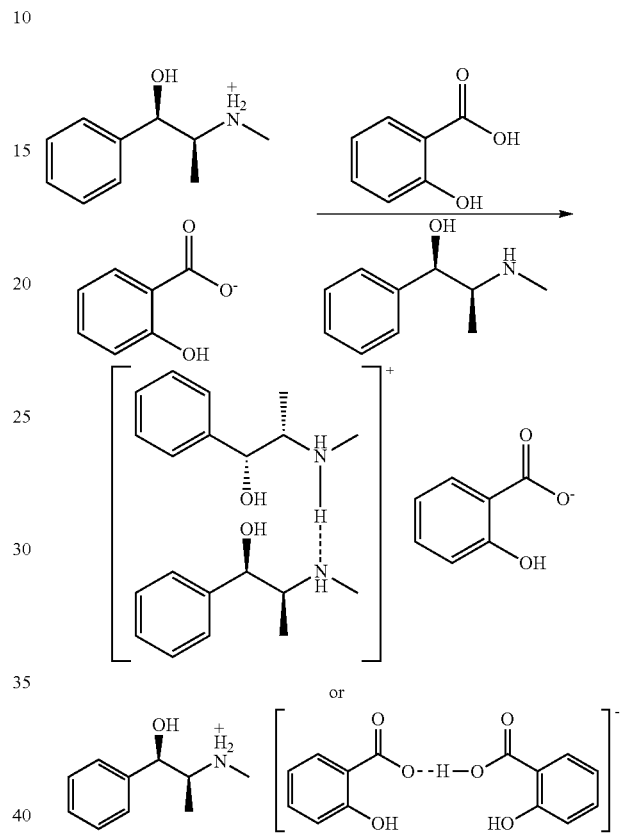

Salicylic acid or ephedrine free base (0.5, 1, 1.5 or 2 eq.) and ephedrinium salicylate were suspended in acetone (20 ml) and stirred at room temperature until a clear solution was obtained. The solvent was evaporated and remaining volatile material removed under vacuum (0.01 mbar, 40° C.). $^1$H-NMR (300 MHz, $d_6$-DMSO) δ(ppm)=9.30 (br s, 2H), 7.76 (dd, $J_1$=7.7 Hz, $J_2$=1.8 Hz, 1H), 7.38 (m, 4H), 7.24 (m, 2H), 6.70 (m, 2H), 6.48 (br s, 1H), 5.21 (s, 1H), 3.41 (m, 1H), 2.69 (s, 3H), 0.95 (d, J=6.8 Hz, 3H). $^{13}$C-NMR (75 MHz, $d_6$-DMSO) δ(ppm)=172.9, 162.1, 141.4, 132.0, 130.3, 128.2, 127.2, 125.8, 119.6, 116.8, 116.0, 69.6, 59.3, 30.6, 9.1.

TABLE VIII

| Ratio Eph:Sal | Appearance | mp [° C.][a] | $T_{onset\ 5\%}$ [° C.][c] |
|---|---|---|---|
| 1:3 | solid | 61 | — |
| 1:2 | solid | 61 | 130 |
| 1:1 | solid | 97 | 161 |
| 2:1 | glass | 2[b] | 127 |
| 3:1 | liquid | −5[b] | 123 |

[a]determined on a Mettler Toledo Star$^e$ DSC unit by heating to 110° C. with 5° C./min and cooling with −80° C. for 3 cycles.
[b]glass transition temperature
[c]determined on a Mettler Toledo Star$^e$ TGA/DSC unit by heating from 25° C. to 600° C. with 5° C./min. under nitrogen.

Table VIII shows thermal data of different ephedrinium salicylate co-ionic liquids.

Example 10

Ephedrine Salicylate-solvent-free Synthesis Via Grinding

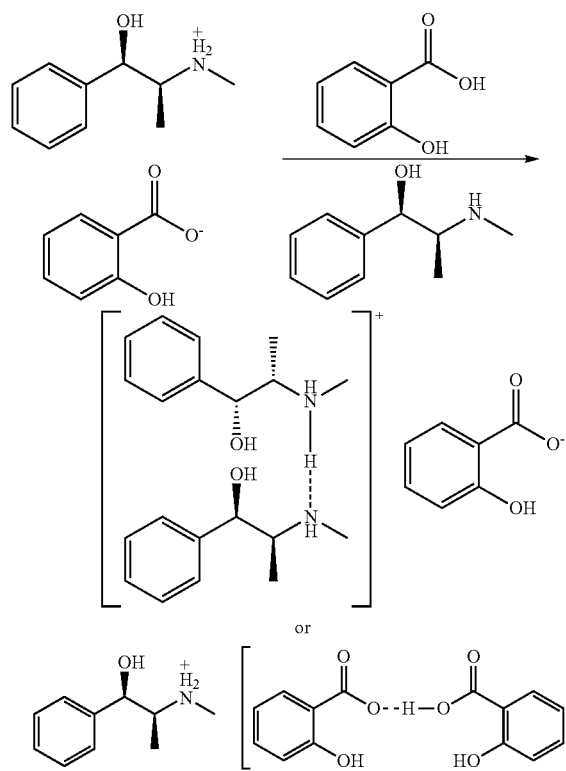

Salicylic acid or ephedrine free base (0.5, 1, 1.5 or 2 eq.) and ephedrinium salicylate were grinded for 15 minutes in a mortar. Analytical data were similar to those obtained in conventional synthesis. $^1$H-NMR (300 MHz, d$_6$-DMSO) δ(ppm)=9.30 (br s, 2H), 7.76 (dd, J$_1$=7.7 Hz, J$_2$=1.8 Hz, 1H), 7.38 (m, 4H), 7.24 (m, 2H), 6.70 (m, 2H), 6.48 (br s, 1H), 5.21 (s, 1H), 3.41 (m, 1H), 2.69 (s, 3H), 0.95 (d, J=6.8 Hz, 3H). $^{13}$C-NMR (75 MHz, d$_6$-DMSO) δ(ppm)=172.9, 162.1, 141.4, 132.0, 130.3, 128.2, 127.2, 125.8, 119.6, 116.8, 116.0, 69.6, 59.3, 30.6, 9.1.

TABLE IX

| Ratio Eph:Sal | Appearance | mp [° C.][a] | T$_{onset\,5\%}$ [° C.][c] |
|---|---|---|---|
| 1:4 | solid | 61 | 124 |
| 1:3 | solid | 61 | 122 |
| 1:2 | solid | 61 | 131 |
| 1:1.4 | solid | 61 | 153 |
| 1:1.3 | solid | 60 | 147 |
| 1:1.2 | solid | 60 | 154 |
| 1:1.1 | solid | 91 | 163 |
| 1:1 | solid | 97 | 161 |
| 2:1 | glass | 5[b] | 118 |
| 3:1 | liquid | −4[b] | 115 |

[a]determined on a Mettler Toledo Star$^e$ DSC unit by heating to 110° C. with 5° C./min and cooling with 5° C./min to −80° C. for 3 cycles.
[b]glass transition temperature
[c]determined on a Mettler Toledo Star$^e$ TGA/DSC unit by heating from 25° C. to 600° C. with 5° C./min. under nitrogen.

Table IX shows thermal data of different ephedrinium salicylate co-ionic liquids prepared by grinding.

Example 11

Ephedrine Salicylate-solvent-free Synthesis in Molten State

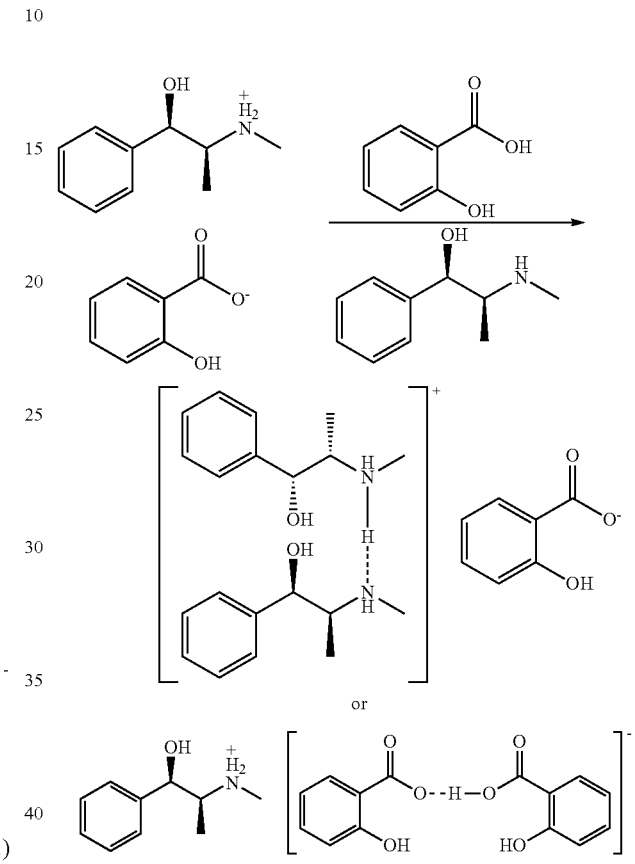

Salicylic acid and ephedrine free base (1, 2 or 3 eq.) were molten in a hot mortar until a free-flowing clear liquid was obtained. The mixture was cooled to room temperature and, in case of solid products grinded to obtain colourless powders. $^1$H-NMR (300 MHz, d$_6$-DMSO) δ(ppm)=9.30 (br s, 2H), 7.76 (dd, J$_1$=7.66 Hz, J$_2$=1.80 Hz, 1H), 7.38 (m, 4H), 7.24 (m, 2H), 6.70 (m, 2H), 6.48 (br s, 1H), 5.21 (s, 1H), 3.41 (m, 1H), 2.69 (s, 3H), 0.95 (d, J=6.76 Hz, 3H). $^{13}$C-NMR (75 MHz, d$_6$-DMSO) δ(ppm)=172.9, 162.1, 141.4, 132.0, 130.3, 128.2, 127.2, 125.8, 119.6, 116.8, 116.0, 69.6, 59.3, 30.6, 9.1.

TABLE X

| Ratio Eph:Sal | Appearance | mp [° C.][a] | T$_{onset\,5\%}$ [° C.][c] |
|---|---|---|---|
| 1:3 | solid | 61 | 135 |
| 1:2 | solid | 61 | 133 |
| 1:1 | solid | 97 | 161 |
| 2:1 | glass | 7[b] | 144 |
| 3:1 | liquid | −2[b] | 128 |

[a]determined on a Mettler Toledo Star$^e$ DSC unit by heating to 110° C. with 5° C./min and cooling with 5° C./min to −80° C. for 3 cycles.
[b]glass transition temperature
[c]determined on a Mettler Toledo Star$^e$ TGA/DSC unit by heating from 25° C. to 600° C. with 5° C./min under nitrogen.

Table X shows thermal data of different ephedrinium salicylate co-ionic liquids prepared by melting.

Example 12

Ephedrinium Clofibrate-solvent-free Synthesis Via Melting

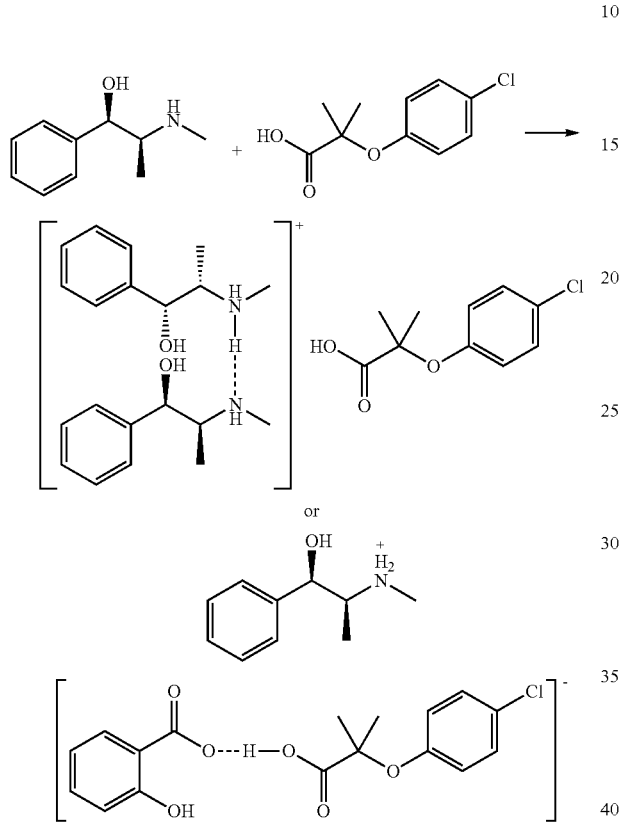

Clofibric acid (1 or 2 eq.) and ephedrine free base (1 or 2 eq.) were molten in a hot mortar until a free-flowing clear liquid was obtained. The mixture was cooled to room temperature and, in case of solid products, grinded to obtain yellow powders. $^1$H-NMR (300 MHz, $d_6$-DMSO) δ(ppm)= 9.36 (br s, 2H), 7.30 (m, 5H), 7.19 (d, J=8.8 Hz, 2H), 6.82 (d, J=8.8 Hz, 2H), 5.10 (s, 1H), 3.12 (m, 1H), 2.52 (s, 3H), 1.41 (s, 6H), 0.85 (d, J=6.6 Hz, 3H). $^{13}$C-NMR (75 MHz, $d_6$-DMSO) δ(ppm)=176.8, 155.5, 141.8, 128.5, 128.0, 126.9, 125.8, 123.4, 119.2, 80.2, 69.8, 59.5, 30.7, 25.8, 9.6.

TABLE XI

| Ratio Eph:Clofib | Appearance | mp [° C.][a] | $T_{onset\ 5\%}$ [° C.][c] |
|---|---|---|---|
| 1:2 | glass | 12[b] | 182 |
| 1:1 | solid | 131 | 169 |
| 2:1 | glass | 7[b] | 135 |

[a] determined on a Mettler Toledo Star$^e$ DSC unit by heating to 110° C. with 5° C./min and cooling with 5° C./min to −80° C. for 3 cycles.
[b] glass transition temperature
[c] determined on a Mettler Toledo Star$^e$ TGA/DSC unit by heating from 25° C. to 600° C. with 5° C./min. under nitrogen.

Table XI shows thermal data of different ephedrinium clofibrate co-ionic liquids prepared by melting.

Example 13

Caffeine Salicylate-solvent-free Synthesis Via Grinding

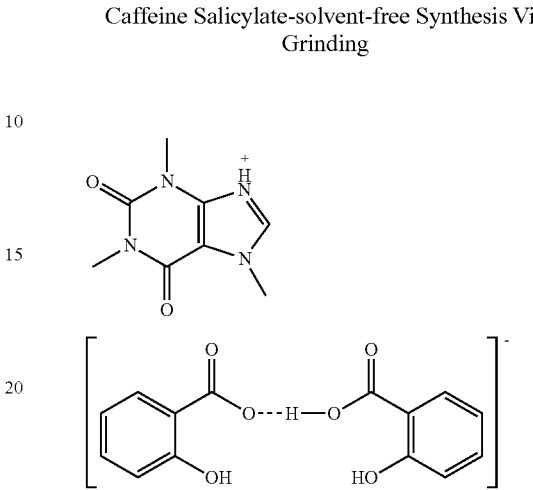

Caffeine salicylate (19.40 mg, 0.058 mmol) and salicylic acid (8.06 mg, 0.058 mmol) were grinded for 15 minutes in a mortar at room temperature. A colorless powder was obtained.

$^1$H-NMR (300 MHz, $d_6$-DMSO) δ(ppm)=11.29 (br s, 1H), 8.01 (s, 1H), 7.90 (dd, $J_1$=8.1 Hz, $J_2$=1.4 Hz, 2H), 7.51 (t, J=7.83 Hz, 2H), 6.94 (m, 4H), 3.07 (s, 3H), 3.41 (s, 3H), 3.21 (s, 3H). mp 122° C., $T_{5\%onset}$ 111° C.

Example 14

Tetrabutylphosphonium Salicylate-ibuprofenic Acid P(Bu)$_4$[SalIbu]H

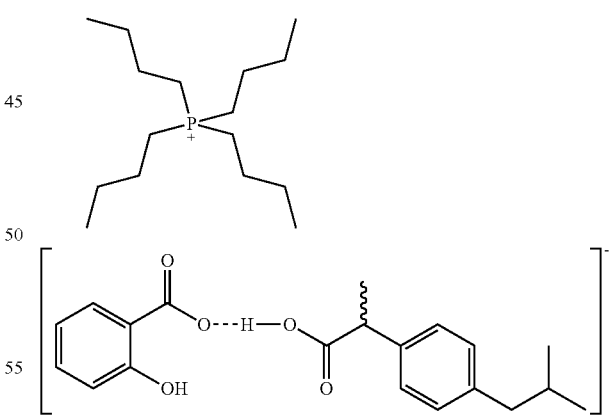

Ibuprofenic acid (1.032 g, 5 mmol), salicylic acid (0.6909 g, 5 mmol) and tetrabutylphosphonium hydroxide (~40% sol. in H$_2$O) (3.414 g, 5 mmol) were dissolved in 20 ml of acetone and stirred for 15 min at room temperature. The solvent was evaporated and the remaining viscous liquid was dried at 0.01 mbar with stirring for 24 hrs. The desired compound is isolated as a colourless liquid. $^1$H-NMR (300 MHz, $d_6$-DMSO) δ(ppm)=7.65 (dd, $J_1$=7.6 Hz, $J_2$=1.8 Hz, 1H), 7.18 (d, 8.0 Hz, 2H), 7.11 (m, 3H), 6.59 (m, 2H), 3.63 (q, J=7.2 Hz, 2H), 2.41

(d, 7.2 Hz, 2H), 2.17 (m, 8H), 1.80 (sept, J=6.70, 1H), 1.42 (m, 16 H), 1.34 (s, J=7.1 Hz, 3H), 0.9 (t, J=6.9 Hz, 12 H), 0.85 (d, 6.7 Hz, 6H). $^{13}$C-NMR (75 MHz, d$_6$-DMSO) δ(ppm)= 175.4, 171.2, 162.9, 139.5, 138.5, 131.3, 129.9, 128.9, 127.1, 115.9, 115.8, 44.3, 44.2, 29.6, 23.3 (d, J=15.8 Hz), 22.6 (d, 4.8 Hz), 22.2, 18.5, 17.3 (47.6 Hz), 13.7.

$T_g$ –45° C., $T_{5\%onset}$ 181° C.

Example 15

Tetrabutylphosphonium Salicylate-camphorsulfonic Acid P(Bu)$_4$[SalCSA]H

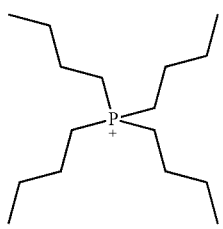

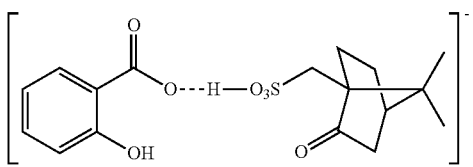

Camphorsulphonic acid (5 mmol), salicylic acid (0.6909 g, 5 mmol) and tetrabutylphosphonium hydroxide (~40% sol. in H$_2$O) (3.414 g, 5 mmol) were dissolved in 20 ml of acetone and stirred for 15 min at room temperature. The solvent was evaporated and the remaining viscous liquid was dried at 0.01 mbar with stirring for 24 hrs. The desired compound is isolated as a colourless liquid; $^1$H-NMR (300 MHz, d$_6$-DMSO) δ(ppm)=7.79 (dd, J$_1$=7.9 Hz, J$_2$=1.8 Hz), 7.52 (m, 1H), 6.94 (m, 3H), 2.97 (d, J=14.8 Hz, 1H), 2.71 (quin, J=10.8 Hz, 1H), 2.36 (d, J=14.8 Hz, 1H), 2.19 (m, 9H), 1.93 (t, J=4.5 Hz, 1H), 1.84 (m, 2H), 1.42 (m, 16 H), 1.26 (m, 2H), 1.05 (s, 3H), 0.91 (t, J=6.9 Hz, 12H), 0.74 (s, 3H). $T_g$ –33° C., $T_{5\% onset}$ 203° C.

Example 16

Tetrabutylphosphonium Salicylate-lactic Acid P(Bu)$_4$[SalLac]H

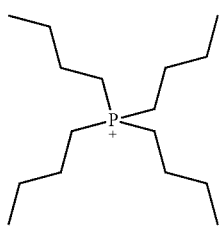

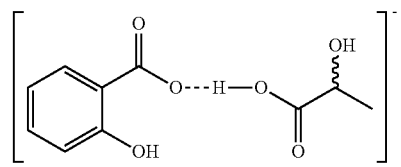

Lactic acid (0.4504 g, 5 mmol), salicylic acid (0.6909 g, 5 mmol) and tetrabutylphosphonium hydroxide (~40% sol. in H$_2$O) (3.414 g, 5 mmol) were dissolved in 20 ml of acetone and stirred for 15 min at room temperature. The solvent was evaporated and the remaining viscous liquid was dried at 0.01 mbar with stirring for 24 hrs. The desired compound is isolated as a colourless liquid; $^1$H-NMR (300 MHz, d$_6$-DMSO) δ(ppm)=7.63 (dd, J$_1$=7.6 Hz, J$_2$=1.9 Hz), 7.11 (m, 1H), 6.58 (m, 3H), 4.03 (q, J=6.9 Hz, 1H), 2.17 (m, 8H), 1.42 (m, 16 H), 1.23 (d, 7.0 Hz, 3H), 0.90 (t, J=7.3 Hz, 12 H). $^{31}$P-NMR (121.5 MHz, d$_6$-DMSO) δ(ppm)=35.0. $^{13}$C-NMR (75 MHz, d$_6$-DMSO) δ(ppm)=176.3, 171.1, 163.0, 131.2, 129.9, 120.5, 117.8, 115.767.3, 23.4 (d, J=15.8 Hz), 22.6 (d, J=4.3 Hz), 20.5, 17.3 (d, J=47.7 Hz), 13.3 (s).

$T_g$ –53° C., $T_{5\%onset}$ 178° C.

Example 17

Tetrabutylphosphonium Salicylate-cinnamic Acid P(Bu)$_4$[SalCinn]H

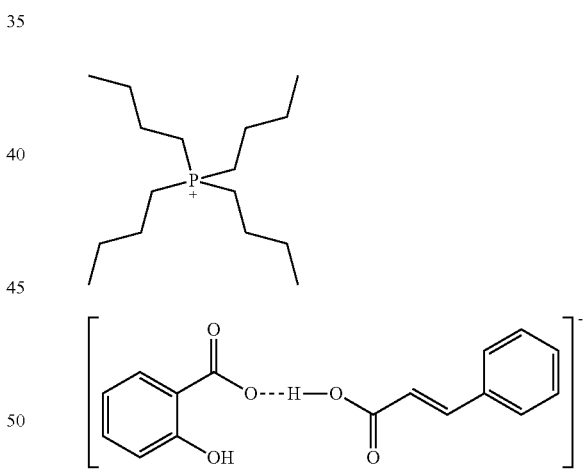

Cinnamic acid (0.7408 g, 5 mmol), salicylic acid (0.6909 g, 5 mmol) and tetrabutylphosphonium hydroxide (~40% sol. in H$_2$O) (3.414 g, 5 mmol) were dissolved in 20 ml of acetone stirred and for 15 min at room temperature. The solvent was evaporated and the remaining viscous liquid was dried at 0.1 mbar with stirring for 24 hrs. Identity and purity was confirmed via $^1$H NMR. The desired compound is isolated as a colourless liquid; $^1$H-NMR (300 MHz, d$_6$-DMSO) δ(ppm)= 7.67 (m, 3H), 7.57 (d, J=19.1 Hz, 1H), 7.41 (m, 3H), 7.12 (m, 1H), 6.56 (m, 3H), 2.17 (m, 8H), 14.1 (m, 16.H), 0.91 (t, J=6.9 Hz, 12 H). $^{31}$P-NMR (121.5 MHz, d$_6$-DMSO) δ(ppm)=35.1. $^{13}$C-NMR (75 MHz, d$_6$-DMSO) δ(ppm)=171.2, 167.6, 163.0, 143.3, 134.4, 131.1, 130.0, 129.9, 128.9, 128.1, 120.7, 120.0, 115.7, 115.6, 23.3 (d, J=15.9 Hz), 22.6 (d, 4.2 Hz), 17.3 (47.8 Hz), 13.2 (s). $T_g$ −43° C., $T_{5\%onset}$ 191° C.

Example 18

Tetrabutylphosphonium Ibuprofenate-niacin
P(Bu)$_4$[IbuNia]H

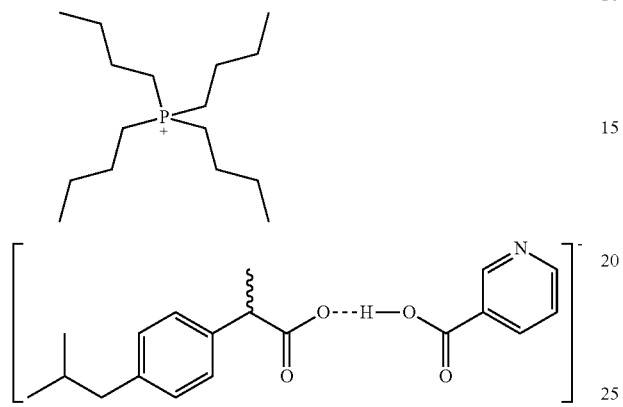

Ibuprofenic acid (1.0315 g, 5 mmol), niacine (0.6155 g, 5 mmol) and tetrabutylphosphonium hydroxide (~40% sol. in H$_2$O) (3.414 g, 5 mmol) were dissolved in 20 ml of acetone and stirred for 15 min at room temperature. The solvent was evaporated and the remaining viscous liquid was dried at 0.01 mbar with stirring for 24 hrs. Identity and purity was confirmed via $^1$H NMR. The desired compound is isolated as a colourless liquid; $^1$H-NMR (300 MHz, d$_6$-DMSO) δ(ppm)= 8.97 (s, 1H), 8.50 (dd, J$_1$=4.9 Hz, J$_2$=1.7 Hz, 1H), 8.12 (m, 1H), 7.31 (m, 1H), 7.19 (d, 7.9 Hz, 2H), 7.06 (d, 7.9 Hz, 2H), 3.62 (q, J=7.3 Hz, 2H), 2.40 (d, 7.1 Hz, 2H), 2.18 (m, 8H), 1.80 (sept, J=6.9, 1H), 1.41 (m, 16 H), 1.31 (s, J=7.2 Hz, 3H), 0.9 (t, J=7.2 Hz, 12 H), 0.85 (d, 6.6 Hz, 6H). $^{31}$P-NMR (121.5 MHz, d$_6$-DMSO) δ(ppm)=35.1. $^{13}$C-NMR (75 MHz, d$_6$-DMSO) δ(ppm)=175.7, 166.9, 150.5, 149.7, 139.5, 139.0, 136.2, 134.2, 128.7, 127.1, 122.6, 45.0, 44.2, 29.6, 23.3 (d, J=15.8 Hz), 22.6 (d, 4.8 Hz), 22.1, 18.9 17.3 (47.6 Hz), 13.2. $T_g$ −44° C., $T_{5\%onset}$ 201° C.

Example 19

Lidocaine Ibuprofenate-salicylic Acid
Lid[IbuSal]H-solvent-free Synthesis

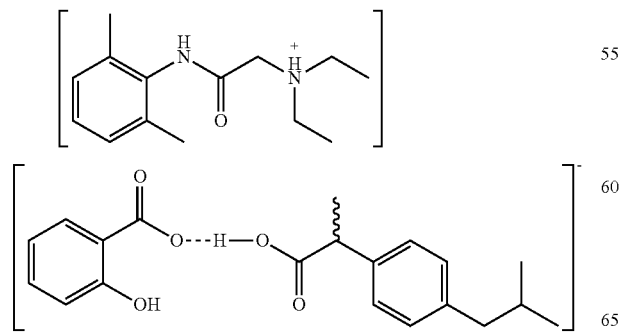

Ibuprofenic acid (206.28 mg, 1 mmol), salicylic acid (160.11 mg, 1 mmol) and lidocaine (234.34 mg, 1 mmol) were grinded in a mortar for 15 minutes until a clear viscose liquid was obtained. $^1$H-NMR (300 MHz, d$_6$-DMSO) δ(ppm) =9.91 (br s, 1H), 7.72 (dd, J$_1$=7.7 Hz, J$_2$=1.9 Hz, 1H), 7.25 (m, 1H), 7.19 (d, J=8.0 Hz, 2H), 7.10 (m, 5H), 6.71 (m, 2H), 3.63 (q, J=7.1 Hz, 1H), 3.06 (q, J=7.4 Hz, 4H), 2.41 (d, J=7.1 Hz, 2H), 2.17 (s, 6H), 1.80 (sept, J=6.8 Hz, 1H), 1.34 (d, J=7.2 Hz, 3H), 1.21 (t, J=7.2 Hz, 6H), 0.86 (d, J=7.2 Hz, 6H). $^{13}$C-NMR (75 MHz, d$_6$-DMSO) δ(ppm)=175.5, 171.9, 165.5, 162.2, 139.5, 138.5, 135.0, 134.2, 132.8, 130.1, 129.0, 127.8, 127.1, 126.8, 117.9, 117.1, 116.2, 53.9, 48.2, 44.3, 44.2, 29.6, 22.2, 18.5, 18.1, 10.0. $T_g$ −2° C., $T_{5\%onset}$ 153° C.

Example 18

Cetylpyridinium Salicylate-ibuprofenate
CetPySalIbuH

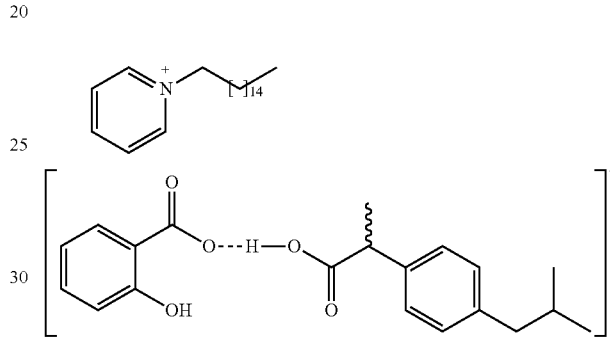

Cetylpyridinium salicylate (2 mmol) and ibuprofenic acid (2 mmol) were grinded for 15 minutes in a mortar until a colourless cream was obtained. Identity and purity of the obtained product was confirmed via $^1$H NMR. $^1$H-NMR (300 MHz, d$_6$-DMSO) δ(ppm)=9.12 (d, J=6.2 Hz, 2H), 8.60 (t, J=7.8 Hz, 1H), 8.12 (t, J=6.8 Hz, 2H), 7.66 (d, 7.6 Hz, 1H), 7.19 (d, J=7.6 Hz, 2H), 7.09 (m, 3H), 6.60 (m, 2H), 4.59 (t, J=7.6 Hz, 2H), 3.6 (q, J=6.9 Hz, 2H), 2.40 (d, J=7.6 Hz, 2H), 1.84 (m, 3H), 1.32 (d, J=7.6 Hz, 3H), 1.23 (s, 27H), 0.84 (m, 9H). $^{13}$C-NMR (75 MHz, d$_6$-DMSO) δ(ppm)=171.8, 163.4, 145.8, 145.2, 131.4, 130.2, 128.4, 121.1, 116.1, 160.0, 61.2, 31.7, 31.2, 29.4, 29.3, 29.2, 29.1, 28.8, 25.8, 22.5, 14.2. mp 16° C., $T_{5\%onset}$ 173° C.

Example 19

Cetylpyridinium Salicylate-cinnamate
CetPySalCinnH

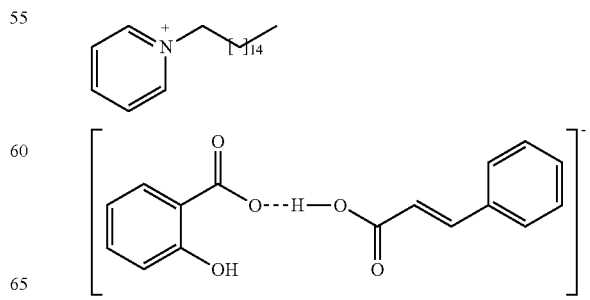

Cetylpyridinium salicylate (2 mmol) and ibuprofenic acid (2 mmol) were grinded for 15 minutes in a mortar until a colourless cream was obtained. Identity and purity of the obtained product was confirmed via ¹H NMR. ¹H-NMR (300 MHz, d₆-DMSO) δ(ppm)=9.14 (d, J=5.8 Hz, 2H), 8.60 (t, J=7.7 Hz, 1H), 8.16 (t, J=6.6 Hz, 2H), 7.64 (m, 3H), 7.56 (d, J=16.3 Hz, 1H), 7.39 (m, 3H), 7.13 (m, 1H), 6.60 (m, 2H), 6.56 (d, J=16.3 Hz, 1H), 4.60 (t, J=7.5 Hz, 2H), 1.88 (m, 2H), 1.20 (m, 27H), 0.84 (t, J=7.0 Hz, 3H). mp 15° C., $T_{5\%onset}$ 162° C.

Example 22

Cetylpyridinium Salicylate-clofibrate CetPySalClofib

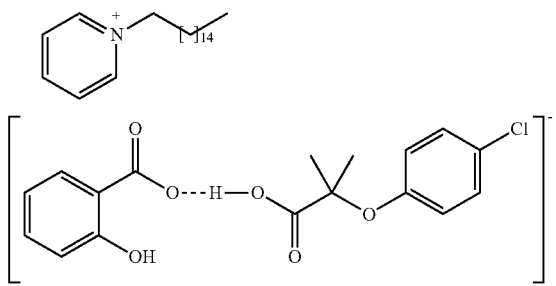

Cetylpyridinium salicylate (2 mmol) and clofibric acid (2 mmol) were grinded for 15 minutes in a mortar until a colourless cream was obtained. Identity and purity of the obtained product was confirmed via ¹H NMR. ¹H-NMR (300 MHz, d₆-DMSO) δ(ppm)=9.13 (d, J=6.3 Hz, 2H), 8.60 (t, J=7.7 Hz, 1H), 8.16 (t, J=7.0 Hz, 2H), 7.67 (d, 8.0 Hz, 1H), 7.28 (d, J=9.1 Hz, 2H), 7.14 (t, J=6.7 Hz, 1H), 6.84 ((d, J=9.1 Hz, 2H), 6.61 (m, 2H), 4.59 (t, J=7.5 Hz, 2H), 1.89 (m, 2H), 1.47 (s, 6H), 1.22 (s, 27H), 0.84 (t, J=7.0 Hz, 3H). mp 8° C., $T_{5\%onset}$ 197° C.

Example 23

Ephedrinium-lidocaine Salicylate H[EphLid]Sal

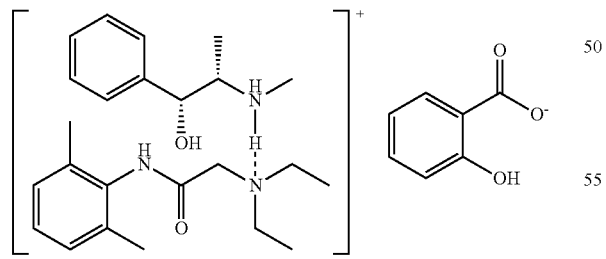

Lidocaine (468.67 mg, 2 mmol) and ephedrinium salicylate (606.72 mg, 2 mmol) were dissolved in 20 ml of acetone and stirred for 15 min at room temperature. The solvent was evaporated and the remaining viscous liquid was dried at 0.01 mbar with stirring for 24 hrs. The desired compound is isolated as a colourless viscous liquid. ¹H-NMR (300 MHz, d₆-DMSO) δ(ppm)=9.23 (br s, 1H), 7.72 (dd, J1=7.6 Hz, J2=1.8 Hz, 1H), 7.38 (m, 4H), 7.28 (m, 1H), 7.07 (s, 3H), 6.66 (m, 2H), 5.16 (d, J=2.4 Hz, 1H), 3.40 (m, 1H), 3.18 (s, 2H), 2.67 (s, 3H), 2.64 (q, J=7.3 Hz, 4H), 2.14 (s, 6H), 1.08 (t, J=7.2 Hz, 6H), 0.93 (d, J=6.8 Hz, 3H). $T_g$ -4° C.; $T_{5\%onset}$ 149. ° C.

Example 24

Ephedrinium-lidocaine Ibuprofenate H[EphLid]Ibu

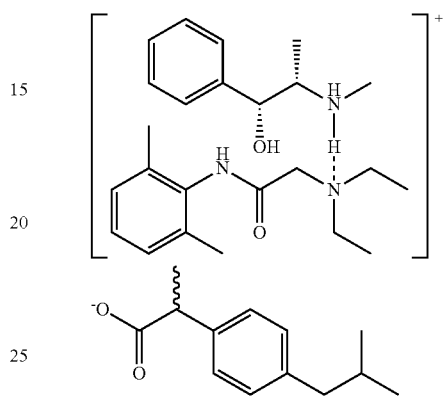

Lidocaine (468.67 mg, 2 mmol) and ephedrinium ibuprofenate (743.02 mg, 2 mmol) were dissolved in 20 ml of acetone and stirred for 15 min at room temperature. The solvent was evaporated and the remaining viscous liquid was dried at 0.01 mbar with stirring for 24 hrs and solidified after 1 week. The desired compound is isolated as a colourless solid. ¹H-NMR (300 MHz, d₆-DMSO) δ(ppm)=9.19 (br s, 1H), 7.32 (m, 5H), 7.20 (d, J=8.1 Hz, 2H), 7.09 (s, 3H), 7.05 (d, J=8.2 Hz, 2H), 5.03 (m, 1H), 3.50 (q, J=7.1 Hz, 1H), 3.13 (m, 3H), 2.62 (q, J=6.7 Hz, 4H), 2.45 (s, 3H), 2.40 (d, J=7.1 Hz, 2H), 2.15 (s, 6H), 1.79 (sept, J=6.7 Hz, 1H), 1.32 (d, J=7.0 Hz, 3H), 1.08 (t, J=7.0 Hz, 6H), 0.86 (m, 9H). mp 87° C., $T_{5\%onset}$ 134° C.

Example 25

Tramadolium-lidocaine Ibuprofenate H[TramLid]Ibu

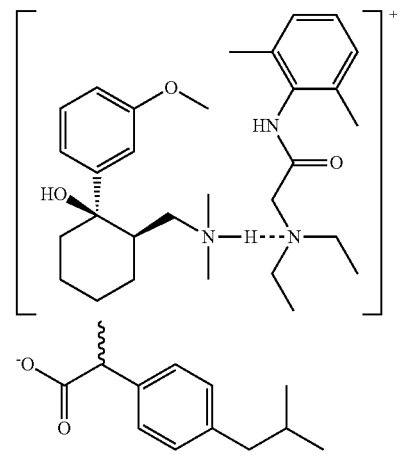

Lidocaine (270.13 mg, 1.15 mmol) and tramadolium ibuprofenate (541.4 mg, 1.153 mmol) were dissolved in 20 ml of acetone and stirred for 15 min at room temperature. The solvent was evaporated and the remaining viscous liquid was dried at 0.01 mbar with stirring for 24 hrs. The desired compound is isolated as a colourless liquid. $^1$H-NMR (300 MHz, d$_6$-DMSO) δ(ppm)=9.17 (br s, 1H), 7.19 (m, 3H), 7.06 (m, 7H), 6.73 (dd, J1=8.1 Hz, J2=2.3 Hz, 1H), 4.42 (br s, 2H), 3.74 (s, 3H), 3.61 (q, J=7.0 Hz, 1H), 3.13 (s, 2H), 2.61 (q, J=7.2 Hz, 4H), 2.50 (s, 2H), 2.41 (d, J=7.4 Hz, 2H), 2.13 (s, 7H), 1.94 (s, 6H), 1.89-1.41 (m, 8H), 1.33 (d, J=7.1 Hz, 3H), 1.07 (t, J=7.1 Hz, 6H), 0.86 (d, J=6.6 Hz, 6H). T$_g$–20° C., T$_{5\%onset}$ 154° C.

Example 26

Tramadolium-lidocaine Salicylate H[TramLid]Sal

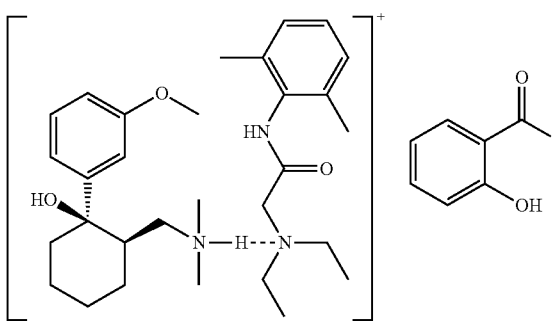

Lidocaine (5 mmol) and tramadolium salicylate (5 mmol) were dissolved in 20 ml of acetone and stirred for 15 min at room temperature. The solvent was evaporated and the remaining viscous liquid was dried at 0.01 mbar with stirring for 24 hrs and solidified after into a colourless solid. $^1$H-NMR (300 MHz, d$_6$-DMSO) δ(ppm)=10.32 (br s, 1H), 7.672 (dd, J=7.8 Hz, 1H), 7.26 (t, J=8.2 Hz, 1H), 7.15 (t, J=7.2 Hz, 1H), 7.06 (m, 5H), 6.79 (d, J=8.7 Hz, 1H), 6.62 (m, 2H), 3.76 (s, 3H), 3.39 (br s, OH), 2.69 (m, 4H), 2.51 (m, 6H), 2.14 (m, 9H), 1.61 (m, 7H), 1.09 (t, J=7.0 Hz, 6 H). $^{13}$C-NMR (75 MHz, d$_6$-DMSO) δ(ppm)=171.7, 162.2, 159.1, 150.2, 135.1, 135.0, 131.6, 130.0, 129.0, 127.6, 126.4, 119.9, 117.2, 116.2, 115.8, 111.4, 111.1, 73.9, 59.6, 56.2, 54.9, 48.1, 40.8, 40.2, 25.7, 24.6, 21.2, 18.1, 11.7. mp 64° C., T$_{5\%onset}$ 181° C.

Example 27

Promethazine-ephedrinium Docusate 1:1:1

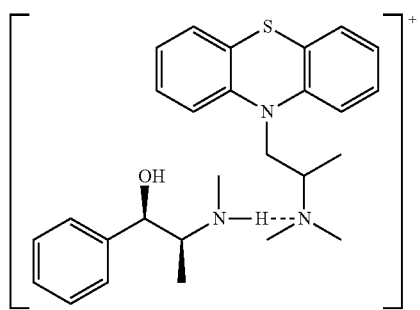

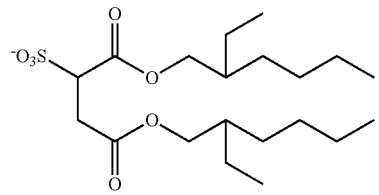

Promethazine (2 mmol) was added to ephedrinium docusate (2 mmol) and stirred for 15 minutes at 50° C. to obtain a light yellow viscous oil. Identity and purity were confirmed via $^1$H and $^{13}$C NMR. $^1$H-NMR (300 MHz, d$_6$-DMSO) δ(ppm)=7.39 (d, J=4.5 Hz, 3H), 7.29 (m, 1H), 7.19 (m, 4H), 7.08 (d, J=8.1 Hz, 2H), 6.95 (t, 7.4 Hz, 2H), 5.04 (d, J=2.7 Hz, 1H), 4.05 (dd, J1=13.81 Hz, J2=5.0 Hz, 1H), 3.89 (m, 4H), 3.68 (m, 2H), 3.35 (m, 1H), 2.87 (m, 3H), 12.63 (s, 3H), 2.24 (s, 6H), 1.49 (m, 2H), 1.23 (m, 16H), 0.84 (m, 18H). $^{13}$C-NMR (75 MHz, d$_6$-DMSO) δ(ppm)=171.0, 168.3, 145.1, 141.0, 128.1, 127.6, 1227.3, 127.2, 125.8, 124.4, 122.6, 116.2, 69.9, 66.2, 66.1, 61.5, 59.0, 55.6, 49.7, 40.6, 38.2, 38.2, 34.1, 30.8, 29.7, 29.6, 29.5, 28.3, 23.2, 23.0, 22.4, 13.9, 12.2, 10.8, 9.5. T$_g$–19° C., T$_{5\%onset}$ 164° C.

Example 28

Promethazine-ephedrinium Docusate 0.5:1:1

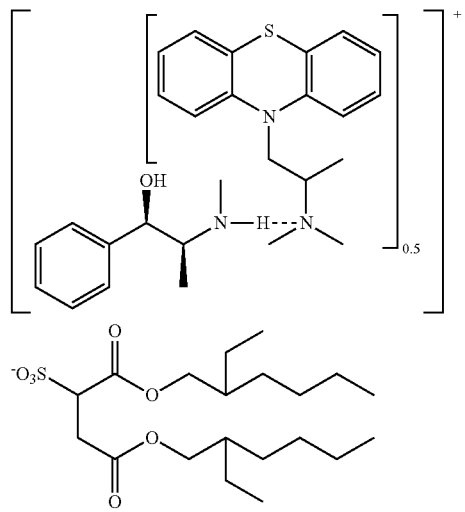

Promethazine (1 mmol) was added to ephedrinium docusate (2 mmol) and stirred for 15 minutes in acetone. The solvent was evaporated and remaining volatile material was removed under reduced pressure (0.01 mbar, 50° C.). $^1$H-NMR (300 MHz, d$_6$-DMSO) δ(ppm)=7.39 (d, J=4.5 Hz), 7.29 (m), 7.19 (m), 7.08 (d, J=8.1 Hz), 6.95 (t, 7.4 Hz), 5.04 (d, J=2.7 Hz), 4.05 (dd, J$_1$=13.81 Hz, J$_2$=5.0 Hz), 3.89 (m, 4H), 3.68 (m), 3.35 (m), 2.87 (m), 12.63 (s), 2.24 (s), 1.49 (m, 2H), 1.23 (m, 16H), 0.84 (m, 18H). $^{13}$C-NMR (75 MHz, d$_6$-DMSO) δ(ppm)=171.0, 168.3, 145.1, 141.0, 128.1, 127.6, 1227.3, 127.2, 125.8, 124.4, 122.6, 116.2, 69.9, 66.2, 66.1, 61.5, 59.0, 55.6, 49.7, 40.6, 38.2, 38.2, 34.1, 30.8, 29.7, 29.6, 29.5, 28.3, 23.2, 23.0, 22.4, 13.9, 12.2, 10.8, 9.5.

Example 29

Promethazine-ephedrinium Salicylate

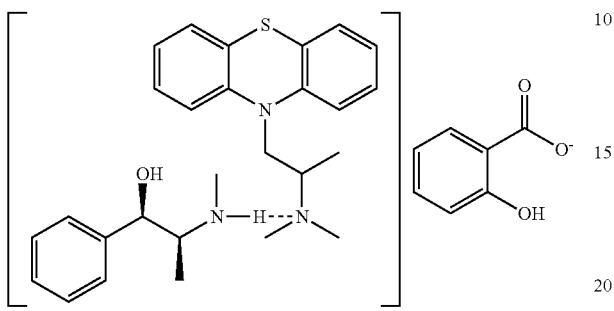

Promethazine (2 mmol) and ephedrinium salicylate (2 mmol) were dissolved in 25 ml of acetone and stirred for 15 min at room temperature, the solvent was evaporated and remaining volatile material was removed under vacuum (0.01 mbar, 50° C.) to yield the product as colourless viscous glass. $^1$H-NMR (300 MHz, d$_6$-DMSO) δ(ppm)=7.72 (dd, J$_1$=7.7 Hz, J$_2$=1.8 Hz, 1H), 7.42-7.15 (m, 10H), 7.0 (m, 1H), 7.01 (d, J=7.9 Hz, 1H), 6.96 (t, J=7.2 Hz, 2H), 6.65 (m, 2H), 5.13 (d, J=2.5 Hz, 1H), 4.10 (dd, J$_1$=14.0 Hz, J$_2$=5.0 Hz, 1H), 3.72 (dd, J$_1$=14.2 Hz, J$_2$=8.6 Hz), 3.37 (m, 1H), 3.01 (m, 1H), 2.65 (s, 3H), 2.2.9 (s, 6H), 0.99 (d, J=6.6 Hz, 3H), 0.92 (d, 6.8 Hz, 3H). T$_g$ 14° C., T$_{5\%onset}$ 151° C.

Ionic Liquid Prodrugs

Example 30

Synthesis of 4-Acetamidophenyl 2-chloroacetate [2]

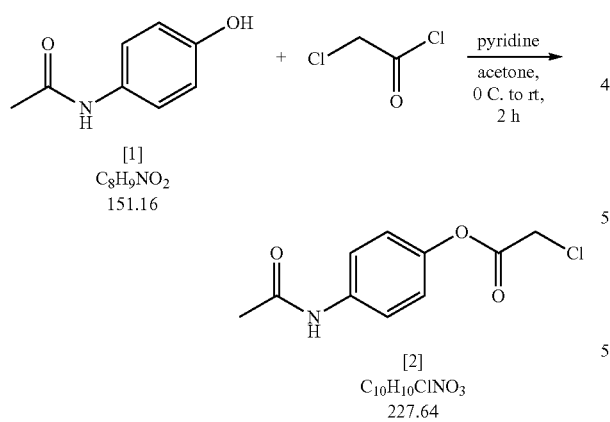

Paracetamol [1] (15.117 g, 50 mmol) and pyridine (7.910 g, 50 mmol) were suspended in anhydrous acetone (200 ml) and chilled to 0° C. under an atmosphere of dry nitrogen. Chloroacetylchloride (11.29 g, 50 mmol) was added dropwise (violent reaction) and the resulting solution was stirred for additional 2 hours at room temperature. Water (300 ml) was added and the mixture was heated until a clear solution was obtained. The product [2] precipitated upon cooling and was collected via filtration, washed with water and dried under reduced pressure (0.01 mbar, 50° C.) to yield [2] as colourless needles in 72% yield. The product was pure according to $^1$H NMR and directly subjected to the next step without further purification.

$^1$H-NMR (300 MHz, d$_6$-DMSO) δ(ppm)=10.05 (s, 1H), 7.62 (d, J=9.01 Hz, 2H), 7.10 (d, J=9.01 Hz, 2H), 4.67 (s, 2H), 3.38 (s, 3H), 2.05 (s, 3H). $^{13}$C-NMR (75 MHz, d$_6$-DMSO) δ(ppm)=168.7, 166.9, 145.6, 137.2, 122.0, 120.3, 41.6, 24.3. mp 186° C.

Example 31

Synthesis of 1-(2-(4-acetamidophenoxy)-2-oxoethyl)-3-methyl-1H-imidazol-3-ium Chloride [3]

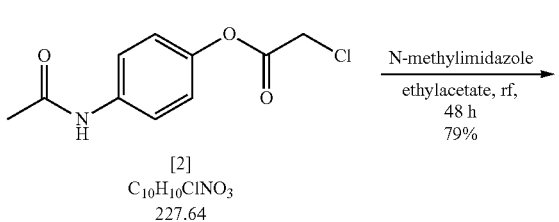

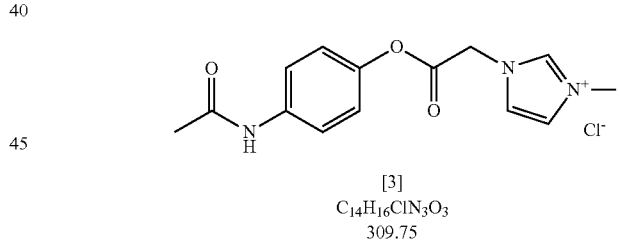

4-Acetamidophenyl 2-chloroacetate [2] (1.138 g, 5 mmol) and N-methylimidazol (0.492 g, 6 mmol) were suspended in 50 ml of anhydrous ethyl acetate and refluxed for 48 hrs. After cooling to room temperature the white precipitate was filtered, washed with ethylacetate and diethylether and dried under reduced pressure to give [3] in 79% yield. The product was pure according to $^1$H NMR and was directly subjected to the next step without further purification.

The desired compound is isolated as a colourless powder. $^1$H-NMR (300 MHz, d$_6$-DMSO) δ(ppm)=10.08 (s, 1H), 9.28 (s, 1H), 7.86 (s, 1H), 7.78 (s, 114), 7.68 (d, J=9.01 Hz, 2H), 7.13 (d, J=9.01 Hz, 2H), 5.57 (s, 2H), 3.93 (s, 3H), 2.05 (s, 3H). $^{13}$C-NMR (75 MHz, d$_6$-DMSO) δ(ppm)=168.4, 166.1, 144.9, 137.9, 137.7, 123.8, 123.5, 121.4, 119.9, 49.7, 36.0, 23.9.

mp 206° C. (dec), T$_{5\%onset}$ 200° C.

Example 32

1-(2-(4-acetamidophenoxy)-2-oxoethyl)-1-methylpyrrolidinium Chloride [4]

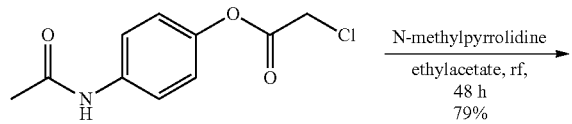

[2]
C₁₀H₁₀ClNO₃
227.64

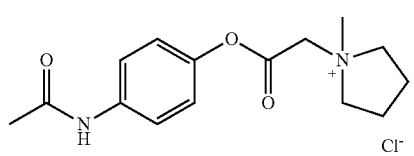

[4]
C₁₅H₂₁ClN₂O₃
312.79

4-Acetamidophenyl 2-chloroacetate [2] (1.138 g, 5 mmol) and N-methylpyrrolidine (0.511 g, 6 mmol) were suspended in 50 ml of anhydrous ethyl acetate and refluxed for 48 hrs. After cooling to room temperature the white precipitate was filtered, washed with ethylacetate and diethylether and dried under reduced pressure to give [4] in 97% yield. The product was pure according to $^1$H NMR and was directly subjected to the next step without further purification. The desired compound is isolated as a colourless powder. $^1$H-NMR (300 MHz, $d_6$-DMSO) δ(ppm)=10.48 (s, 1H), 7.72 (d, J=8.90 Hz, 2H), 7.17 (d, J=8.90 Hz, 2H), 4.91 (s, 2H), 3.75 (m, 4H), 3.26 (s, 3H), 2.13 (m, 4H), 2.06 (s, 3H). $^{13}$C-NMR (75 MHz, $d_6$-DMSO) δ(ppm)=168.8, 164.8, 144.4, 138.2, 121.9, 120.2, 65.5, 62.0, 49.7, 24.3, 21.7. mp 186° C. (dec), $T_{5\%onset}$ 197° C.

Example 33

1-(2-(4-acetamidophenoxy)-2-oxoethyl)pyridinium Chloride [5]

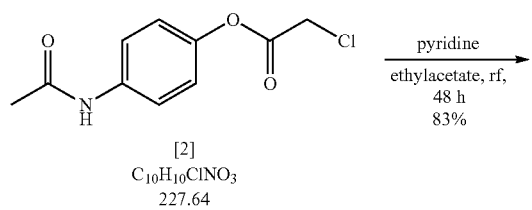

[2]
C₁₀H₁₀ClNO₃
227.64

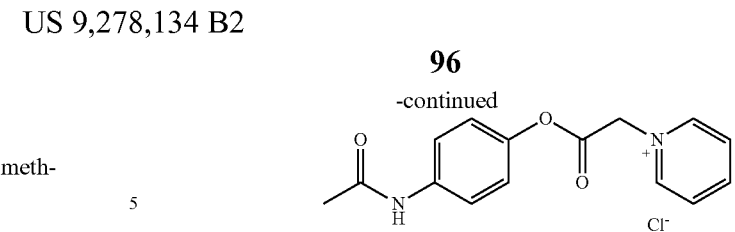

[5]
C₁₅H₁₅ClN₂O₃
306.74

4-Acetamidophenyl 2-chloroacetate [2] (1.138 g, 5 mmol) and pyridine (0.475 g, 6 mmol) were suspended in 50 ml of anhydrous ethyl acetate and refluxed for 48 hrs. After cooling to room temperature the white precipitate was filtered, washed with ethylacetate and diethylether and dried under reduced pressure to give [5] in 97% yield. The product was pure according to $^1$H NMR and was directly subjected to the next step without further purification. The desired compound is isolated as a colourless powder. $^1$H-NMR (300 MHz, $d_6$-DMSO) δ(ppm)=10.31 (s, 1H), 9.27 (d, J=6.5 Hz, 2H), 8.76 (t, 7.9 Hz, 1H), 8.29 (t, 7.2 Hz, 2H), 7.71 (d, J=9.7 Hz, 2H), 7.11 (d, J=9.7 Hz, 2H), 4.69 (s, 2H), 2.08 (s, 3H). mp 199° C. (dec), $T_{5\%onset}$ 198° C.

Example 34

(2-(4-acetamidophenoxy)-2-oxoethyl)tributylphosphonium Chloride [6]

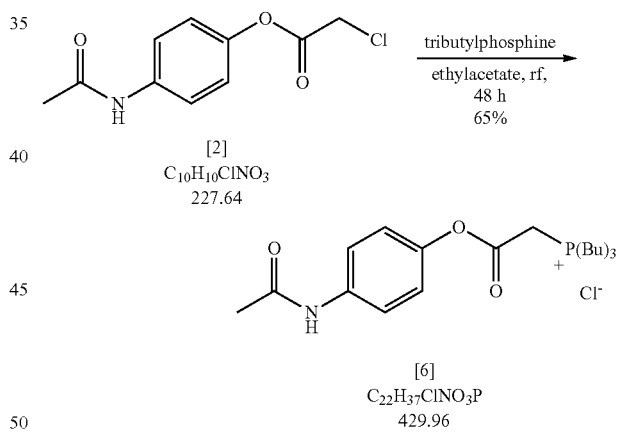

[2]
C₁₀H₁₀ClNO₃
227.64

[6]
C₂₂H₃₇ClNO₃P
429.96

4-Acetamidophenyl 2-chloroacetate [2] (1.138 g, 5 mmol) and tributylphosphine (0.475 g, 6 mmol) were suspended in 50 ml of anhydrous ethyl acetate and refluxed for 48 hrs. After cooling to room temperature the white precipitate was filtered, washed with ethylacetate and diethylether and dried under reduced pressure to give [6]. The crude product was crystallized twice from acetonitrile to give pure [6] in 65% yield. Identity and purity was confirmed via $^1$H and $^{13}$C NMR. The desired compound is isolated as colourless needles. $^1$H-NMR (300 MHz, $d_6$-DMSO) δ(ppm)=10.49 (s, 1H), 7.71 (d, J=8.95 Hz, 2H), 7.12 (d, J=8.95 Hz, 2H), 4.18 (d, J=14.33, 2H), 2.41 (m, 3H), 2.06 (s, 3H), 1.55 (m, 6H), 1.41 (m, 6H), 0.91 (t, J=7.17). $^{31}$P-NMR (121.5 MHz, $d_6$-DMSO) δ(ppm)=34.8. $^{13}$C-NMR (75 MHz, $d_6$-DMSO) δ(ppm)= 168.4, 164.7, 144.8, 137.8, 121.4, 119.9, 25.8 (d, J=47.9

Hz), 23.9, 23.3 (d, J=16.77 Hz), 22.6 (d, J=4.43 Hz), 18.2 (d, J=47.7 Hz), 13.2. mp 199° C. (dec), T$_{5\%onset}$ 197° C.

Example 35

Synthesis of 1-(2-(4-acetamidophenoxy)-2-oxoethyl)-3-methyl-1H-imidazol-3-ium Docusate [7]

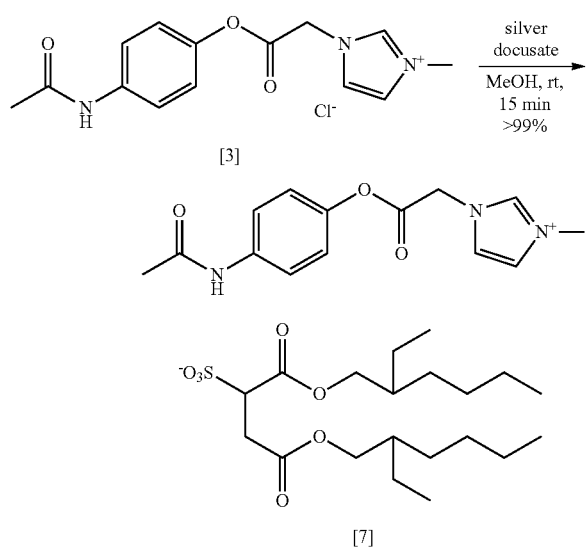

Chloride [3] (309.1 mg, 1 mmol) and silver docusate (529.4 mg, 1 mmol) were suspended in 50 ml of anhydrous methanol and stirred in the dark at room temperature for 15 min. The suspension was filtered over celite and the filtrate was evaporated <40° C. Remaining volatile material was removed under reduced pressure (0.01 mbar, 40° C.) to yield product [7] in quantitative yield. The desired compound is isolated as a yellow oil. $^1$H-NMR (300 MHz, d$_6$-DMSO) δ(ppm)=10.07 (s, 1H), 9.16 (s, 1H), 7.82 (s, 1H), 7.77(s, 1H), 7.64 (d, J=9.2 Hz, 2H), 7.14 (d, J=9.2 Hz, 2H), 5.51 (s, 2H), 3.93 (s, 3H), 3.88 (m, 4H), 3.65 (dd, J$_1$=11.5 Hz, J$_2$=3.8 Hz, 1H), 2.85 (m, 2H), 2.04 (s, 3H), 1.49 (m, 2H), 1.23 (m, 16 H), 0.86 (m, 12H). $^{13}$C-NMR (75 MHz, d$_6$-DMSO) δ(ppm)= 171.0, 168.4, 166.0, 144.9, 137.8, 137.5, 123.8, 123.5, 121.5, 119.9, 66.1, 61.5, 49.7, 38.1, 36.0, 34.1, 29.7, 29.6, 28.3, 23.9, 23.2, 22.4, 13.9, 10.8, 10.7. T$_{5\%onset}$ 21'7° C.

Example 36

1-(2-(4-acetamidophenoxy)-2-oxoethyl)-1-methylpyrrolidinium Docusate [8]

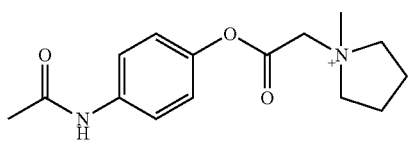

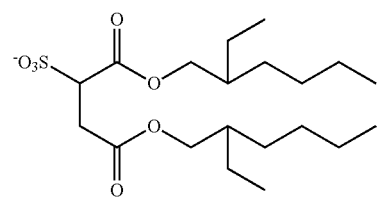

Prepared according to example 35 in quantitative yield. The desired compound is isolated as a yellow oil. $^1$H-NMR (300 MHz, d$_6$-DMSO) δ(ppm)=10.011 (s, 1H), 7.66 (d, J=8.7 Hz, 2H), 7.17 (d, J=8.7 Hz, 2H), 4.82 (s, 2H), 3.88 (m, 2H), 3.72 (m, 5H), 3.25 (s, 3H), 2.88 (m, 2H), 2.14 (m, 4H), 2.05 (s, 3H), 1.47 (m, 2H), 1.23 (m, 16H), 0.82 (m, 12H). $^{13}$C-NMR (75 MHz, d$_6$-DMSO) δ(ppm)=168.4, 166.1, 144.9, 137.9, 137.7, 123.8, 123.5, 121.4, 119.9, 49.7, 36.0, 23.9. $^{13}$C-NMR (75 MHz, d$_6$-DMSO) δ(ppm)=171.0, 168.4, 164.4, 144.5, 137.7, 121.6, 119.8, 66.1, 65.1, 61.6, 49.4, 38.1, 34.1, 29.7, 29.6, 28.3, 23.9, 23.2, 23.0, 22.4, 21.4, 13.8, 10.7. T$_{5\%onset}$ 233° C.

Example 37

1-(2-(4-acetamidophenoxy)-2-oxoethyl)pyridinium Docusate [9]

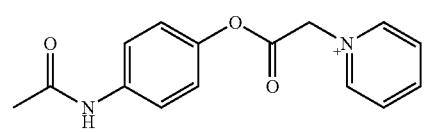

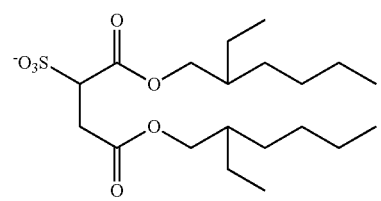

Prepared according to example 35 in quantitative yield. The desired compound is isolated as a yellow glass. $^1$H-NMR (300 MHz, d$_6$-DMSO) δ(ppm)=10.13 (s, 1H), 9.21 (d, J=6.2 Hz, 2H), 8.82 (t, 7.8 Hz, 1H), 8.36 (t, 7.2 Hz, 2H), 7.72 (d, J=9.0 Hz, 2H), 7.25 (d, J=9.0 Hz, 2H), 6.00 (s, 2H), 3.96 (m, 4H), 3.71 (dd, J$_1$=11.3 Hz, J$_2$=3.7 Hz, 1H), 2.94 (m, 2H), 2.12 (s, 3H), 1.56 (m, 2H), 1.00 (m, 16 H), 0.93 (m, 12H). $^{13}$C-NMR (75 MHz, d$_6$-DMSO) δ(ppm)=71.0, 168.4, 165.6, 147.0, 146.5, 144.9, 137.6, 127.9, 121.5, 119.9, 66.2, 66.1, 61.5, 60.4, 38.1, 34.1, 29.7, 29.6, 28.3, 23.2, 23.1, 23.0, 22.4, 13.9, 10.8, 10.7. $T_g$ 25° C., $T_{5\%onset}$ 238° C.

Example 38

(2-(4-acetamidophenoxy)-2-oxoethyl)tributylphosphonium Docusate [10]

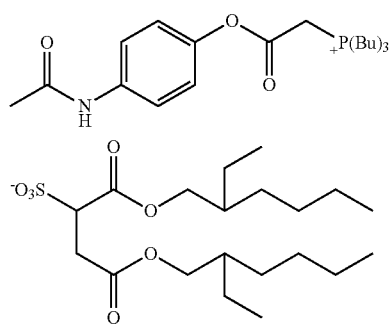

Prepared according to example 35 in quantitative yield. The desired compound is isolated as a yellow oil. $^1$H-NMR (300 MHz, d$_6$-DMSO) δ(ppm)=10.07 (s, 1H), 7.64 (s, 2H), 7.14 (s, 2H), 4.07 (d, J=14.6 Hz, 2H), 3.88 (s, 4H), 3.62 (s, 1H), 2.84 (m, 2H), 2.36 (s, 6H), 2.04 (s, 3H), 1.49 (m, 14 H), 1.23 (m, 16H), 0.89 (m, 21 H). $^{13}$C-NMR (75 MHz, d$_6$-DMSO) δ(ppm)=168.4, 166.1, 144.9, 137.9, 137.7, 123.8, 123.5, 121.4, 119.9, 49.7, 36.0, 23.9. $T_g$ –17° C., $T_{5\%onset}$ 227° C.

Example 39

Synthesis of 1-(2-(4-acetamidophenoxy)-2-oxoethyl)-3-methyl-1H-imidazol-3-ium Lactate [11]

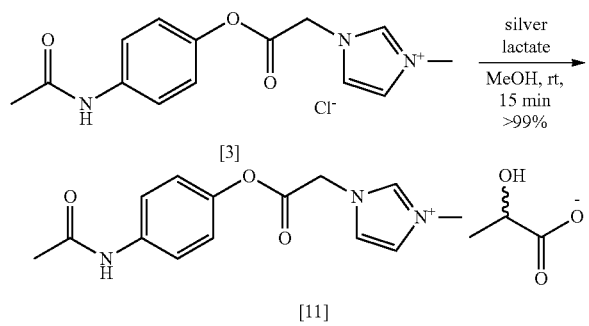

Chloride [3] (309.1 mg, 1 mmol) and racemic silver lactate (196.4 mg, 1 mmol) were suspended in 25 ml of anhydrous methanol and stirred in the dark at room temperature for 15 min. The suspension was filtered over celite and the filtrate was evaporated at <40° C. Remaining volatile material was removed under reduced pressure (0.01 mbar, 40° C.) to yield product [11] as yellow oil in quantitative yield. $^1$H-NMR (300 MHz, d$_6$-DMSO) δ(ppm)=9.85 (s, 1H), 9.18 (s, 1H), 7.75 (s, 2H), 7.32 (d, J=8.1 Hz, 2H), 6.68 (d, J=8.1 Hz, 2H), 5.29 (s, 2H), 3.90 (s, 3H), 3.57 (q, J=6.8 Hz, 1H), 1.98 (s, 3H), 1.11 (d, J=6.6 Hz, 3H).

Example 40

1-(2-(4-acetamidophenoxy)-2-oxoethyl)-1-methylpyrrolidinium Lactate [12]

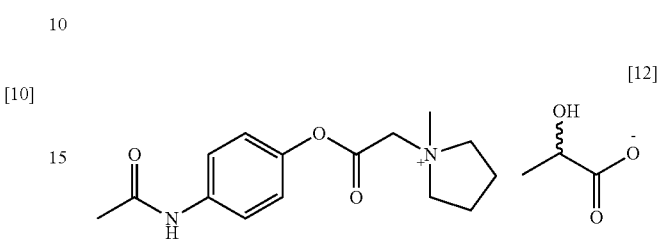

Prepared according to example 39 in quantitative yield. Identity and purity were confirmed via $^1$H and $^{13}$C NMR. The desired compound is isolated as a yellow oil.

$^1$H-NMR (300 MHz, d$_6$-DMSO) δ(ppm)=9.82 (s, 1H), 7.33 (d, J=8.8 Hz, 2H), 6.69 (d, J=88 Hz, 2H), 4.55 (s, 2H), 3.76 (s, 3H), 3.66 (m, 4H), 3.54 (q, J=6.7 Hz, 1H), 2.09 (m, 4H), 1.97 (s, 3H), 1.09 (d, J=6.8 Hz, 3H). $T_{5\%onset}$ 166° C.

Example 41

Prodrug Hydrolysis—General Procedure

Acetaminophen prodrug (0.5 mmol) was dissolved in 5 ml phosphate buffer pH 7.4. The resulting 0.1 M solutions were stirred in a preheated oil bath at 37° C. Sample of 0.05 ml were withdrawn at intervals, diluted with D$_2$O to 0.5 ml and $^1$H NMR spectra was immediately measured. Decomposition could be monitored via integration of representing aromatic signals of prodrug and of free acetaminophen.

Ionic Liquid Immobilized Fragrances

Example 42

Synthesis of (E)-3,7-dimethylocta-2,6-dienyl 2-chloroacetate [2]

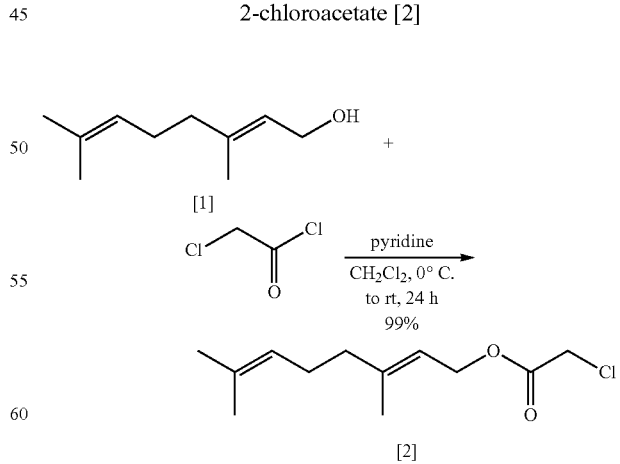

Geraniol [1] (7.711 g, 50 mmol) and pyridine (3.955 g, 50 mmol) were suspended in anhydrous dichloromethane (200 ml) and chilled to 0° C. under an atmosphere of dry nitrogen. Chloroacetylchloride (5.647 g, 50 mmol) was added dropwise (violent reaction) and the resulting solution was stirred for 24 hrs at room temperature. Water (100 ml) was added, the organic layer was separated and the aqueous layer extracted with dichloromethane. The combined organic layers were successively washed with 2N HCl, saturated NaHCO$_3$ solution and brine, dried over MgSO$_4$ and the solvent was evaporated. Remaining volatile material was removed under reduced pressure (0.01 mbar) to yield product [2] as yellow liquid. The product was pure according to $^1$H NMR and directly subjected to the next step without further purification.

$^1$H-NMR (300 MHz, d$_6$-DMSO) δ(ppm)=5.31 (t, J=7.4 Hz, 1H), 5.06 (m, 1H), 4.64 (d, J=7.4 Hz, 2H), 4.38 (s, 2H), 2.03 (m, 4H), 1.68 (s, 3H), 1.64 (s, 3H), 1.56 (s, 3H). $^{13}$C-NMR (75 MHz, d$_6$-DMSO) δ(ppm)=167.3, 142.4, 131.1, 123.7, 117.8, 62.2, 41.1, 38.9, 25.7, 25.4, 17.5, 16.2.

Example 43

Synthesis of (E)-1-(2-(3,7-dimethylocta-2,6-dienyloxy)-2-oxoethyl)-3-methyl-1H-imidazol-3-ium Chloride [3]

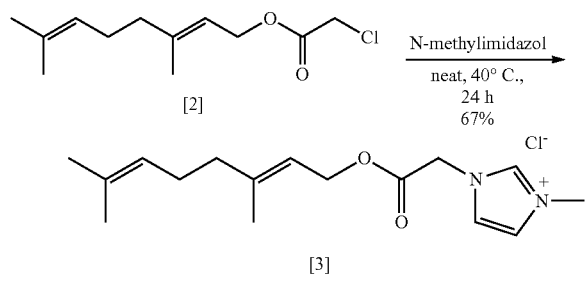

Geraniol ester [2] (2.307 g, 10 mmol) and N-methylimidazole (0.821 g, 10 mmol) were mixed in and stirred in a sealed vessel at 40° C. for 24 hrs. A light-brown solid was formed and suspended in anhydrous diethylether. The solid precipitate was filtered, washed with diethylether and dried under reduced pressure (0.01 mbar) to give imidazolium chloride [3] in 67% yield as light-yellow hygroscopic solid. The product was pure according to $^1$H NMR and directly subjected to the next step without further purification. $^1$H-NMR (300 MHz, d$_6$-DMSO) δ(ppm)=9.36 (s, 1H), 7.82 (s, 2H), 5.37 (s, 2H), 5.33 (t, J=7.0 Hz, 1H), 5.07 (s, 1H), 4.68 (d, J=7.1 Hz, 2H), 3.93 (s, 3H), 2.03 (m, 4H), 1.66 (s, 3H), 1.64 (s, 3H), 1.56 (s, 3H). $^{13}$C-NMR (75 MHz, d$_6$-DMSO) δ(ppm)=166.9, 142.6, 137.8, 131.1, 123.7, 123.6, 123.3, 117.8, 62.4, 49.4, 35.9, 25.8, 25.5, 17.6, 16.1. mp 160° C. (dec), T$_{5\%onset}$ 125° C.

Example 44

Synthesis of (E)-1-(2-(3,7-dimethylocta-2,6-dienyloxy)-2-oxoethyl)-3-methyl-1H-imidazol-3-ium Docusate [4]

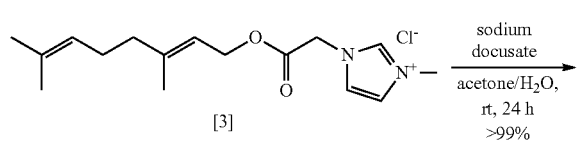

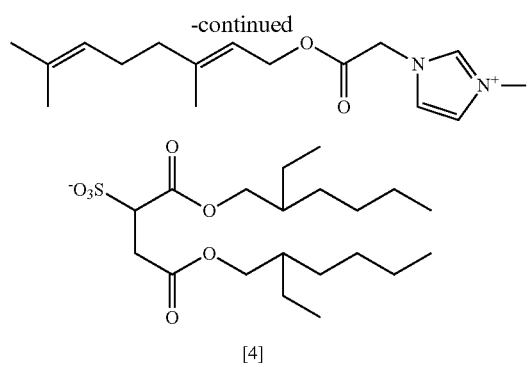

Imidazolium chloride [3] (312.8 mg, 1 mmol) and sodium docusate (444.6 mg, 1 mmol) were dissolved in 20 ml of acetone/H$_2$O 1:1 and stirred overnight at room temperature. The remaining suspension was diluted with 50 ml of H$_2$O and extracted with dichloromethane. The organic layer was washed successively with water until no more chloride ions could be detected in the washings (checked by addition of AgNO$_3$ solution), dried over MgSO$_4$ and the solvent was evaporated. Remaining volatile material was removed under reduced pressure (0.01 mbar) to give imidazolium docusate [4] in quantitative yield as yellow oil. $^1$H-NMR (300 MHz, d$_6$-DMSO) δ(ppm)=9.07 (s, 1H), 7.71 (s, 2H), 5.33 (t, J=7.3 Hz, 1H), 5.24 (s, 2H), 5.07 (m, 1H), 4.69 (d, J=7.3 Hz, 2H), 3.91 (s, 3H), 3.90 (m, 4H), 3.62 (dd, J$_1$=11.39 Hz, J$_2$=3.88 Hz, 1H), 2.86 (m, 2H), 2.04 (m, 4H), 1.68 (s, 3H), 1.65 (s, 3H), 1.57 (s, 3H), 1.49 (m, 2H), 1.24 (m, 16 H), 0.84 (m, 12H). $^{13}$C-NMR (75 MHz, d$_6$-DMSO) δ(ppm)=171.1, 168.1, 166.9, 142.7, 137.7, 131.2, 123.7, 123.6, 123.4, 117.6, 66.2, 66.1, 62.4, 61.4, 49.5, 38.1, 356.0, 34.1, 29.8, 29.6, 28.3, 25.8, 25.5, 23.2, 23.0, 22.4, 17.6, 16.2, 13.9, 10.8. T$_{5\%onset}$ 170° C.

Thermocleavage of the immobilized fragrance Geraniol [4] was demonstrated with TGA (FIG. 6). Mass loss of the first decomposition step obtained corresponds to mass percentage of Geraniol [1] in the prodrug [4].

Example 45

Synthesis of (E)-4-(3,7-dimethylocta-2,6-dienyloxy)-4-oxobutanoic Acid [5]

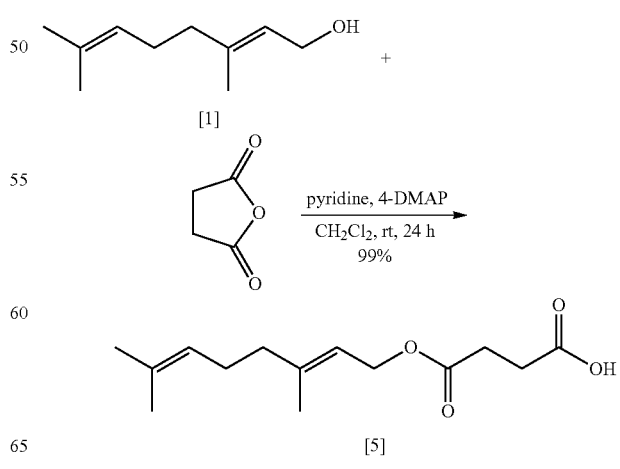

Geraniol [1] (1.542 g, 10 mmol), succinic anhydride (1.201 g, 12 mmol) and 4-DMAP (10 mg, cat) were suspended in anhydrous dichloromethane (50 ml) under an atmosphere of dry nitrogen. Pyridine (0.791 g, 10 mmol) was added and the reaction mixture was stirred for 24 hrs at room temperature. The reaction mixture was successively washed with 2N HCl and $H_2O$, dried over $Na_2SO_4$ and the solvent was evaporated. Remaining volatile material was removed under reduced pressure (0.01 mbar) to yield product [2] as yellow liquid in 99% yield. The product was pure according to $^1H$ NMR and directly subjected to the next step without further purification. $^1$H-NMR (300 MHz, $d_6$-DMSO) δ(ppm)=12.24 (br s, 1H), 5.29 (t, J=7.0 Hz, 1H), 5.08 (t, 6.7, 1H), 4.55 (d, J=7.1 Hz, 2H), 2.49 (m, 2H), 2.03 (m, 4H), 1.67 (s, 3H), 1.66 (s, 3H), 1.59 (s, 3H). $^{13}$C-NMR (75 MHz, $d_6$-DMSO) δ(ppm)=173.3, 172.2, 141.2, 131.1, 123.7, 118.5, 60.7, 38.9, 28.7, 28.6, 25.8, 25.5, 17.5, 16.1.

Example 46

Synthesis of 2-Hydroxy-N,N,N-trimethylethanaminium (E)-4-(3,7-dimethylocta-2,6-dienyloxy)-4-oxobutanoate [6]

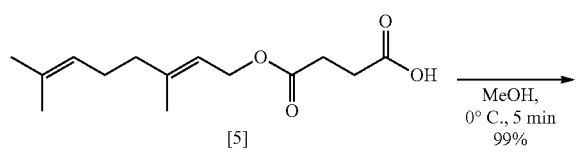

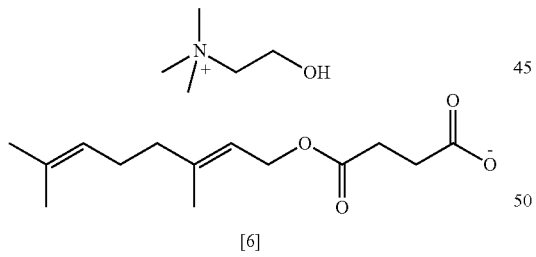

Hemisuccinate [5] (1.0173 g, 4 mmol) was dissolved in 10 ml of methanol and chilled to 0° C. Choline hydroxide in (1.13 ml, 40% sol. in methanol, 4 mmol) was added dropwise and the reaction mixture was stirred for 5 min at 0° C. The solvent was evaporated and remaining volatile material was removed under reduced pressure (0.01 mbar) to yield product [6] as yellow liquid in quantitative yield. The product was pure according to $^1H$ NMR without further purification. $^1$H-NMR (300 MHz, $d_6$-DMSO) δ(ppm)=5.28 (t, J=7.0 Hz, 1H), 5.07 (t, J=6.8 Hz, 1H), 4.49 (d, J=7.0 Hz, 2H), 3.85 (m, 2H), 3.44 (m, 2H), 3.13 (s, 9H), 2.36 (t, J=7.2 Hz, 2H), 2.10 (t, J=7.2 Hz, 2H), 2.03 (m, 4H, 1.65 (s, 6H), 1.57 (s, 3H). $^{13}$C-NMR (75 MHz, $d_6$-DMSO) δ(ppm)=174.0, 173.6, 140.7, 131.1, 123.8, 119.0, 67.3, 60.2, 55.0, 53.1, 39.3, 32.8, 31.2, 25.8, 25.5, 17.6, 16.2. $T_g$ –65° C., $T_{5\%onset}$ 170° C.

New API ILs

Example 47

Tramadolium Salicylate [1]

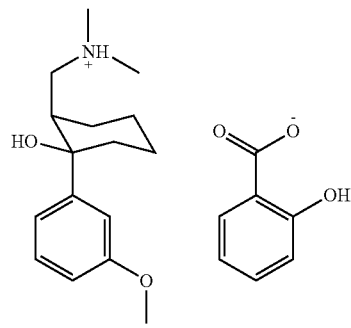

Tramadolium hydrochloride (1.499 g, 5 mmol) and sodium salicylate (0.801 g, 5 mmol) were dissolved in 50 ml of acetone/$H_2O$ 1:1 and stirred overnight at room temperature. The obtained suspension was chilled to 0° C., the precipitate was collected via filtration, washed with $H_2O$ and dried under reduced pressure (0.01 mbar) to isolate tramadolium salicylate as colourless solid in 79% yield. $^1$H-NMR (300 MHz, $d_6$-DMSO) δ(ppm)=7.69 (dd, $J_1$=7.6 Hz, $J_2$=1.8 Hz, 1H), 7.27 (t, J=8.1 Hz, 1H), 7.19 (m, 1H), 7.08 (m, 2H), 6.79 (m, 1H), 6.66 (m, 2H), 3.76 (s, 3H), 3.56 (br s, 1H), 2.83 (t, J=11.9 Hz, 1H), 2.52 (s, 6H), 2.33 (d, 13.0 Hz, 1H), 2.24 (m, 1H), 1.89 (m, 1H), 1.64 (m, 7H). $^{13}$C-NMR (75 MHz, $d_6$-DMSO) δ(ppm)=172.0, 262.3, 159.2, 150.0, 131.9, 120.1, 129.1, 119.5, 117.2, 116.5, 117.2, 116.5, 115.9, 111.5, 111.1, 73.9, 59.4, 55.0, 43.0, 40.5, 40.4, 25.7, 24.6, 21.2. mp 183° C., $T_{5\%onset}$ 220° C.

Example 48

Tramadolium rac-ibuprofenate 121

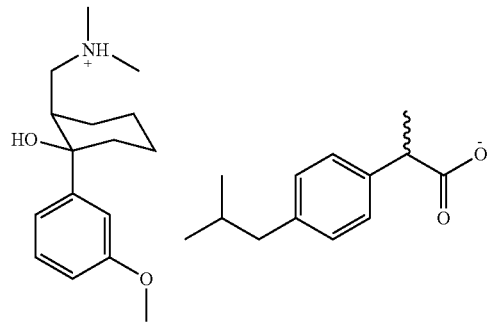

Tramdolium hydrochloride (1.499 g, 5 mmol) and racemic sodium ibuprofenate (1.1441 g, 5 mmol) were dissolved in 50 ml of acetone/$H_2O$ 1:1 and stirred overnight at room temperature. The remaining suspension was diluted with 50 ml of H₂O and extracted with dichloromethane. The organic layer was washed successively with water until no more chloride ions could be detected in the washings (checked by addition of AgNO₃ solution), dried over MgSO₄ and the solvent was evaporated. Remaining volatile material was removed under reduced pressure (0.01 mbar) to give tramadolium rac-ibuprofenate [2] in 89% yield as viscous glass that solidified after 2 weeks. ¹H-NMR (300 MHz, d₆-DMSO) δ(ppm)=7.19 (m, 3H), 7.08 (m, 2H), 7.00 (m, 2H), 6.72 (dd, J₁=8.1, J₂=2.3 Hz, 1H)), 3.73 (s, 3H), 3.58 (q, J=7.0 Hz, 1H), 2.40 (d, J=7.0 Hz, 2H), 2.11 (m, 1H), 1.91 (s, 6H), 1.85-1.35 (m, 9H), 1.31 (d, J=7.1 Hz, 3H), 0.85 (d, J=7.7 Hz, 6H) ppm. mp 75° C., $T_{5\%onset}$ 175° C.

Example 49

Tramadolium (S)-ibuprofenate [3]

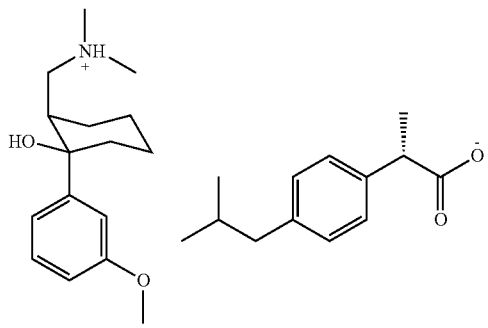

[3]

Prepared according to example 48 in 76% yield. ¹H-NMR (300 MHz, d₆-DMSO) δ(ppm)=7.19 (m, 3H), 7.08 (m, 2H), 7.00 (m, 2H), 6.72 (dd, J₁=8.1, J₂=2.3 Hz, 1H)), 3.73 (s, 3H), 3.58 (q, J=7.0 Hz, 1H), 2.40 (d, J=7.0 Hz, 2H), 2.11 (m, 1H), 1.91 (s, 6H), 1.85-1.35 (m, 9H), 1.31 (d, J=7.1 Hz, 3H), 0.85 (d, J=7.7 Hz, 6H) ppm.

Example 50

Tramadolium Meclofenamate [4]

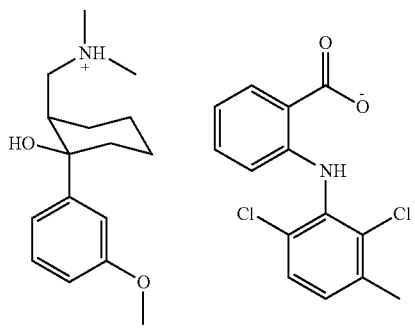

[4]

Tramadolium hydrochloride (0.492 g, 1.64 mmol) and sodium meclofenamate (0.522 g, 1.64 mmol) were dissolved in 20 ml of acetone/H₂O 1:1 and stirred overnight at room temperature. The remaining suspension was diluted with 50 ml of H₂O and extracted with dichloromethane. The organic layer was washed successively with water until no more chloride ions could be detected in the washings (checked by addition of AgNO₃ solution), dried over MgSO₄ and the solvent was evaporated. Remaining volatile material was removed under reduced pressure (0.01 mbar) to give tramadolium meclofenamate [3] in 95% yield as colourless solid foam. Identity and purity of the obtained product were confirmed via ¹H NMR. ¹H-NMR (300 MHz, d₆-DMSO) δ(ppm) =10.62 (br s, 1H), 7.95 (dd, J₁=7.9 Hz, J₂=1.2 Hz, 1H), 7.50 (d, J=8.3, 1H), 7.3 (d, J=7.9 Hz, 1H), 7.28 (d, J=7.9 Hz, 1H), 7.18 (t, J=7.7 Hz, 1H), 7.10 (m, 2H), 6.80 (dd, J₁=8.1 Hz, J₂=2.2 Hz, 1H), 6.71 (t, J=7.5 Hz, 1H), 5.82 (br s, 1H), 3.78 (s, 3H), 2.60 (m, 1H, 2.40 (s, 3H), 2.32 (s, 6H), 2.11 (m, 2H), 1.99 (d, 11.9 Hz, 1H), 1.61 (m, 7H). ¹³C-NMR (75 MHz, d₆-DMSO) δ(ppm)=171.3, 159.1, 150.7, 146.3, 136.3, 135.8, 133.2, 131.7, 131.6, 130.1, 128.9, 128.4, 128.0, 117.3, 116.7, 112.3, 74.2, 59.7, 54.9, 43.9, 41.6, 40.7, 26.2, 25.0, 21.4, 20.2. $T_g$ 38° C., $T_{5\%onset}$ 172° C.

Example 51

Tramadolium Docusate [5]

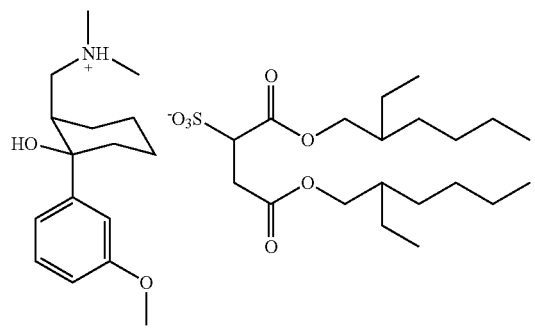

[5]

Tramadolium hydrochloride (0.5997 g, 2 mmol) and sodium docusate (0.8892 g, 2 mmol) were dissolved in 20 ml of acetone/H₂O 1:1 and stirred overnight at room temperature. The remaining suspension was diluted with 50 ml of H₂O and extracted with dichloromethane. The organic layer was washed successively with water until no more chloride ions could be detected in the washings (checked by addition of AgNO₃ solution), dried over MgSO₄ and the solvent was evaporated. Remaining volatile material was removed under reduced pressure (0.01 mbar) to give tramadolium docusate [3] in quantitative yield as yellow oil. ¹H-NMR (300 MHz, d₆-DMSO) δ(ppm)=7.26 (t, 1H, J=8.0 Hz), 7.06 (m, 2H), 6.79 (dd, 1H, J₁=8.1, J₂=2.3 Hz), 5.17 (b s, 1H, OH), 3.88 (m, 2H), 3.74 (s, 3H), 3.64 (dd, 1H, J₁=3.7 Hz, J₂=11.1 Hz), 2.86 (m, 3H), 2.38 (d, 2H), 2.22 (m, 2H), 1.9-1.5 (m, 4H), 1.5 (m, 2H), 1.3-1.1 (m, 16H), 0.8 (m, 12H). ¹³C-NMR (75 MHz, d₆-DMSO) δ(ppm)=171.36, 168.62, 159.54, 150.11, 129.52, 117.48, 111.88, 111.43, 74.15, 66.60, 66.53, 66.49, 66.44, 61.80, 59.89, 55.29, 40.68, 38.49, 34.40, 30.08, 29.97, 29.91, 28.69, 25.79, 24.68, 23.52, 23.36, 22.76, 22.73, 21.45, 14.24, 14.21, 11.14, 11.11, 11.07. $T_g$ –6° C., $T_{5\%onset}$ 226° C.

Example 52

Cetylpyridinium Salicylate [6]

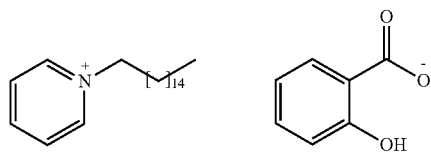

Cetylpyridinium chloride monohydrate (20.64 g, 56 mmol) and sodium salicylate (8.96 g, 56 mmol) were dissolved in 100 ml of acetone/$H_2O$ 1:1 and stirred overnight at room temperature. The remaining suspension was diluted with 100 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give cetylpyridinium salicylate [6] in 56% yield as colourless waxy solid. $^1$H-NMR (300 MHz, $d_6$-DMSO) δ(ppm)=9.12 (d, J=6.08 Hz, 2H), 8.59 (t, J=8.29 Hz, 1H), 8.16 (t, J=7.27 Hz, 2H), 7.64 (d, 7.54 Hz, 1H), 7.12 (t, J=7.54, 1H), 6.57 (m, 2H), 4.59 (t, J=7.44 Hz, 2H), 1.88 (m, 2H), 1.22 (s, 27H), 0.84 (t, J=7.14 Hz, 3H). $^{13}$C-NMR (75 MHz, $d_6$-DMSO) δ(ppm)= 171.8, 163.4, 145.8, 145.2, 131.4, 130.2, 128.4, 121.1, 116.1, 160.0, 61.2, 31.7, 31.2, 29.4, 29.3, 29.2, 29.1, 28.8, 25.8, 22.5, 14.2. mp 57° C., $T_{5\%onset}$ 206° C.

Example 53

Benzethonium Salicylate [7]

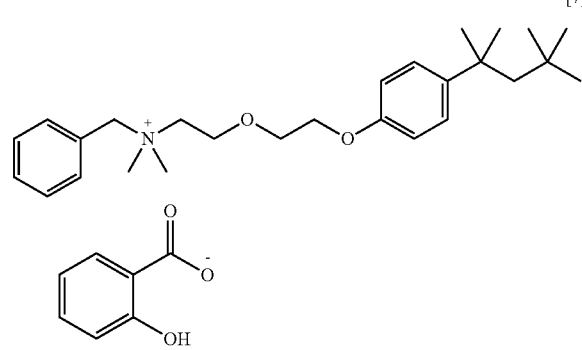

Benzethonium chloride (4.481 g, 10 mmol) and sodium salicylate (1.601 g, 10 mmol) were dissolved in 50 ml of acetone/$H_2O$ 1:1 and stirred overnight at room temperature. The remaining suspension was diluted with 50 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give benzethonium salicylate [6] as yellow glass. $^1$H-NMR (300 MHz, $d_6$-DMSO) δ(ppm) =7.65 (m, 1H), 7.53 (m, 5H), 7.26 (d, J=8.9 Hz, 2H), 7.10 (s, 1H), 6.82 (d, J=8.9 Hz, 2H), 6.57 (m, 2H), 4.61 (s, 2H), 4.11 (s, 2H), 4.00 (m, 2H), 3.82 (s, 2H), 3.39 (m, 2H), 3.02 (s, 6H), 1.67 (s, 2H), 1.28 (s, 6 H), 0.66 (s, 9H). $^{13}$C-NMR (75 MHz, $d_6$-DMSO) δ(ppm)=171.0, 168.3, 141.0, 128.2, 127.4, 125.8, 69.7, 66.2, 61.5, 59.1, 38.2, 34.1, 30.7, 29.8, 29.6, 28.4, 23.2, 23.0, 22.5, 13.9, 10.8, 9.2. $T_g$ –14° C., $T_{5\%onset}$ 180° C.

Example 54

Lidocainium Salicylate [8]

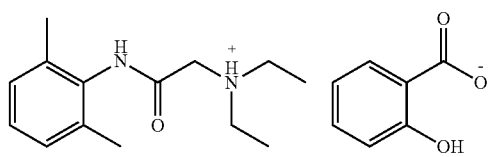

Lidocaine hydrochloride monohydrate (23.105 g, 80 mmol) and sodium salicylate (8.962 g, 80 mmol) were dissolved in 10 ml of acetone/$H_2O$ 1:1 and stirred overnight at room temperature. The remaining suspension was diluted with 100 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give lidocainium salicylate [8] in 54% yield as pale yellow viscous oil.

Solvent-Free Procedure:

Salicylic acid (5 mmol) and lidocaine free base (5 mmol) were molten in a hot mortar until a free-flowing clear liquid was obtained. The mixture was cooled to room temperature and formed a viscous glass. $^1$H-NMR (300 MHz, $d_6$-DMSO) δ(ppm)=10.05 (br s, 1H), 7.72 (dd, $J_1$=7.75 Hz, $J_2$=1.80 Hz, 1H), 7.24 (m, 1H), 7.09 (s, 3H), 6.70 (m, 2H), 3.98 (s, 2H), 3.10 (q, J=7.28 Hz, 4 H), 2.16 (s, 6H), 1.22 (t, J=7.34 Hz, 6 H). $^{13}$C-NMR (75 MHz, $d_6$-DMSO) δ(ppm)=171.9, 164.6, 161.9, 135.0, 134.0, 133.4, 130.1, 127.8, 126.9, 117.6, 116.9, 116.4, 53.3, 48.3, 18.1, 9.5. $T_g$ 19° C., $T_{5\%onset}$ 161° C.

Example 55

Tetrabutylphosphonium Salicylate [9]

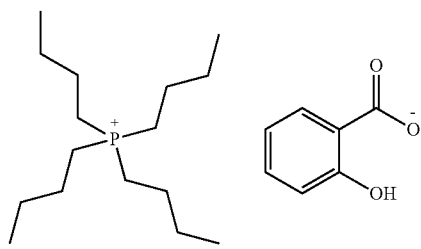

Salicylic acid (0.691 g, 5 mmol) and tetrabutylphosphonium hydroxide (~40% sol. in $H_2O$) (3.414 g, 5 mmol) were dissolved in 20 ml of acetone stirred for 15 min at room temperature. The solvent was evaporated and the remaining viscous liquid was dried at 0.1 mbar with stirring for 24 hrs to obtain tetrabutylphosphonium salicylate [9] in quantitative yield as colourless crystals. $^1$H-NMR (300 MHz, d$_6$-DMSO) δ(ppm)=7.74 (dd, J$_1$=7.73 Hz, J$_2$=1.87 Hz, 1H), 7.32 (dt, J$_1$=7.59 Hz, J$_2$=1.80 Hz, 1H), 6.77 (m, 2H), 2.20 (m, 8 H), 1.41 (m, 16 H), 0.9 (t, J=7.06 Hz, 12 H). $^{31}$P-NMR (121.5 MHz, d$_6$-DMSO) δ(ppm)=35.1. $^{13}$C-NMR (75 MHz, d$_6$-DMSO) δ(ppm)=171.9(s), 163.1(s), 131.1 (d), 129.8(d), 120.6 (s), 115.7 (d), 115.6 (d), 23.31 (d, J=16.36 Hz), 22.62 (d, 4.84 Hz), 17.30 (47.27 Hz), 13.19 (s). mp 57° C.; T$_{5\%onset}$ 312° C.; water content (KF) 0.076% (m/m).

Example 56

Ephedrinium Salicylate [10]

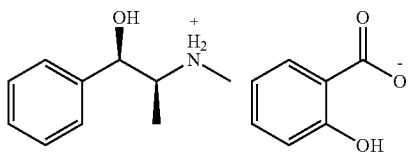

[10]

Salicylic acid (0.691 g, 5 mmol) and ephedrine (0.826 g, 5 mmol) were molten in a hot mortar until a free-flowing clear liquid was obtained. The mixture was cooled to room temperature solidified and was grinded to obtain a colourless powder in quantitative yield. $^1$H-NMR (300 MHz, d$_6$-DMSO) δ(ppm)=9.30 (br s, 2H), 7.76 (dd, J$_1$=7.66 Hz, J$_2$=1.80 Hz, 1H), 7.38 (m, 4H), 7.24 (m, 2H), 6.70 (m, 2H), 6.48 (br s, 1H), 5.21 (s, 1H), 3.41 (m, 1H), 2.69 (s, 3H), 0.95 (d, J=6.76 Hz, 3H). $^{13}$C-NMR (75 MHz, d$_6$-DMSO) δ(ppm)= 172.9, 162.1, 141.4, 132.0, 130.3, 128.2, 127.2, 125.8, 119.6, 116.8, 116.0, 69.6, 59.3, 30.6, 9.1. mp 97° C., T$_{5\%onset}$ 161° C.

Example 57

Ephedrinium Ibuprofenate [11]

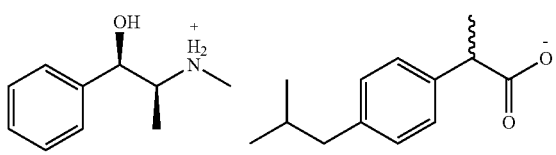

[11]

Ibuprofenic acid (0.691 g, 5 mmol) and ephedrine (0.826 g, 5 mmol) were molten in a hot mortar until a free-flowing clear liquid was obtained. The mixture was cooled to room temperature, solidified and was grinded to obtain a colourless powder in quantitative yield. $^1$H-NMR (300 MHz, d$_6$-DMSO) δ(ppm)=7.34 (m, 4H), 7.19 (m, 3H), 7.03 (d, J=7.89 Hz, 2H), 5.80 (br s, 1H), 4.97 (d, J=2.8 Hz, 1H), 3.45 (q, J=7.1 Hz, 1H), 3.04 (m, 1H), 2.45 (s, 3H), 2.38 (d, J=7.15 Hz, 2H), 1.78 (sept, J=6.8 Hz, 1H), 1.30 (d, J=7.17, 3 H), 0.83 (m, 9H). $^{13}$C-NMR (75 MHz, d$_6$-DMSO) δ(ppm)=177.9, 142.4, 140.9, 138.5, 128.5, 127.9, 127.1, 126.7, 125.9, 70.6, 59.8, 46.6, 44.3, 31.5, 29.7, 22.2, 19.5, 10.7. mp 110° C., T$_{5\%onset}$ 238° C.

Example 58

Ephedrinium Clofibrate [12]

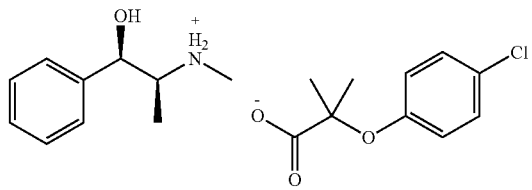

[12]

Clofibric acid (1.073 g, 5 mmol) and ephedrine (0.826 g, 5 mmol) were molten in a hot mortar until a free-flowing clear liquid was obtained. The mixture solidified at room temperature and was grinded to obtain a yellow powder in quantitative yield. $^1$H-NMR (300 MHz, d$_6$-DMSO) δ(ppm)=9.36 (br s, 2H), 7.30 (m, 5H), 7.19 (d, J=8.8 Hz, 2H), 6.82 (d, J=8.75 Hz, 2H), 5.10 (s, 1H), 3.12 (m, 1H), 2.52 (s, 3H), 1.41 (s, 6H), 0.85 (d, J=6.58 Hz), 3H). $^{13}$C-NMR (75 MHz, d$_6$-DMSO) δ(ppm)= 176.8, 155.5, 141.8, 128.5, 128.0, 126.9, 125.8, 123.4, 119.2, 80.2, 69.8, 59.5, 30.7, 25.8, 9.6. mp 131° C., T$_{5\%onset}$ 166° C.

Example 59

Ephedrinium Docusate [13]

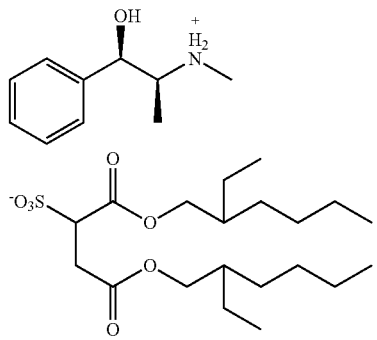

[13]

Ephedrinium hydrochloride (2.017 g, 10 mmol) and sodium docusate (4.446 g, 10 mmol) were dissolved in 50 ml of acetone/H$_2$O 1:1 and stirred overnight at room temperature. The remaining suspension was diluted with 50 ml of H$_2$O and extracted with dichloromethane. The organic layer was washed successively with water until no more chloride ions could be detected in the washings (checked by addition of AgNO$_3$ solution), dried over MgSO$_4$ and the solvent was evaporated. Remaining volatile material was removed under reduced pressure (0.01 mbar) to give ephedrinium docusate [13] in 98% yield as colourless viscous oil. $^1$H-NMR (300 MHz, d$_6$-DMSO) δ(ppm)=8.45 (br s, 2H), 7.34 (m, 5H), 6.13 (d, J=4.24 Hz, 1H), 5.06 (t, J=3.22 Hz, 1H), 3.89 (m, 4H), 3.65 (dd, J$_1$=11.47 Hz, J$_2$=3.91 Hz, 1H), 2.86 (m, 2H), 2.64 (s, 3H), 1.49 (m, 2H), 1.23 (m, 16 H), 0.86 (m, 15 H). $^{13}$C-NMR (75 MHz, d$_6$-DMSO) δ(ppm)=171.0, 168.3, 141.0, 128.2, 127.4, 125.8, 69.6, 66.2, 61.5, 59.0, 38.2, 34.1, 30.7, 29.8, 29.6, 28.4, 23.2, 23.0, 22.5, 13.9, 10.8, 9.2. T$_g$−25° C., T$_{5\%onset}$ 238° C.

Example 60

Promethazine Docusate [14]

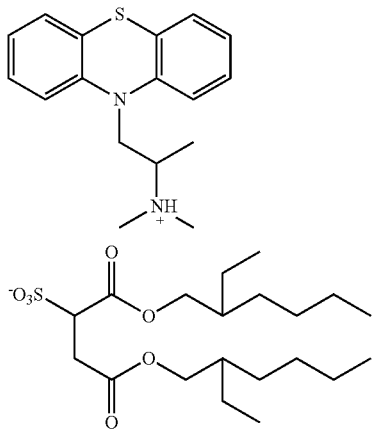

Promethazine hydrochloride (3.209 g, 10 mmol) and sodium docusate (4.446 g, 10 mmol) were dissolved in 50 ml of acetone/H$_2$O 1:1 and stirred overnight at room temperature. The remaining suspension was diluted with 50 ml of H$_2$O and extracted with dichloromethane. The organic layer was washed successively with water until no more chloride ions could be detected in the washings (checked by addition of AgNO$_3$ solution), dried over MgSO$_4$ and the solvent was evaporated. Remaining volatile material was removed under reduced pressure (0.01 mbar) to give promethazine docusate [14] in 99% yield as light yellow oil. $^1$H-NMR (300 MHz, d$_6$-DMSO) δ(ppm)=9.59 (br s, 1H), 7.26 (m, 6H), 7.04 (t, J=7.3 Hz, 2H), 4.37 (dd, J$_1$=14.3 Hz, J$_2$=4.8 Hz, 1H), 4.05 (dd, J$_1$=14.6 Hz, J$_2$=8.1 Hz, 1H), 3.89 (m, 4H), 3.66 (m, 2H), 2.91 (m, 2H), 2.82 (s, 6H), 1.49 (m, 2H), 1.28 (d, J=6.5 Hz, 3H), 1.22 (m, 16 H), 0.83 (m, 12 H). T$_{5\%onset}$ 246° C.

Example 61

Procainamide Salicylate [15]

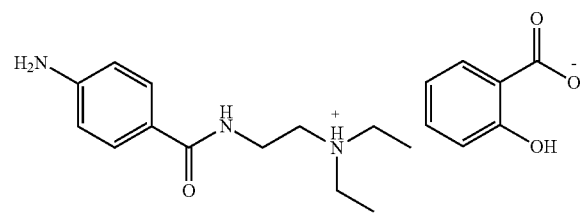

Procainamide hydrochloride (2.718 g, 10 mmol) and sodium salicylate (1.601 g, 10 mmol) were dissolved in 10 ml of acetone/H$_2$O 1:1 and stirred overnight at room temperature. The clear solution was evaporated and the residue dissolved in anhydrous acetone. The suspension was filtered over celite and the filtrate was evaporated. Remaining volatile material was removed under reduced pressure (0.01 mbar) to give procainamide salicylate [15] as pale yellow viscous oil. $^1$H-NMR (300 MHz, d$_6$-DMSO) δ(ppm)=8.47 (t, J=5.6 Hz, 1H), 7.72 (dd, J$_1$=7.7 Hz, J$_2$=1.9 Hz, 1H), 7.60 (d, J=8.7 Hz, 2H), 7.23 (m, 1H), 6.71 (m, 2H), 6.54 (d, J=8.6 Hz, 2H), 3.60 (s, 2H), 3.19 (m, 6H), 1.23 (t, J=7.1 Hz, 6H). $^{13}$C-NMR (75 MHz, d$_6$-DMSO) δ(ppm)=172.5, 166.9, 162.2, 152.0, 132.2, 130.2, 128.8, 120.4, 119.1, 116.8, 1160.0, 112.5, 50.0, 46.7, 34.3, 8.6. T$_{5\%onset}$ 199° C.

Example 62

Procainamide Ibuprofenate [16]

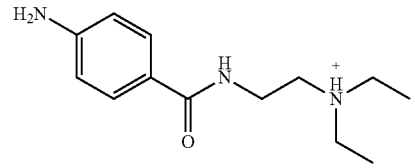

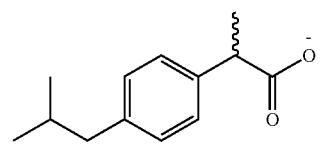

Procainamide hydrochloride (2.718 g, 10 mmol) and racemic sodium ibuprofenate (2.283 g, 10 mmol) were dissolved in 50 ml of acetone/H$_2$O 1:1 and stirred overnight at room temperature. The remaining suspension was diluted with 50 ml of H$_2$O and extracted with dichloromethane. The organic layer was washed successively with water until no more chloride ions could be detected in the washings (checked by addition of AgNO$_3$ solution), dried over MgSO$_4$ and the solvent was evaporated. Remaining volatile material was removed under reduced pressure (0.01 mbar) to give procainamide ibuprofenate [16] in as viscous yellow liquid.

$^1$H-NMR (300 MHz, d$_6$-DMSO) δ(ppm)=7.96 (t, J=5.7 Hz, 1H), 7.56 (d, J=8.6 Hz, 2H), 7.20 (d, J=8.8 Hz, 2H), 6.69 (d, 8.8 Hz, 2H), 6.54 (d, J=8.6 Hz, 2H), 5.60 (br s, 2H), 3.61 (q, 7.2 Hz, 1H), 3.29 (m, 2H), 2.56 (m, 6H), 2.42 (d, J=7.2 Hz, 2H), 1.82 (sept, 6.9 Hz, 1H), 1.35 (d, J=6.9 Hz, 3H), 0.99 (t, 7.1 Hz, 6H), 0.86 (d, J=6.8 Hz, 6H). $^{13}$C-NMR (75 MHz, d$_6$-DMSO) δ(ppm)=175.7, 166.1, 151.5, 139.4, 138.9, 128.9, 128.6, 127.1, 121.3, 112.5, 51.6, 46.7, 44.6, 44.2, 37.0, 29.6, 22.2, 18.7, 11.6. $T_{5\%onset}$ 182° C.

Example 63

Procainamide Docusate [17]

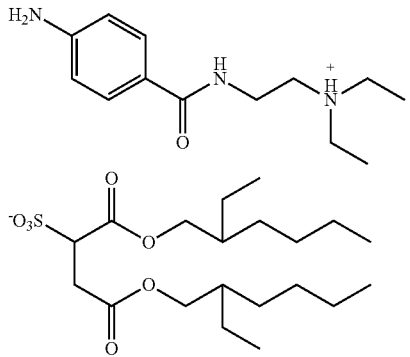

[17]

Procainamide hydrochloride (2.718 g, 10 mmol) and sodium docusate (4.4456 g, 10 mmol) were dissolved in 20 ml of acetone/$H_2O$ 1:1 and stirred overnight at room temperature. The remaining suspension was diluted with 50 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give procainamide docusate [17] in quantitative yield as yellow oil. $^1$H-NMR (300 MHz, $d_6$-DMSO) δ(ppm)=9.08 (br s, 1H), 8.27 (t, J=5.6 Hz, 1H), 7.52 (d, J=8.6 Hz, 2H), 6.55 (d, J=8.6 Hz, 2H), 5.71 (br s, 2H), 3.89 (m, 4H), 3.65 (dd, $J_1$=11.5 Hz, $J_2$=38 Hz, 1H), 3.53 (q, 6.1 Hz, 2H), 3.2 (m, 6H), 2.87 (m, 4H), 1.49 (m, 2H), 1.22 (m, 22H), 0.84 (m, 12H).
$T_{5\%onset}$ 231° C.

Example 64

Triethanolammonium Ibuprofenate [18]

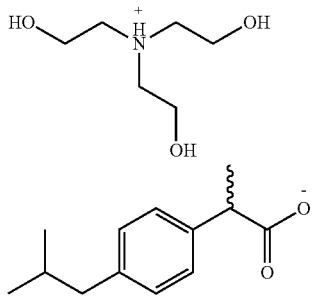

[18]

Ibuprofenic acid (1.032 g, 5 mmol) and triethanolamine (0.746 g, 5 mmol) were molten in a hot mortar until a free-flowing clear liquid was obtained. The mixture solidified at room temperature and was grinded to obtain colourless powder in quantitative yield. 1H-NMR (300 MHz, $d_6$-DMSO) δ(ppm)=7.20 (d, J=8.1 Hz, 2H), 7.1 (d, 8.1 Hz, 2H), 5.77 (br s, 3H), 3.61 (q, 7.2 Hz, 1H), 3.45 (t, J=6.1, 6H), 2.61 (t, J=6.1 Hz, 6H), 2.42 (d, J=7.2 Hz, 2H), 2.42 (d, 7.2 Hz, 2H), 1.82 (sept, 6.8 Hz, 1H), 1.35 (d, J=7.1 Hz, 3H), 0.87 (d, J=6.6 Hz, 6H). $^{13}$C-NMR (75 MHz, $d_6$-DMSO) δ(ppm)=175.7, 139.4, 138.8, 128.9, 127.1, 59.0, 57.1, 44.6, 44.3, 29.6, 22.2, 18.7. mp 90° C., $T_{5\%onset}$ 163° C.

Example 65

Tetrabutylphosphonium Ibuprofenate [19]

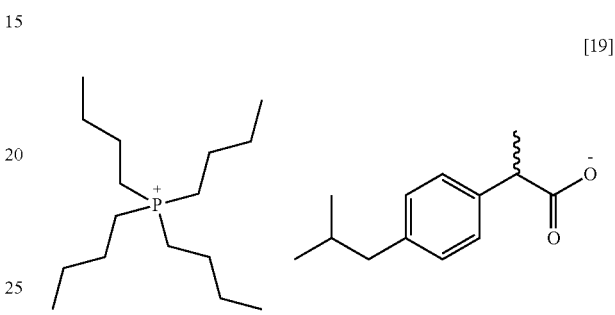

[19]

Ibuprofenic acid (1.032 g, 5 mmol) and tetrabutylphosphonium hydroxide (~40% sol. in $H_2O$) (3.414 g, 5 mmol) were dissolved in 20 ml of acetone stirred for 15 min at room temperature. The solvent was evaporated and the remaining viscous liquid was dried at 0.1 mbar with stirring for 24 hrs to obtain tetrabutylphosphonium ibuprofenate [19] in quantitative yield as colourless viscous liquid. $^1$H-NMR (300 MHz, $d_6$-DMSO) δ(ppm)=7.13 (d, J=8.08 Hz, 2H), 6.94 (d, 8.08 Hz, 2H), 3.21 (q, 7.74 Hz, 1H), 2.48 (m, 2H), 2.36 (d, 7.28 Hz, 2H), 2.14 (m, 8H), 1.77 (sept, 6.15 Hz, 1H), 1.40 (m, 16 H), 1.18 (d, J=7.03 Hz, 3H), 0.91 (t, 7.02 Hz, 12H), 0.84 (d, J=7.02 Hz, 6H). $^{13}$C-NMR (75 MHz, $d_6$-DMSO) δ(ppm) =174.8, 144.2, 136.9, 127.8, 127.2, 49.3, 44.4, 29.7, 23.4 (d, J=15.8 Hz), 22.7 (d, J=4.7 Hz), 22.2, 20.5, 17.3 (d, J=48.1 Hz), 13.3. mp–43° C., $T_{5\%onset}$ 234° C.

Example 66

Tributylhydroxyethylphosphonium Docusate [20]

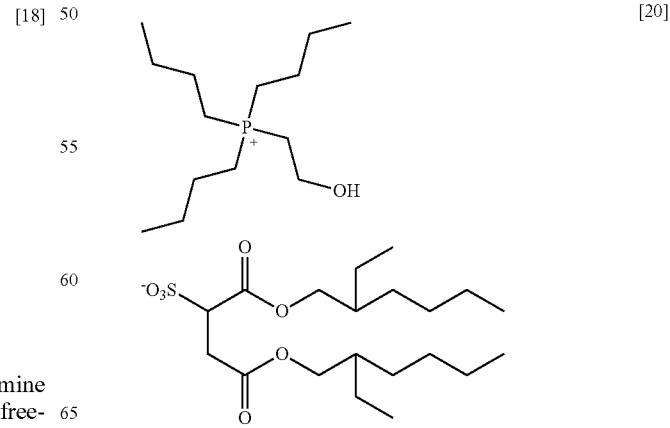

[20]

Tributylhydroxyethylphosphonium chloride (10.019 g, 35.5 mmol) and sodium docusate (15.770 g, 35.5 mmol) were dissolved in 100 ml of acetone/$H_2O$ 1:1 and stirred overnight at room temperature. The remaining suspension was diluted with 100 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give tributylhydroxyethylphosphonium docusate [20] in 92% yield as colourless liquid. $^1$H-NMR (300 MHz, $d_6$-DMSO) δ(ppm)=5.77 br s, 1H), 3.82 (m, 6H), 3.63 (dd, $J_1$=11.3 Hz, $J_2$=3.8 Hz, 1H), 2.85 (m, 2H), 2.42 (m, 2H), 2.20 (m, 6H), 1.43 (m, 14H), 0.92 (t, J=7.1 Hz, 9H), 0.84 (m, 12H). $^{31}$P-NMR (121.5 MHz, $d_6$-DMSO) δ(ppm)=34.5. $^{13}$C-NMR (75 MHz, $d_6$-DMSO) δ(ppm)=171.0, 163.3, 66.1, 66.0, 61.4, 54.4, 54.3, 38.1, 34.1, 29.7, 28.6, 29.5, 28.3, 23.6 (d, J=15.9 Hz), 23.2, 23.0, 22.7 (d, 4.9 Hz), 22.4, 22.3, 18.1 (d, 48.5), 13.9, 13.8, 13.2, 10.7. $T_g$ −45° C., $T_{5\%onset}$ 280° C.

Example 67

Choline Docusate [21]

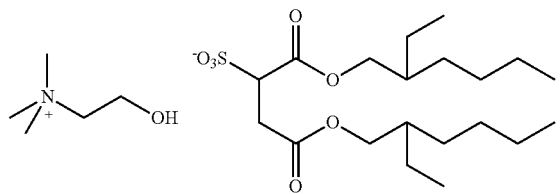

[21]

Choline chloride (1.396 g, 10 mmol) and sodium docusate (4.4456 g, 10 mmol) were dissolved in 50 ml of acetone/$H_2O$ 1:1 and stirred overnight at room temperature. The remaining suspension was diluted with 50 ml of $H_2O$ and extracted with dichloromethane. The organic layer was washed successively with water until no more chloride ions could be detected in the washings (checked by addition of $AgNO_3$ solution), dried over $MgSO_4$ and the solvent was evaporated. Remaining volatile material was removed under reduced pressure (0.01 mbar) to give choline docusate [21] in quantitative yield as yellow very viscous liquid. $^1$H-NMR (300 MHz, $d_6$-DMSO) δ(ppm)=4.88 (t, J=5.4 Hz, 1H), 4.21 (dd, $J_1$=10.6 Hz, $J_2$=4.32 Hz, 1H), 4.02 (m, 6H), 3.63 (m, 2H), 3.8 (s, 9H), 3.2 (m, 4H), 1.57 (m, 2H), 1.27 (m, 16H), 0.87 (m, 12H). $T_{5\%onset}$ 189° C.

Ionic Liquid Solvates

Example 68

Propantheline p-Toluenesulfonate

A mixture of propantheline bromide (3.32 g, 7.41 mmol) and silver p-toluenesulfonate (2.07 g, 7.41 mmol) in acetonitrile (100 mL) was protected from light and stirred overnight at room temperature. A yellow precipitate formed instantaneously. The reaction mixture was filtered through Celite to remove AgBr. The filtrate was then re-filtered through microfilters (0.20 μm). The solvent was evaporated to leave a clear yellow viscous residue. To remove any colour from the sample, propantheline p-toluenesulfonate was re-dissolved in acetonitrile and two spatulas of activated charcoal (6-12 Mesh) were added to the solution. The mixture was left stirring overnight and then filtered through activated aluminum oxide (basic, Brockmann I). The solvent was removed leaving a clear viscous oily residue. The product was dried under vacuum on a Shlenk line at 55° C. for 3 hours. (crude yield: 91%)

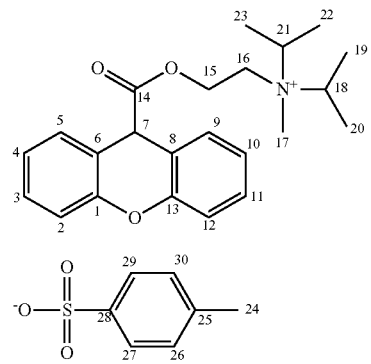

Propantheline p-Toluenesulfonate $^1$H NMR (300 MHz, $d_6$-DMSO): δ 1.13-1.18 (q, J 3.9, 12H; H19, H20, H22, H23), 2.28 (s, 3H; H24), 2.66 (s, 3H; H17), 3.41-3.46 (t(b), J4.7, 2H; H16), 3.71-3.77 (m, 2H; H18, H21), 4.34-4.39 (t(b), J 4.7, 2H; H15), 5.31 (s, 1H; H7), 7.09-7.12 (m, 2H; H26, H30), 7.12-7.22 (m, 4H; H2, H4, H10, H12), 7.39-7.40 (m, 4H; H3, H5, H9, H11), 7.46-7.49 (m, 2H; H27, H29). $^{13}$C NMR (75 MHz, $d_6$-DMSO): δ 16.13-16.20 (C19, C20, C22, C23); 20.70 (C24); 40.81 (C17); 44.07 (C7); 54.18 (C16); 59.72 (C15); 63.84 (C18, C21); 116.54 (C2, C12); 118.22 (C6, C8); 123.62 (C4, C10); 125.44 (C27, C29); 127.95 (C26, C30); 129.35 (C3, C11); 129.53 (C5, C9); 137.46 (C28); 145.85 (C25); 150.86 (C1, C13); 170.32 (C14). MS (ESI): ES+ m/z: 368.0 (propantheline$^+$), ES− m/z: 171.0 (p-toluenesulfonate$^-$). ISE: The bromide concentration was determined by dissolving 0.2056 g of propantheline p-toluenesulfonate in 10 mL of methanol, indicating <100 ppm bromide. DSC: A reproducible Tg at 7±° C.

Compositions

Viscosity, conductivity and ΔW values for various propantheline p-toluenesulfonate (PtTos)/water composites.

TABLE X

| Compositions | Viscosity (mPa·s) ± 1% | Conductivity (S cm$^{-1}$)** | ΔW |
|---|---|---|---|
| PtTos pure* | >2000* | 5.41 × 10$^{-7}$ | 2.0 |
| Water:PTTos (25 wt %) | 3 | 30.1 × 10$^{-4}$ | 0.69 |
| Water:PTTos (20 wt %) | 3 | 26.1 × 10$^{-4}$ | 0.77 |
| Water:PTTos (4.8 wt %) | 1 | 15.2 × 10$^{-4}$ | 0.63 |

*instrument limit
**conductivity error does not exceed the data point in all cases
*** ΔW—distance form the ideal line The low ionicity nature of the ionic liquid is demonstrated via the Walden plot according to the discussion of Fraser et al (Chem Commun 2007). Data for this compound are plotted in FIG. 7 which shows that it lies 2 log units below the reference line, suggesting the degree of ionicity is only approximately 1%. With addition of 25 weight % water, ΔW value decreased. This is true for all of the propantheline p-toluenesulfonate/ water systems studied. With the increasing water content the ΔW seems to become approximately constant perhaps indicating that full dissociation had been reached.

What is claimed is:

1. A method for preparing a bioactive co-ionic ionic liquid composition comprising:

combining two pharmaceutical actives selected from single charged cations, cation precursors, and combinations thereof, represented as $B^1$ and $B^2$, with one anion having a single negative charge, represented as A, or combining two pharmaceutical actives selected from single charged anions, anion precursors, and combinations thereof, represented as $A^1$ and $A^2$, with one cation having a single positive charge, represented as B, thereby producing a co-ionic liquid $[B^1HB^2]A$ or $B[A^1HA^2]$, where H is hydrogen, that is liquid at a temperature at or below about 150° C., wherein $B^1$ and $B^2$ are selected from choline, lidocaine, tramadolium, caffeine, cetylpyridinium, ephedrinium, propantheline, acetaminophen derivative, procainamide, promethazine, and combinations thereof, and wherein $A^1$ and $A^2$ are selected from salicylate, ibuprofenate, lactate, camphorsulfonate, trans-cinnamate, docusate, niacinate, clofibrate, and combinations thereof.

2. The method of claim 1 wherein from about 75% to about 100% of the composition comprises an ion pair.

3. The method of claim 1, wherein the cations and anions or the cation precursors and anion precursors are combined in the presence of one or more solvents, thereby producing a solvated ionic liquid; wherein at least a portion of the solvent provides direct solvation.

4. The method according to claim 1, wherein combining two anions or anion precursors, represented as $A^1$ and $A^2$, with one cation, represented as B, is by adding acid $HA^2$ to a non-protic ionic liquid having the formula $BA^1$.

5. The method according to claim 1, wherein combining two cations or cation precursors, represented as $B^1$ and $B^2$, with one anion, represented as A, is by adding base $B^2$ to an ionic liquid having the formula $[B^1H]A$.

6. The method according to claim 1, wherein combining the two cation precursor with one anion or two anion precursor with one cation is accomplished by an acid-base neutralization reaction.

7. The method according to claim 1, wherein the cation B comprises tetrabutylphosphonium and the anion A comprises salicylate and ibuprofenate, cinnamate, camphorsulfonate, lactate or thiosalicylate.

8. The method according to claim 1, wherein the cation B is tetrabutylphosphonium and the anions $A^1$ and $A^2$ are ibuprofenate or niacinate.

9. The method according to claim 1, wherein the cation B is cetylpyridinium and the anions $A^1$ and $A^2$ are salicylate and ibuprofenate, cinnamate, or clofibrate.

10. The method according to claim 1, wherein the cation B is lidocaine and the anions $A^1$ and $A^2$ are salicylate and Ibuprofenate.

11. The method according to claim 1, wherein the cation B is tramadolium and the anions $A^1$ and $A^2$ are salicylate and ibuprofenate.

12. The method according to claim 1, wherein the cations $B^1$ and $B^2$ are ephedrinium and lidocaine and the anion A is ibuprofenate.

13. The method according to claim 1, wherein the cations $B^1$ and $B^2$ are tramadolium and lidocaine and the anion A is salicylate or ibuprofenate.

14. The method according to claim 1, wherein the cations $B^1$ and $B^2$ are promethazine and ephedrine and the anion A is docusate or salicylate.

* * * * *